(12) United States Patent
Yeung et al.

(10) Patent No.: US 11,147,642 B2
(45) Date of Patent: Oct. 19, 2021

(54) SYSTEMS, DEVICES, AND METHODS FOR PERFORMING SURGICAL ACTIONS VIA EXTERNALLY DRIVEN DRIVING ASSEMBLIES

(71) Applicant: BIO-MEDICAL ENGINEERING (HK) LIMITED, Hong Kong (CN)

(72) Inventors: Chung-Kwong Yeung, Hong Kong (CN); Siu-Hang Henry Hui, Hong Kong (CN)

(73) Assignee: Bio-Medical Engineering (HK) Limited, Hong Kong SAR (CN)

( * ) Notice: Subject to any disclaimer, the term of this patent is extended or adjusted under 35 U.S.C. 154(b) by 0 days.

(21) Appl. No.: 15/660,267

(22) Filed: Jul. 26, 2017

(65) Prior Publication Data
US 2018/0325614 A1 Nov. 15, 2018

Related U.S. Application Data

(63) Continuation of application No. PCT/CN2017/084394, filed on May 15, 2017.

(51) Int. Cl.
*A61B 34/00* (2016.01)
*A61B 34/30* (2016.01)
*A61B 17/00* (2006.01)
*A61B 17/29* (2006.01)
*A61B 90/00* (2016.01)
(Continued)

(52) U.S. Cl.
CPC ........ *A61B 34/71* (2016.02); *A61B 17/00234* (2013.01); *A61B 34/30* (2016.02);
(Continued)

(58) Field of Classification Search
CPC .............. A61B 34/71; A61B 17/00234; A61B 2034/715; A61B 2217/005;
(Continued)

(56) References Cited

U.S. PATENT DOCUMENTS 9,724,168 B2 * 8/2017 Yeung ................... A61B 34/30
2007/0299427 A1 * 12/2007 Yeung ..................... B25J 9/047
606/1

(Continued)

FOREIGN PATENT DOCUMENTS

CN 104605942 A 5/2015
CN 104688282 A 6/2015

OTHER PUBLICATIONS

International Search Report for PCT/CN2017/084394 dated Jan. 29, 2018, 5 pages.
(Continued)

*Primary Examiner* — Lynsey C Eiseman
*Assistant Examiner* — Jessandra F Hough
(74) *Attorney, Agent, or Firm* — Baker & McKenzie LLP

(57) ABSTRACT

Example embodiments relate to surgical devices, systems, and methods. The system includes a surgical arm, rotary driving assembly, and telescopic driving assembly. The surgical arm includes a plurality of segments and joints. The rotary driving assembly may be securable to a portion of a proximal end of the surgical arm. The rotary driving assembly may be configurable to rotate the surgical arm. The telescopic driving assembly may be securable to a portion of the proximal end of the surgical arm. The telescopic driving assembly may be configurable to provide a linear displacement of the surgical arm.

12 Claims, 31 Drawing Sheets

(51) Int. Cl.
*A61B 17/02* (2006.01)
*A61B 17/32* (2006.01)

(52) U.S. Cl.
CPC ........... *A61B 17/0218* (2013.01); *A61B 17/29* (2013.01); *A61B 17/320016* (2013.01); *A61B 90/361* (2016.02); *A61B 2017/00314* (2013.01); *A61B 2017/00327* (2013.01); *A61B 2017/2906* (2013.01); *A61B 2017/2908* (2013.01); *A61B 2034/302* (2016.02); *A61B 2034/305* (2016.02); *A61B 2034/306* (2016.02); *A61B 2034/715* (2016.02); *A61B 2217/005* (2013.01); *A61B 2217/007* (2013.01); *A61B 2218/002* (2013.01); *A61B 2218/007* (2013.01)

(58) Field of Classification Search
CPC ................ A61B 17/0218; A61B 17/29; A61B 17/320016; A61B 2217/007; A61B 2034/714; A61B 90/361; A61B 2017/00314; A61B 2017/00327; A61B 2017/2906; A61B 2017/2908
See application file for complete search history.

(56) References Cited

U.S. PATENT DOCUMENTS

| | | | |
|---|---|---|---|
| 2010/0274087 A1* | 10/2010 | Diolaiti | A61B 90/37 |
| | | | 600/118 |
| 2013/0012821 A1 | 1/2013 | Lin et al. | |
| 2013/0178867 A1 | 7/2013 | Farritor et al. | |
| 2014/0148819 A1* | 5/2014 | Inoue | A61B 17/32002 |
| | | | 606/130 |
| 2015/0297299 A1* | 10/2015 | Yeung | A61B 17/3421 |
| | | | 600/102 |
| 2016/0022298 A1 | 1/2016 | Parihar et al. | |
| 2016/0066919 A1 | 3/2016 | Dannaher | |
| 2016/0113638 A1 | 4/2016 | Malkowski et al. | |

OTHER PUBLICATIONS

Written Opinion of the International Searching Authority for PCT/CN2017/084394 dated Jan. 29, 2018, 4 pages.

Office Action dated Sep. 3, 2019 in connection with Chinese Application No. 201710601057.0, 11 pages.

* cited by examiner

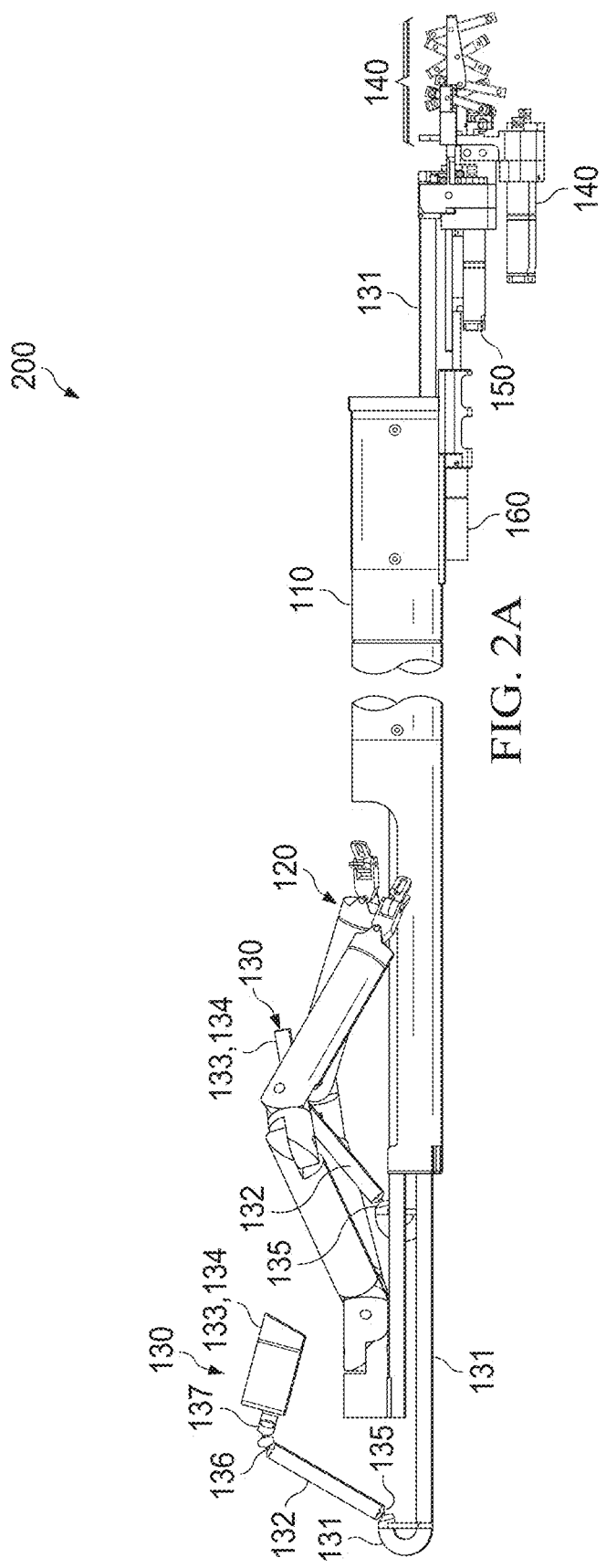

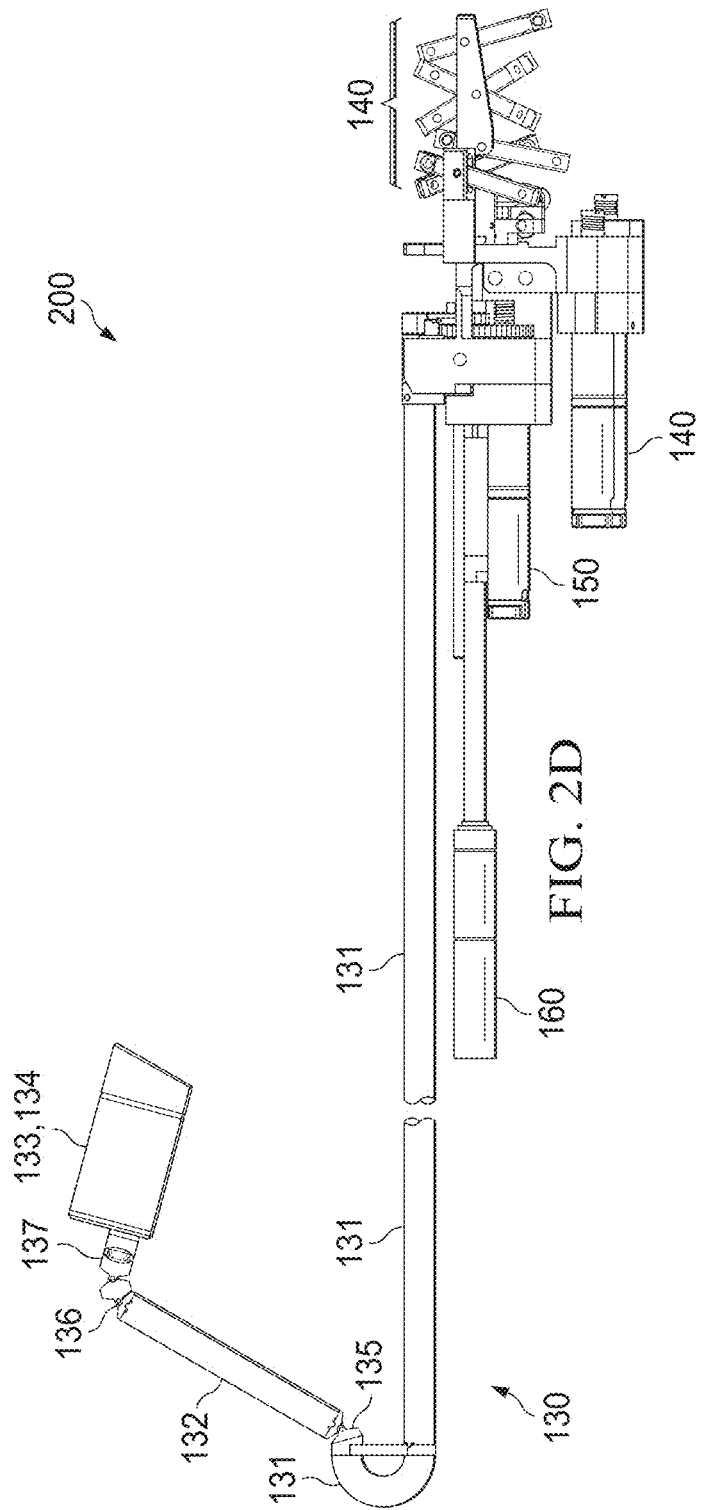

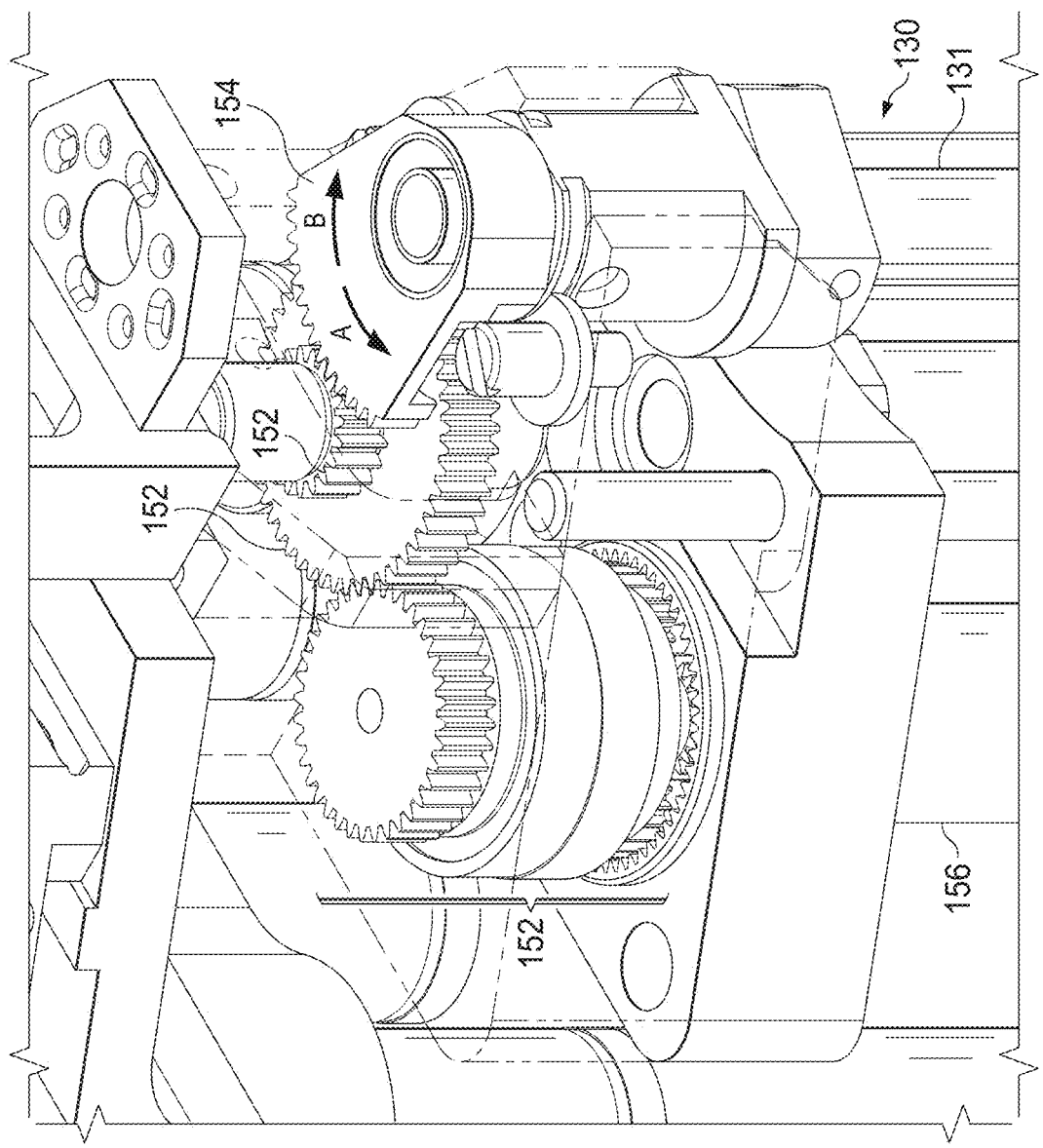

SYSTEMS, DEVICES, AND METHODS FOR PERFORMING SURGICAL ACTIONS VIA EXTERNALLY DRIVEN DRIVING ASSEMBLIES

CROSS-REFERENCE TO RELATED APPLICATIONS

This application is a continuation application of International Application No. PCT/CN2017/084394 (filed on May 15, 2017), the contents of all of which are hereby expressly incorporated by reference in their entirety, including the contents and teachings of any references contained therein.

BACKGROUND

The present disclosure relates generally to systems, devices, and methods for performing surgical procedures, and more specifically, relates to surgical robotic systems, devices, and methods for performing in vivo surgical actions including, but not limited to, minimally invasive surgical (MIS) procedures and natural orifice transluminal endoscopic surgical (NOTES) procedures.

Conventionally, surgical procedures performed in a body cavity of a patient, such as the abdominal cavity, required one or more large access incisions to a patient in order for the surgical team to perform a surgical action. With advancements in medical science and technology, such conventional surgical procedures have been largely replaced by minimally invasive surgery (MIS) procedures and, where applicable, natural orifice transluminal endoscopic surgical procedures (NOTES).

BRIEF SUMMARY

Recent developments in respect to computer-assisted and/or robotic surgical technology have contributed to advancements in the MIS and NOTES fields, including the ability to translate a surgeon's desired surgical actions into precise movements of surgical instruments inside a body cavity of a patient. Despite such recent developments, it is recognized in the present disclosure that one or more problems are encountered in modern surgical technology and methodology. For example, a typical MIS procedure requires multiple incisions to a patient in order to allow access via the incisions for the insertion of a camera and various other laparoscopic instruments into the body cavity of the patient.

As another example, surgical robotic systems oftentimes face difficulties in providing, at the same time within a patient's cavity, left and right surgical robotic arms each having a main instrument (such as a cutting or gripping instrument attached to the end of a surgical robotic arm) and one or more assistant instruments (such as a gripper, retractor, suction/irrigation, and/or image capturing device).

Present example embodiments relate generally to systems, devices, and methods for addressing one or more problems in surgical robotic systems, devices, and methods, including those described above and herein.

In an exemplary embodiment, a surgical system for use in performing an in vivo surgical action is described. The surgical system may be configurable to be inserted into an internal channel of a port assembly. The port assembly may serve as an access point into a cavity of a patient. The surgical system may include a surgical arm, a rotary driving assembly, and a telescopic driving assembly. The surgical arm may include a plurality of segments and joint assemblies, including first and second segments, an end effector assembly, at least one joint assembly pivotally coupling the first segment to the second segment, and at least one joint assembly pivotally coupling the second segment to the end effector assembly. The rotary driving assembly may be securable to a portion of a proximal end of the first segment. The rotary driving assembly may be configurable to rotate the surgical arm in a first direction relative to an axis formed by an elongated portion of the first segment and rotate the surgical arm in a second direction opposite to the first direction. The telescopic driving assembly may be securable to a portion of the port assembly and a portion of the proximal end of the first segment. The telescopic driving assembly may be configurable to provide a linear displacement of the surgical arm in a first linear direction and a second linear direction opposite to the first linear direction.

In another exemplary embodiment, a surgical system for use in performing an in vivo surgical action is described. The surgical system may include a port assembly, a first surgical arm, and a second surgical arm. The port assembly may be configurable as an access point into a cavity of a patient. The first surgical arm may be securable to the port assembly. The first surgical arm may include at least 7 degrees of freedom when secured to the port assembly. The first surgical arm may include a plurality of internal gear and motor assemblies in the first surgical arm, each internal gear and motor assembly configured to drive each of the at least 7 degrees of freedom. The second surgical arm may be securable to the port assembly. The second surgical arm may include at least 5 degrees of freedom when secured to the port assembly. The second surgical arm may include a plurality of segments and joint assemblies drivable to move relative to one another via an application of a tensile force to one or more cables. The second surgical arm may include first and second segments, an end effector assembly, at least one joint assembly pivotally coupling the first segment to the second segment, and at least one joint assembly pivotally coupling the second segment to the end effector assembly. A first degree of freedom of the second surgical arm may include a rotary movement of the second segment relative to an axis formed by an elongated portion of the first segment. A second degree of freedom of the second surgical arm may include a movement of the second surgical arm in a linear direction, the linear direction parallel to an axis formed by the port assembly when the second surgical arm is secured to the port assembly.

BRIEF DESCRIPTION OF THE DRAWINGS

For a more complete understanding of the present disclosure, example embodiments, and their advantages, reference is now made to the following description taken in conjunction with the accompanying drawings, in which like reference numbers indicate like features, and:

FIG. 2A is a side view of an example embodiment of a surgical system in a reverse configuration having main surgical arms, assistant surgical arms, port assembly, joint driving assembly, rotary driving assembly, and telescopic driving assembly;

FIG. 2D is a side view of an example embodiment of a surgical system in a reverse configuration having a surgical arm, joint driving assembly, rotary driving assembly, and telescopic driving assembly;

FIG. 311 is a perspective view of an example embodiment of a surgical system having a second joint assembly, end effector joint assembly, and end effector assembly;

FIG. 5A is a perspective view of an example embodiment of certain elements of the rotary driving assembly;

Although similar reference numbers may be used to refer to similar elements in the figures for convenience, it can be appreciated that each of the various example embodiments may be considered to be distinct variations.

Figure 1A:
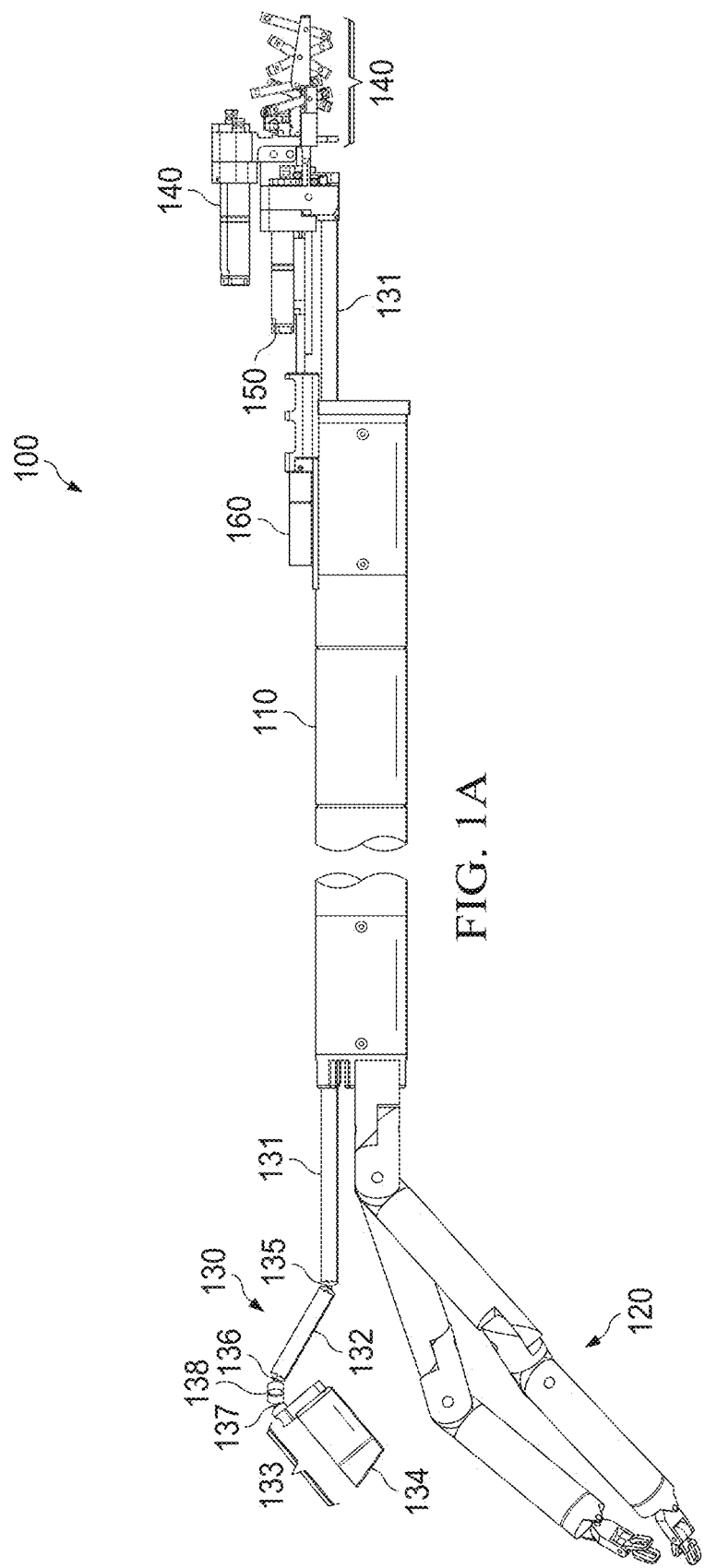
FIG. 1A is a side view of an example embodiment of a surgical system in a forward configuration having main surgical arms, assistant surgical arms, port assembly, joint driving assembly, rotary driving assembly, and telescopic driving assembly.

Example embodiments will now be described with reference to the accompanying drawings, which form a part of the present disclosure, and which illustrate example embodiments which may be practiced. As used in the present disclosure and the appended claims, the terms "example embodiment," "exemplary embodiment," and "present embodiment" do not necessarily refer to a single embodiment, although they may, and various example embodiments may be readily combined and/or interchanged without departing from the scope or spirit of example embodiments. Furthermore, the terminology as used in the present disclosure and the appended claims is for the purpose of describing example embodiments only and is not intended to be limitations. In this respect, as used in the present disclosure and the appended claims, the term "in" may include "in" and "on," and the terms "a," "an" and "the" may include singular and plural references. Furthermore, as used in the present disclosure and the appended claims, the term "by" may also mean "from," depending on the context. Furthermore, as used in the present disclosure and the appended claims, the term "if" may also mean "when" or "upon," depending on the context. Furthermore, as used in the present disclosure and the appended claims, the words "and/or" may refer to and encompass any and all possible combinations of one or more of the associated listed items.

DETAILED DESCRIPTION

Surgical robotic technology advancements in the MIS and NOTES fields have enabled surgeons to translate desired surgical actions into precise movements of surgical instruments inside a body cavity of a patient. Despite such recent developments, it is recognized in the present disclosure that one or more problems are encountered in modern surgical technology and methodology.

For example, a typical MIS or NOTES procedure will generally require a surgeon to perform multiple incisions to a patient in order to enable the surgeon to insert, via the incisions, required laparoscopic instruments into the body cavity of the patient. Furthermore, surgeons using known surgical systems often encounter problems in respect to utilizing a surgical instrument, such as a cutter, gripper, retractor, suction/irrigation device, and/or image capturing device (e.g., still or video cameras) attached to an end of a surgical robotic arm, in certain parts, areas, and/or quadrants of a body cavity (such as an abdomen) of a patient after the system has been set up (or anchored) and is ready to perform a surgical action. That is, after a surgical robotic arm has been inserted into and properly set up in the abdominal cavity of a patient, a surgical instrument attached to the end of the surgical robotic arm is typically mechanically limited to accessing only certain parts, areas, and quadrants of the abdominal cavity of the patient.

As another example, known surgical robotic systems typically only enable one to two surgical robotic arms to be inserted into a body cavity of a patient per access or opening (such as an incision or natural orifice). In this regard, when additional laparoscopic instruments, such one or more other surgical robotic arms, are required to be inserted into the abdominal cavity of the patient, one or more additional openings (incisions) are required to be performed on the patient. Additional problems may also be encountered in situations where there is a need to insert such laparoscopic instruments in a reverse manner or configuration (e.g., to access portions of the interior of the patient's cavity near the opening (e.g., incision or natural orifice)).

Recent technological developments have introduced solutions to one or more of the aforementioned problems. For example, U.S. patent application Ser. No. 14/693,207 to Yeung et al. ("U.S. Pat. No. '207"), herein incorporated by reference in its entirety, describes surgical robotic devices, systems, and methods, including a surgical system having a port assembly for use in providing sufficient anchoring and reactive forces to counter forces applied by one or more surgical arms of the surgical system during a surgical action. The surgical system of U.S. Pat. No. '207 enables a surgeon to not only perform a single small incision to the patient but also enables the surgeon to utilize one or a plurality of laparoscopic instruments, including surgical robotic arms and suction tubes, in an abdominal cavity of the patient through such single small incision (via the port assembly). U.S. Pat. No. '207 further teaches a surgical arm configurable to provide for seven in vivo degrees of freedom, thereby enabling a surgical instrument attached to the surgical arm to access all parts, areas, and quadrants of a body cavity. The combined design of the port assembly, surgical arms, and attachment portions for attaching the surgical arms to the port assembly further enable easy and controllable insertion and removal of surgical arms so as to prevent unintended contact with and damaging patient tissue. Furthermore, U.S. patent application Ser. Nos. 15/340,660 and 15/340,678 to Yeung and Ser. No. 15/340,699 to Yeung et al., all of which are herein incorporated by reference in their entireties, also describe surgical robotic devices, systems, and methods, including internally motorized surgical arms and detachable end effector assemblies for surgical arms.

In addition to the above-mentioned problems of known surgical systems encountered during forward-directed surgical procedures (e.g., MIS performed in an abdominal cavity of a patient), known surgical system generally encounter additional problems when deployed through a natural orifice, such as a rectum or vagina, for performing natural orifice transluminal endoscopic surgery (or NOTES), such as trans-vaginal gynecological procedures in women and trans-rectal urological procedures in men. For example, such known systems generally encounter problems pertaining to, among other things, the inability to access certain organs, tissues, or other surgical sites upon insertion into the natural orifice due as a result of the inherent forward-directed design of such systems.

Recent technological developments have introduced solutions to the aforementioned problems. For example, U.S. patent application Ser. Nos. 15/044,889 and 15/044,895 to Yeung ("U.S. Pat. No. '895"), both herein incorporated by reference in their entireties, describe a surgical system configurable for use in performing forward-directed and/or reverse-directed surgical actions.

Surgical systems, devices, and methods, including those for use in MIS and NOTES, are described in the present disclosure. It is to be understood in the present disclosure that the principles described herein can be applied outside of the context of MIS and/or NOTES, such as performing scientific experiments and/or procedures in environments that are not readily accessible by humans, including in a vacuum, in outer space, and/or under toxic and/or dangerous conditions, without departing from the teachings of the present disclosure.

The Surgical System (e.g., Surgical System 100, 200).

Figure 1B:
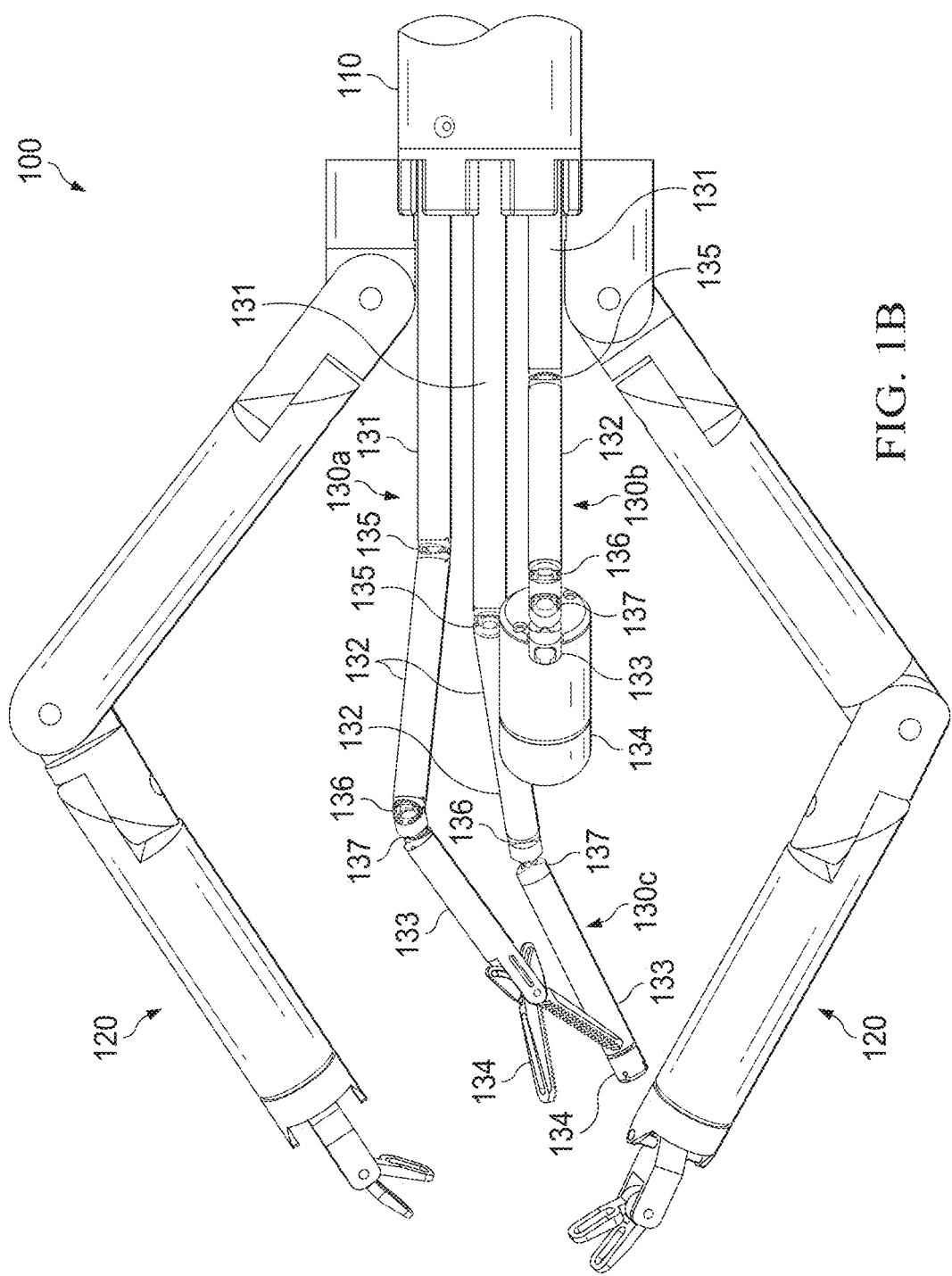
FIG. 1B is a top view of an example embodiment of a surgical system in a forward configuration having main surgical arms, assistant surgical arms, port assembly, joint driving assembly, rotary driving assembly, and telescopic driving assembly.
Figure 1C:
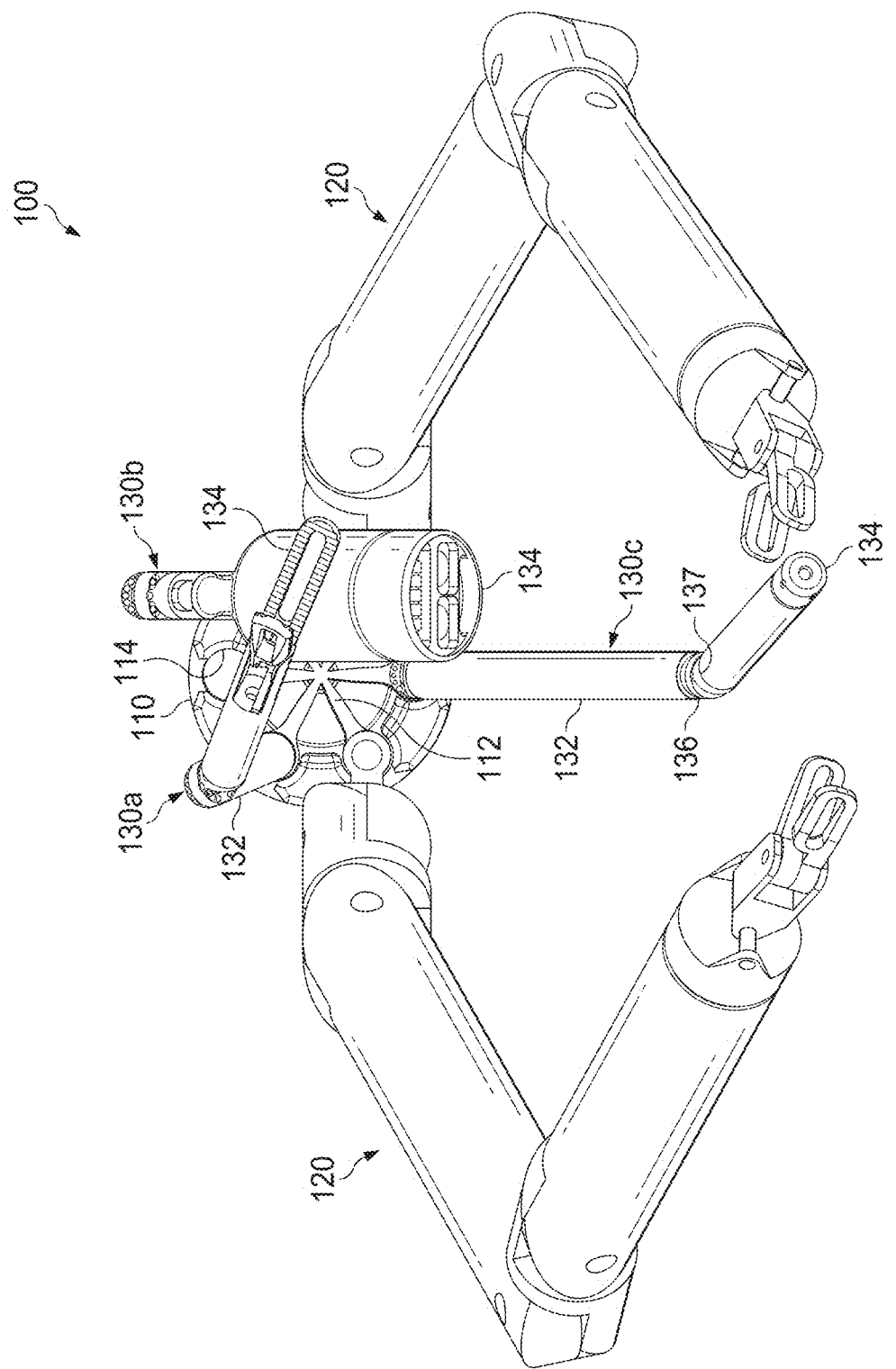
FIG. 1C is a front view of an example embodiment of a surgical system in a forward configuration having main surgical arms, assistant surgical arms, port assembly, joint driving assembly, rotary driving assembly, and telescopic driving assembly.
Figure 1D:
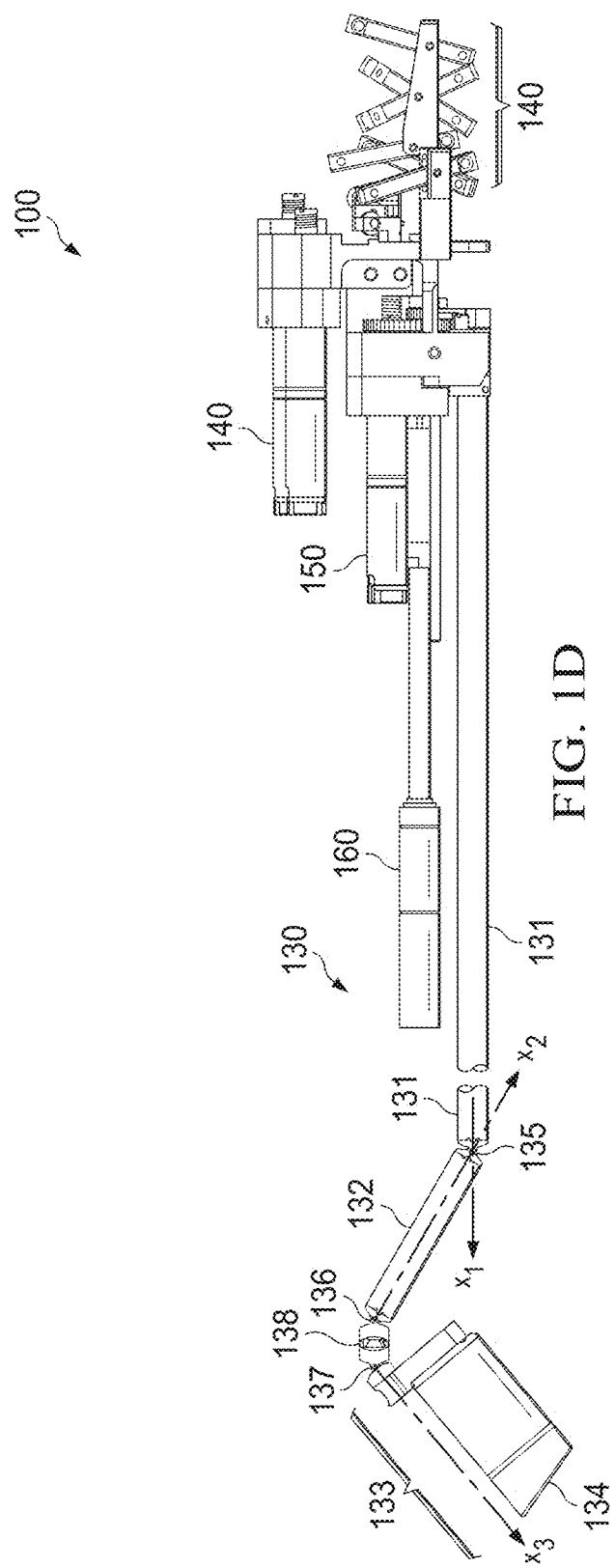
FIG. 1D is a side view of an example embodiment of a surgical system in a forward configuration having a surgical arm, joint driving assembly, rotary driving assembly, and telescopic driving assembly.
Figure 2B:
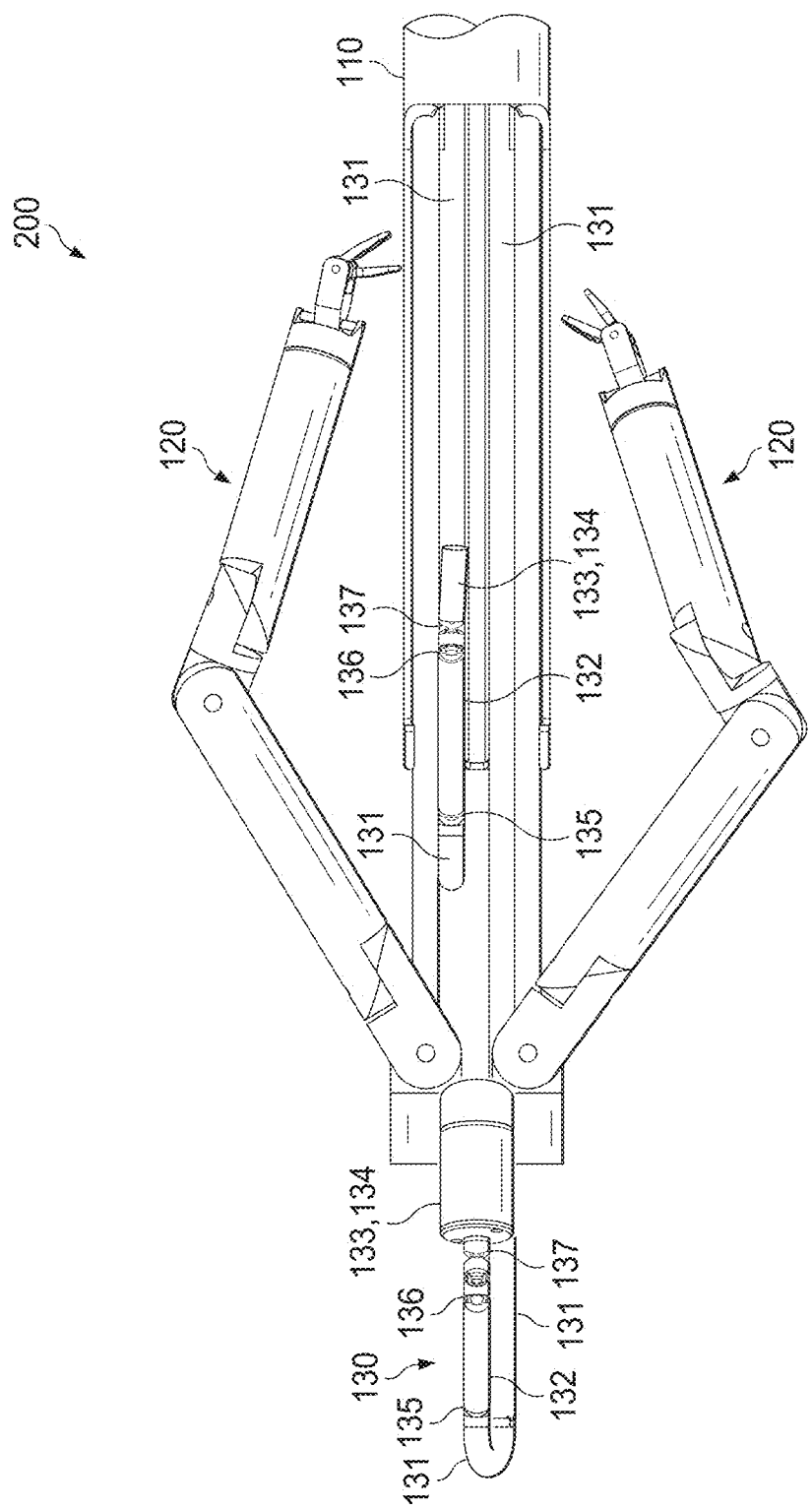
FIG. 2B is a top view of an example embodiment of a surgical system in a reverse configuration having main surgical arms, assistant surgical arms, port assembly, joint driving assembly, rotary driving assembly, and telescopic driving assembly.
Figure 2C:
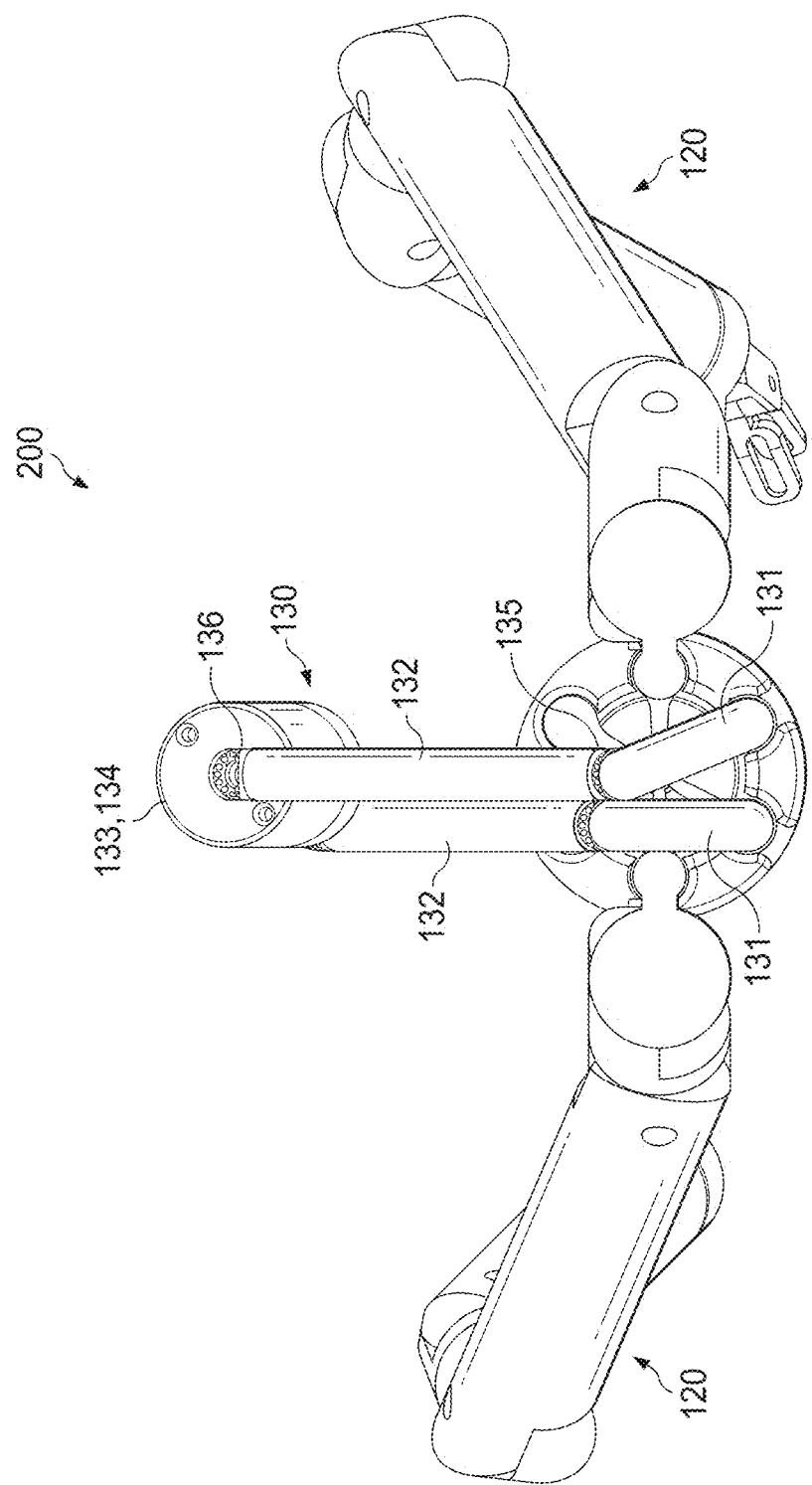
FIG. 2C is a front view of an example embodiment of a surgical system in a reverse configuration having main surgical arms, assistant surgical arms, port assembly, joint driving assembly, rotary driving assembly, and telescopic driving assembly.

FIG. 1A, FIG. 1B, and FIG. 1C illustrate an example embodiment of a surgical system (e.g., surgical system 100) configurable for use in performing, among other things, a forward-directed surgical procedure, and FIG. 2A, FIG. 2B, and FIG. 2C illustrate an example embodiment of a surgical system (e.g., surgical system 200) configurable for use in performing, among other things, a reverse-directed surgical procedure. As used in the present disclosure, references to a surgical system, surgical device, and/or one or more elements of a surgical system or device (e.g., one or more of the following elements: a port assembly, surgical arm, first segment, end effector assembly, instrument, second segment, first joint assembly, second joint assembly, end effector joint assembly, joint driving assembly, first joint driving assembly, second joint driving assembly, end effector joint driving assembly, rotary driving assembly, telescopic driving assembly, etc.) may apply to one or more example embodiments of the surgical system 100, surgical system 200, and/or one or more elements of surgical system 100 and/or surgical system 200 (e.g., one or more of the following elements: a port assembly 110, surgical arm 120, surgical arm 130, first segment 131, second segment 132, end effector assembly 133, instrument 134, first joint assembly 135, second joint assembly 136, end effector joint assembly 137, joint driving assembly 140, first joint driving assembly 142, second joint driving assembly 144, end effector joint driving assembly 146, rotary driving assembly 150, telescopic driving assembly 160, etc.) described above and in the present disclosure.

The surgical system 100 or 200 may be configurable to be inserted into a cavity of a patient (e.g., a single incision, such as an incision in or around the umbilical area) or via a natural orifice (such as a rectum or vagina, for performing natural orifice transluminal endoscopic surgery or NOTES) of the patient (collectively referred herein as an "opening").

The surgical system 100 or 200 may include a port assembly 110 (as illustrated in at least FIGS. 1A-C, 2A-C, 6A-C), which may be anchored in position in or near an opening of the patient via an external anchor (not shown). The port assembly 110 may include one or more internal channels. For example, the port assembly 110 may include a main channel 112 (as illustrated in at least FIG. 1C) for use in inserting one or more elements of the surgical system 100, such as one or more surgical arms 120 (as illustrated in at least FIGS. 1A-C, 2A-C). The port assembly 110 may also include one or more channels 114 (as illustrated in at least FIG. 1C) for use in inserting one or more other elements of the surgical system 100, such as a surgical arm 130 (as illustrated in at least FIGS. 1A-D, 2A-D, 3A-F, 5A-E, 6A-C, 7A-B, 8A-C).

The surgical system 100 or 200 may include one or more surgical arms 120 (as illustrated in at least FIGS. 1A-C). Each surgical arm 120 may be configurable in a forward configuration and/or a reverse configuration (as illustrated in at least FIGS. 2A-C). In some example embodiments, each surgical arm 120 may be a main surgical arm for use in performing primary surgical actions to an interior of a body cavity of a patient. For example, each surgical arm 120 may include a surgical instrument, such as a cutter or gripper. Such surgical instruments may be a traditional instrument, electrosurgical instrument, or the like.

The surgical system 100 or 200 may include one or more surgical arms 130 (also referred to as surgical arm assembly 130; as illustrated in at least FIGS. 1A-D, 2A-D, 3A-F, 5A-E, 6A-C, 7A-B, 8A-C). Each surgical arm 130 may be configurable in a forward configuration (as illustrated in at least FIGS. 1A-D) and/or a reverse configuration (as illustrated in at least FIGS. 2A-D, 7A-B). In some example embodiments, each surgical arm 130 may be a primary, secondary, or assistant surgical arm for use in performing primary surgical actions, secondary surgical actions, and/or assisting the surgical arm(s) 120 in performing primary surgical actions. For example, each surgical arm 130 may include a surgical instrument, such as a cutter, gripper, grasper, image capturing device, or suction device. Such surgical instruments may be a traditional instrument, detachable instrument, electrosurgical instrument, or the like.

The surgical system 100 or 200 may include a joint driving assembly 140 (as illustrated in at least FIGS. 1A, 1D, 2A, 2D, 4A-E, 6B-C). The joint driving assembly 140 may include a plurality of joint driving subassemblies, including a first joint driving subassembly 142 for driving a pivotal movement of the first joint assembly 135, second joint driving subassembly 144 for driving a pivotal movement of the second joint assembly 136, and end effector joint driving subassembly 146 for driving a pivotal movement of the end effector joint assembly 137.

The surgical system 100 or 200 may include a rotary driving assembly 150 (as illustrated in at least FIGS. 1A, 1D, 2A, 2D, 4A, 4B, 5A, 5B, 5D, 6B-C). The rotary driving assembly 150 may include a driver gear 152. The rotary driving assembly 150 may also include a driven gear 154 securable or secured to a proximal end of the first segment 131, the driven gear 154 configurable to be driven by the drive gear 152 in such a way as to rotate the surgical arm 130 (or at least the first segment 131) relative to an axis X1 formed by an elongated portion of the first segment 131.

The surgical system 100 or 200 may include a telescopic driving assembly 160 (as illustrated in at least FIGS. 1A, 1D, 2A, 2D, 6A-C). The telescopic driving assembly 160 may be securable to the port assembly 110. The telescopic driving assembly 160 may also be securable to the joint driving assembly 140 and/or rotary driving assembly 150. The telescopic driving assembly may be configurable to provide a linear displacement of the surgical arm 130 (or at least the first segment 131) in a linear direction. The linear direction may be a direction parallel to the axis X1 formed by an elongated portion of the first segment 131.

The surgical system 100 or 200 may also comprise other laparoscopic elements including, but not limited to, one or more other surgical arms, one or more other image capturing devices, one or more suction tubes, etc. Although FIGS. 1B-C illustrate surgical system 100 having two surgical arms 120, a retractor surgical arm 130a, an image capturing surgical arm 130b, a suction surgical arm 130c, and a port assembly 110, it is to be understood in the present disclosure that example embodiments may include more or less than two surgical arms 120, more or less than one retractor surgical arm 130a, more or less than one image capturing surgical arm 130b, more or less than one suction surgical arm 130c, and more or less than one port assembly 110 without departing from the teachings of the present disclosure.

These and other elements and example embodiments of the surgical system 100 or 200 will now be further described with reference to the accompanying figures.

The Surgical Arm (e.g., Surgical Arm Assembly 130, 130a, 130b, 130c).

In an example embodiment, the surgical system 100 or 200 may include one or more surgical arms or surgical arm assemblies (e.g., surgical arms 130, 130a, 130b, and/or 130c) (hereinafter surgical arm 130), such as those illustrated in at least FIGS. 1A-D, 2A-D, 3A-F, 5A-E, 6A-C, 7A-B, 8A-C. Each surgical arm may be configurable to secure to and unsecure from the port assembly 110.

One or more of the surgical arms 130 may include a configurable serial (or linear) arrangement of a plurality of segments and joints. For example, as illustrated in at least FIGS. 1A-D, 2A-D, and 3A-H, one or more of the surgical arms 130 may include a first segment 131, second segment, 132, end effector assembly 133 having an instrument 134, first joint assembly 135, second joint assembly 136, and/or end effector joint assembly 137. The surgical arm 130 may also include one or more other segments and/or joint assemblies, such as a third joint assembly 138 provided between second joint assembly 136 and end effector joint assembly 137 (as illustrated in at least FIGS. 1A, 1D, 3A-D, and 8B) and/or a fourth joint assembly 139 provided between the first joint assembly 135 and second segment 132 (as illustrated in at least FIG. 7A). It is to be understood that the surgical arm 130 may include more and/or different segments and/or joints, more and/or different segment and/or joint configurations, and more and/or different segment and/or joint arrangements than those described above and in the present disclosure without departing from the teachings of the present disclosure.

These and other elements and example embodiments of the surgical arm 130 will now be further described with reference to the accompanying figures.

(i) First Segment (e.g., First Segment 131).

In an example embodiment, the surgical arm 130 may include one or more first segments 131. The first segment 131 may include at least an elongated or linear portion having a proximal end in communication with (e.g., in contact with, attached to, secured to, driven by, etc.) the joint driving assembly 140, rotary driving assembly 150, and telescopic driving assembly 160. The elongated portion of the first segment 131 may also be in communication with the port assembly 110 when the surgical arm 130 is inserted into the port assembly 110 and positioned and configured to perform a surgical action. The first segment 131 may also include a curved or substantially U-shaped section connected to a distal end of the elongated portion of the first segment 131, as illustrated in at least FIGS. 2A-D and FIGS. 7A-B. It is to be understood that the curved or substantially U-shaped section may be in any shape or form so long as it provides for a reverse configuration, as described above and in the present disclosure. It is also to be understood that the curved or U-shaped section and the elongated portion of the first segment 131 may be formed as separate elements connected together or as a unitary body without departing from the teachings of the present disclosure.

The first segment 131 may also include a plurality of channels. For example, the first segment 131 may include a main channel 131*d* (as illustrated in at least FIG. 3E). In example embodiments where the surgical arm 130 includes a suction/irrigation device 134 as the instrument 134 of the end effector assembly 133, such main channel 131*d* may be for use in providing the suction or negative pressure to the suction/irrigation device 134. The first segment 131 may also include a plurality of channels, such as channels 131*a*, 131*b*, and/or 131*c* and channels 131*a*', 131*b*', and/or 131*c*' that may be provided opposite to channels 131*a*, 131*b*, and 131*c* (as illustrated in at least FIG. 3F). In an example embodiment, channels 131*a*, 131*b*, and 131*c* may be provided and/or run within a first sidewall (or first sidewall section) of the first segment 131 and channels 131*a*', 131*b*', and 131*c*' may be provided and/or run within a second or opposite facing sidewall (or second or opposite facing sidewall section) of the first segment 131. For example, channels 131*a* and 131*c*' may be positioned in such a way that a line or plane drawn through the channels 131*a* and 131*c*' would intersect a center axis X1 (as illustrated in at least FIGS. 1D and 3E) formed by the elongated portion of the first segment 131. Similarly, channels 131*b* and 131*b*' may be positioned in such a way that a line or plane drawn through the channels 131*b* and 131*b*' would intersect the center axis X1 formed by the elongated portion of the first segment 131. Similarly, channels 131*c* and 131*a*' may be positioned in such a way that a line or plane drawn through the channels 131*c* and 131*a*' would intersect the center axis X1 formed by the elongated portion of the first segment 131. It is to be understood in the present disclosure that the first segment 131 may also include other channels (or less channels) formed or run within the sidewall(s) of the first segment 131.

In an example embodiment, a cross-section of the first segment 131 may be formed in a substantially circular shape. Put differently, the first segment 131 may be substantially cylindrical in shape. However, it is to be understood that the first segment 131 (and/or its cross-section) may be formed in one or more other shapes and forms without departing from the teachings of the present disclosure. When the first segment 131 includes a substantially circular cross-section, a diameter of the first segment 131 may be between about 5 to 8 mm. Furthermore, the main channel 131*d* (if provided) may have a diameter of between about 2 to 4 mm. Furthermore, each of the channels 131*a*, 131*a*', 131*b*, 131*b*', 131*c*, and 131*c*' (and/or other channels, if provided) may have a diameter of between about 0.5 to 1.2 mm. In an example embodiment, the first segment 131 may have a length between about 500 to 800 mm. The first segment 131 may be formed using one or more of a plurality of materials and compositions, such as surgical-grade metals, high-strength aluminum alloys, stainless steel (such as 304/304 L, 316/316 L, and 420), pure titanium, titanium alloys (such as Ti6Al4V, NiTi), and cobalt-chromium alloys. It is to be understood in the present disclosure that other materials may also be used without departing from the teachings of the present disclosure.

(ii) Second Segment (e.g., Second Segment 132).

In an example embodiment, the surgical arm 130 may include one or more second segments 132. The second segment 132 may include at least an elongated linear portion having a proximal end pivotally coupled to a distal end of the first segment 131 via the first joint assembly 135. A distal end of the second segment 132 may be pivotally coupled to a proximal end of the end effector assembly 133. The second segment 132 may also include a plurality of channels. For example, the second segment 132 may include a main channel 132*d* (as illustrated in at least FIG. 3E). In example embodiments where the surgical arm 130 includes a suction/irrigation device 134 as the instrument 134 of the end effector assembly 133, such main channel 132*d* may be for use in providing the suction or negative pressure to the suction/irrigation device 133. The second segment 132 may also include a plurality of channels, such as channels 132*a* and/or 132*b* and channels 132*a*' and/or 132*b*' that are provided opposite to channels 132*a* and 132*b* (as illustrated in at least FIG. 3F and FIG. 3G). In some example embodiments, the second segment 132 may also include a channel 132*c* and channel 132*c*' opposite to channel 132*c*. In an example embodiment, channels 132*a* and 132*b* (and 132*c* if provided) may be provided and/or run within a first sidewall (or first sidewall section) of the second segment 132 and channels 132*a*' and 132*b*' (and 132*c*' if provided) may be provided and/or run within a second or opposite facing sidewall (or second or opposite facing sidewall section) of the second segment 132. For example, channels 132*a* and 132*c*' (if provided) may be positioned in such a way that a line or plane drawn through the channels 132*a* and 132*c*' would intersect a center axis X2 (as illustrated in at least FIGS. 1D and 3E) formed by the elongated portion of the second segment 132. Similarly, channels 132*b* and 132*b*' may be positioned in such a way that a line or plane drawn through the channels 132*b* and 132*b*' would intersect the center axis X2 formed by the elongated portion of the second segment 132. Similarly, channels 132*c* (if provided) and 132*a*' may be positioned in such a way that a line or plane drawn through the channels 132*c* and 132*a*' would intersect the center axis X2 formed by the elongated portion of the second segment 132. It is to be understood in the present disclosure that the second segment 132 may also include other channels formed or run within the sidewall(s) of the second segment 132. The positioning of the channels 132*a*, 132*b*, 132*c* (if provided), 132*a*', 132*b*', and 132*c*' (if provided) may be positioned in such a way that, when the first segment 131 and second segment 132 are configured to align in a substantially straight line (e.g., when axis X1 and axis X2 are parallel to one another), such channels of the second segment 132 are substantially aligned with channels 131*a*, 131*b*, 131*c* (if 132*c* is provided), 131*a*', 131*b*', and 131*c*' (if 132*c*' is provided), respectively, of the first segment 131.

In an example embodiment, a cross-section of the second segment 132 may be formed in a substantially circular shape. Put differently, the second segment 132 may be substantially cylindrical in shape. However, it is to be understood that the second segment 132 (and/or its cross-section) may be formed in one or more other shapes and forms without departing from the teachings of the present disclosure. For second segment 132 having a substantially circular cross-section, a diameter of the second segment 132 may be between about 5 to 8 mm. Furthermore, the main channel 132*d* (if provided) may have a diameter of between about 2 to 4 mm. Furthermore, each of the channels 132*a*, 132*a*', 132*b*, 132*b*', 132*c* (if provided), and 132*c*' (if provided) (and/or other channels, if provided) may have a diameter of between about 0.5 to 1.2 mm. In an example embodiment, the second segment 132 may have a length between about 25 to 70 mm. The second segment 132 may be formed using one or more of a plurality of materials and compositions, such as surgical-grade metals, high-strength aluminum alloys, stainless steel (such as 304/304 L, 316/316 L, and 420), pure titanium, titanium alloys (such as Ti6Al4V, NiTi), and cobalt-chromium alloys. It is to be understood in the present disclosure that other materials may also be used without departing from the teachings of the present disclosure.

(iii) End Effector Assembly (e.g., End Effector Assembly 133).

In an example embodiment, the surgical arm 130 may include an end effector assembly 133. The end effector assembly 133 may include at least an elongated linear portion having a proximal end pivotally coupled to a distal end of the second joint assembly 136 via the end effector joint assembly 137. A distal end of the end effector assembly 133 may include an instrument 134, such as a cutter 134, grasper 134, retractor 134 (as illustrated in at least FIG. 8A), image capturing device 134 (as illustrated in at least FIG. 8B), and/or suction/irrigation device 134 (as illustrated in at least FIG. 8C). The end effector assembly 133 may also include a plurality of channels. For example, the end effector assembly 133 may include a main channel 133d (as illustrated in at least FIG. 3E). In example embodiments where the arm assembly 130 includes a suction/irrigation device 134 as the instrument 134 of the end effector assembly 133, such main channel 133d may be for use in providing the suction or negative pressure to the suction/irrigation device 134. The end effector assembly 133 may also include a plurality of channels, such as channel 133a and channel 133a' opposite to channels 133a (as illustrated in at least FIG. 3H). In an example embodiment, channel 133a may be provided and/or run within a first sidewall (or first sidewall section) of the end effector assembly 133 and channel 133a' may be provided and/or run within a second or opposite facing sidewall (or second or opposite facing sidewall section) of the end effector assembly 133. For example, channel 133a and 133a' may be positioned in such a way that a line or plane drawn through the channels 133a and 133a' would intersect a center axis X3 (as illustrated in at least FIGS. 1D and 3E) formed by a portion of the end effector assembly 133. It is to be understood in the present disclosure that the end effector assembly 133 may also include other channels (or less channels) formed or run within the sidewall(s) of the end effector assembly 133. The positioning of the channels 133a and 133a' may be positioned in such a way that, when the second segment 132 and end effector assembly 133 are configured to align in a substantially straight line (e.g., when axis X2 and axis X3 are parallel to one another), such channels of the end effector assembly 133 are substantially aligned with channels 132a and 132a', respectively, of the second segment 132.

In an example embodiment, a cross-section of at least a proximal portion of end effector assembly 133 may be formed in a substantially circular shape. Put differently, such proximal portion may be substantially cylindrical in shape. However, it is to be understood that such proximal portion of the end effector assembly 133 may be formed in one or more other shapes and forms without departing from the teachings of the present disclosure. For end effector assembly 133 having a substantially circular cross-section, a diameter of the end effector assembly 133 may be between about 5 to 8 mm. Furthermore, the main channel 133d (if provided) may have a diameter of between about 2 to 4.5 mm. Furthermore, each of the channels 133a and 133a' (and/or other channels, if provided) may have a diameter of between about 0.5 to 1.2 mm. In an example embodiment, when the instrument 134 is a cutter 134, grasper 134, or retractor 134, the end effector assembly 133 may have an overall length between about 40 to 60 mm. When the instrument 134 is an image capturing device 134 (which may include a still image capturing device, video capturing device, 3-D stereoscopic or autostereoscopic device, etc.), the end effector assembly 133 may have an overall length between about 25 to 35 mm. When the instrument 134 is suction/irrigation device 134, the end effector assembly 133 may have an overall length between about 40 to 70 mm. The end effector assembly 133 may be formed using one or more of a plurality of materials and compositions, such as surgical-grade metals, high-strength aluminum alloys, stainless steel (such as 304/304 L, 316/316 L, and 420), pure titanium, titanium alloys (such as Ti6Al4V, NiTi), and cobalt-chromium alloys. It is to be understood in the present disclosure that other materials may also be used without departing from the teachings of the present disclosure.

The instrument 134 and/or one or more other parts of the surgical arm 130 may include integrated haptic and/or force feedback subsystems (not shown) configurable to provide to a haptic feedback response to a user interface (e.g., a user interface for use by a surgeon or assistant), and such haptic feedback response may be first processed by a controller (not shown). The instrument 134 may also be configurable to provide the controller and/or user interface (e.g., user interface 910) with one or more of a plurality of feedback responses and/or measurements, including those pertaining to position (including orientation), applied force, proximity, temperature, pressure, humidity, etc., of, by, and/or nearby to the instrument 134. In addition to the haptic feedback response, the controller may be further configurable to, among other things, translate, replicate, map, and/or sense the delicate movements of the operator using the user interface into movements of the surgical arm 130 with high precision, high dexterity, and minimum burden.

The surgical arm 130 may also be configurable to receive an electric current (or voltage potential, thermal energy, heat, cold temperature application, etc.) from an energy source (or other source, not shown). In example embodiments, such an energy source (or other source) may also be integrated, in part or in whole, into one or more of the surgical arms 130. The electrical current (or voltage potential, thermal energy, heat, or cold temperature application) from the energy source (or other source) may be selectively applied to one or more elements of the end-effector assembly 133, and such selective application of the electric current (or voltage potential, thermal energy, heat, cold temperature application, etc.) may be configured and/or controlled by the user interface (e.g., via the controller). For example, in situations wherein the end-effector assembly 133 includes instrument 134, an operator of the user interface may configure the user interface to command (e.g., via the controller) the energy source (or other source) to apply the electric current (or voltage potential, thermal energy, heat, cold temperature application, etc.) to the instrument 134. It is recognized in the present disclosure that the application of such electric current (or voltage potential, thermal energy, heat, cold temperature application, etc.) to the instrument 134 enables the end-effector assembly 133 to perform the actions of an electrosurgical instrument, or the like.

(iv) First Joint Assembly (e.g., First Joint Assembly 135).

In an example embodiment, the surgical arm 130 may include a first joint assembly 135. The first joint assembly 135 may be configurable to pivotally couple, connect, attach, communicate, and/or secure (hereinafter "secure" or "couple") a distal end of the first segment 131 to a proximal end of the second segment 132. For example, the first joint assembly 135 may include a proximal end securable or secured to a distal end of the first segment 131. The first joint assembly 135 may also include a distal end securable or secured to a proximal end of the second segment 132. The first joint assembly 135 may also include a joint securing the proximal end and distal end of the first joint assembly 135. In some example embodiments, the joint of the first joint assembly 135 may include an elongated portion, such as a pin or rod, forming an axis that is substantially perpendicular to axis X1 and/or axis X2 irrespective of the position of the second segment 132 relative to the first segment 131.

Figure 9:
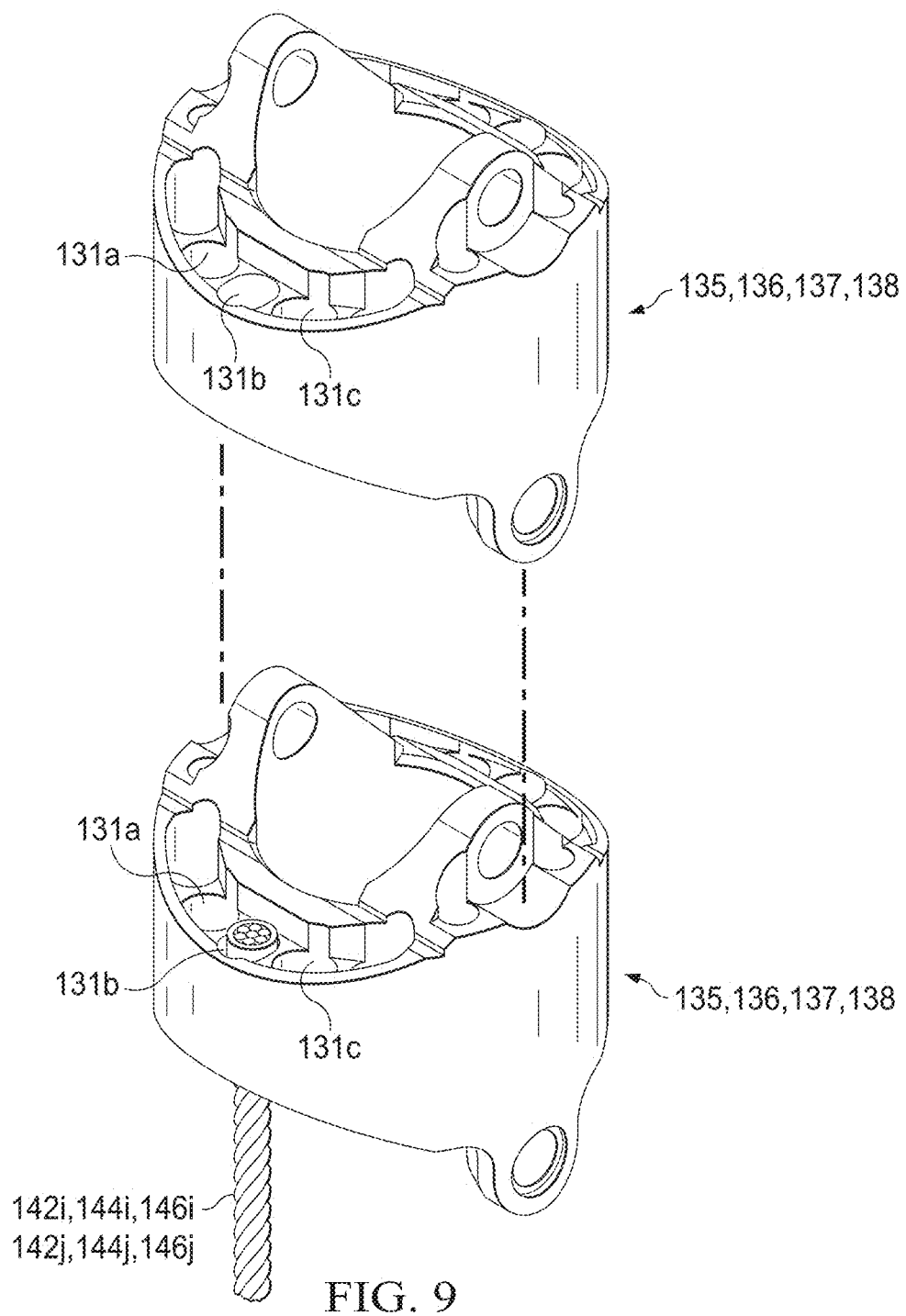
FIG. 9 is a perspective view of an example embodiment of a portion of a joint assembly, a cable, and a termination point.
Figure 10A:
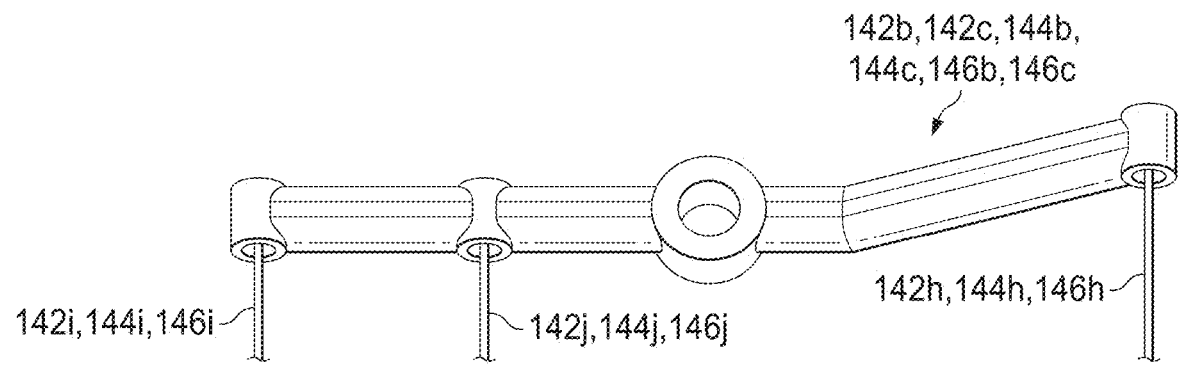
FIG. 10A is a perspective view of an example embodiment of a lever.
Figure 10B:
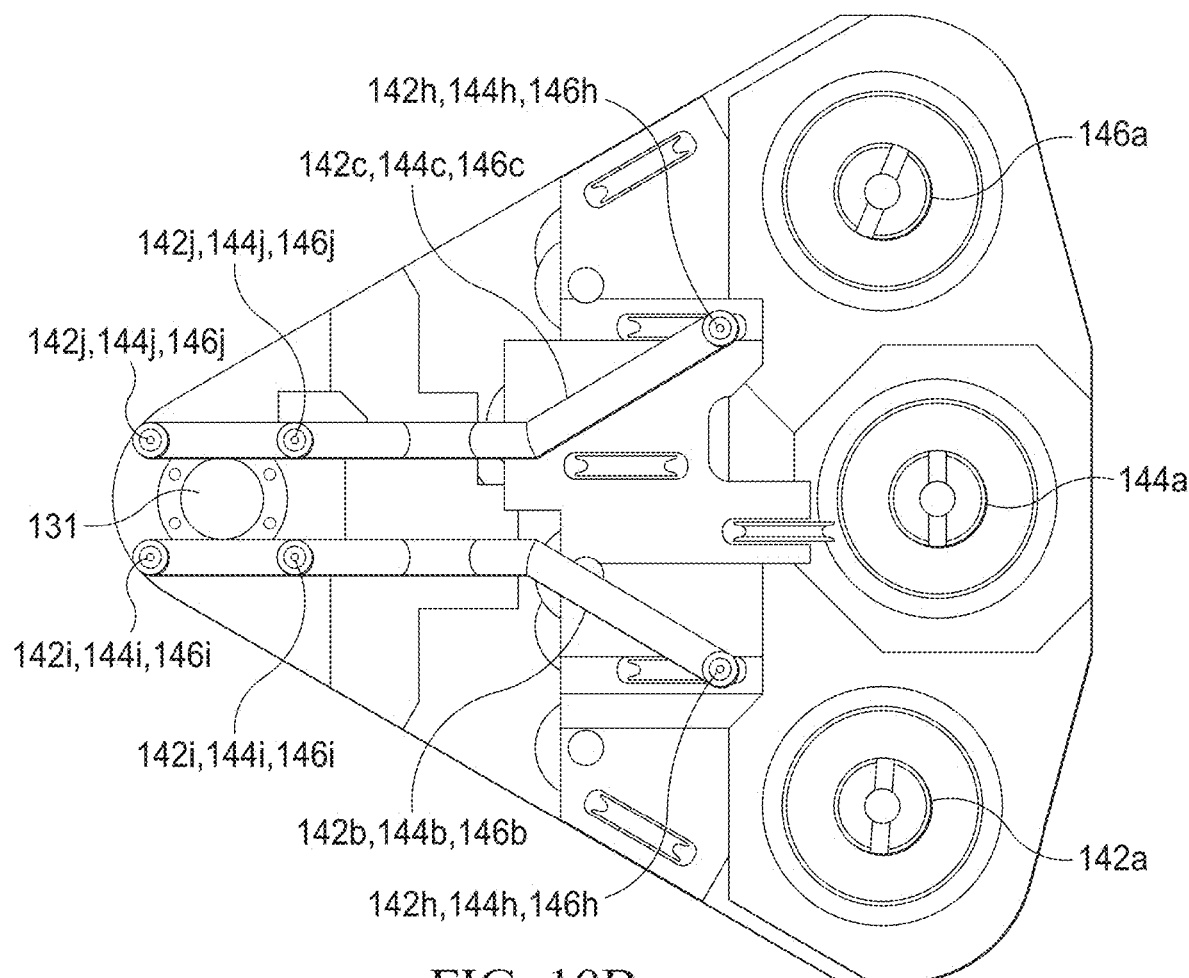
FIG. 10B is a top view of an example embodiment of the joint driving assembly.

The first joint assembly 135 may also include a plurality of channels, holes, or the like. For example, the first joint assembly 135 may include one or more main channels on each of the proximal end and distal end of the first joint assembly 135. The proximal end of the first joint assembly 135 may also include a plurality of channels (or a single channel or opening), and such channels may be positioned in such a way as to positionally correspond to one or more of the channels 131a, 131b, 131c, 131a', 131b', and 131c' of the first segment 131. The distal end of the first joint assembly 135 may include a plurality of channels (or a single channel or opening), and such channels may be positioned in such a way as to positionally correspond to one or more channels of the proximal end of the first joint assembly 135 when the proximal end and distal end of the first joint assembly 135 are aligned (e.g., aligned in a straight line or having their center axis lined in a straight line). Furthermore, the plurality of channels (or a single channel or opening) of the distal end of the first joint assembly 135 may be positioned in such a way as to positionally correspond to one or more of the channels 132a, 132b, 132c (if provided), 132a', 132b', and 132c' (if provided) of the second segment 132. FIG. 9 illustrates an example embodiment of a proximal or distal end of the first joint assembly 135 having a plurality of channels for use in housing, guiding, directing, etc. one or more cables (e.g., first joint driving cables 142i or 142j, second joint driving cables 144i or 144j, end effector joint driving cables 146i or 146j, etc., as will be further described in the present disclosure).

In an example embodiment, a cross-section of a portion of the proximal and distal ends of the first joint assembly 135 may be formed in a substantially circular shape. Put differently, the proximal and distal ends of the first joint assembly 135 may be substantially cylindrical in shape. However, it is to be understood that the cross-section of the proximal and distal ends of the first joint assembly 135 may be formed in one or more other shapes and forms without departing from the teachings of the present disclosure. For proximal and distal ends of the first joint assembly 135 having a substantially circular cross-section, a diameter of the proximal and distal ends of the first joint assembly 135 may be between about 5 to 8 mm. Furthermore, each main channel of the first joint assembly 135 may have a diameter of between about 0.5 to 1.2 mm. Furthermore, one or more of the channels of the first joint assembly 135 that positionally correspond to channels 131a, 131b, 131c, 131a', 131b', 131c', 132a, 132a', 132b, 132b', 132c (if provided), and 132c' (if provided) may have a diameter of between about 0.5 to 1.2 mm. In an example embodiment, the first joint assembly 135 may have a length between about 3 to 10 mm when the proximal and distal ends of the first joint assembly 135 are aligned in a straight line. The first joint assembly 135 may be formed using one or more of a plurality of materials and compositions, such as surgical-grade metals, high-strength aluminum alloys, stainless steel (such as 304/304 L, 316/316 L, and 420), pure titanium, titanium alloys (such as Ti6Al4V, NiTi), and cobalt-chromium alloys. It is to be understood in the present disclosure that other materials may also be used without departing from the teachings of the present disclosure.

Figure 3A:
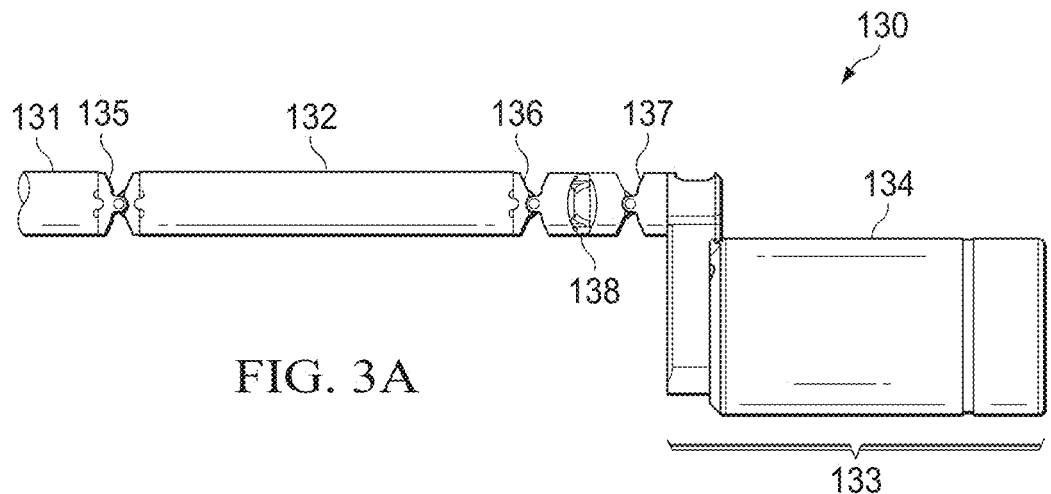
FIGS. 3A-D are side views of an example embodiment of a surgical system configured in various different positions.
Figure 3B:
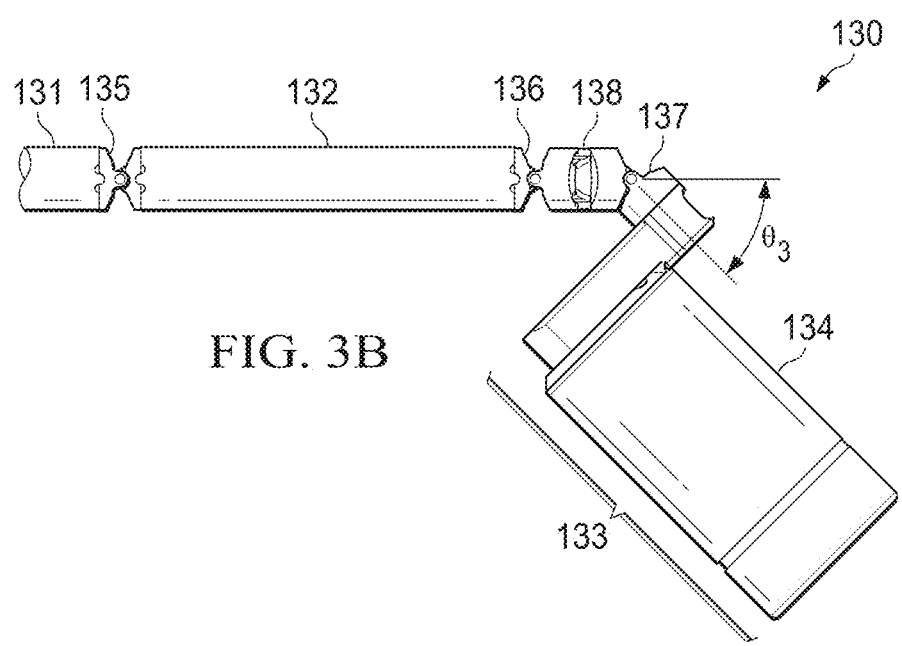
Figure 3C:
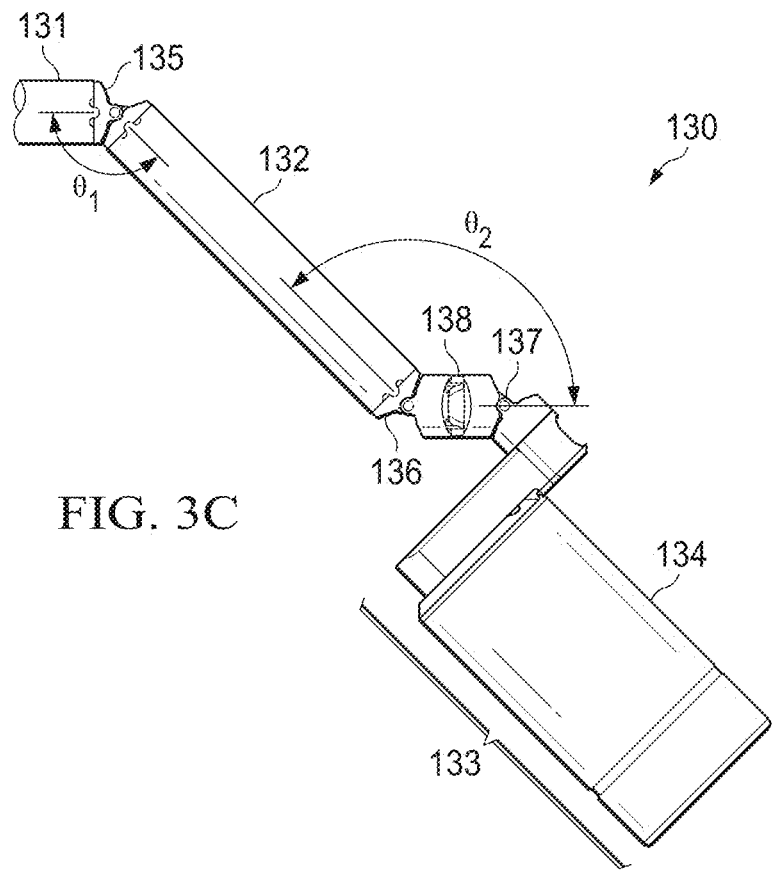
Figure 3D:
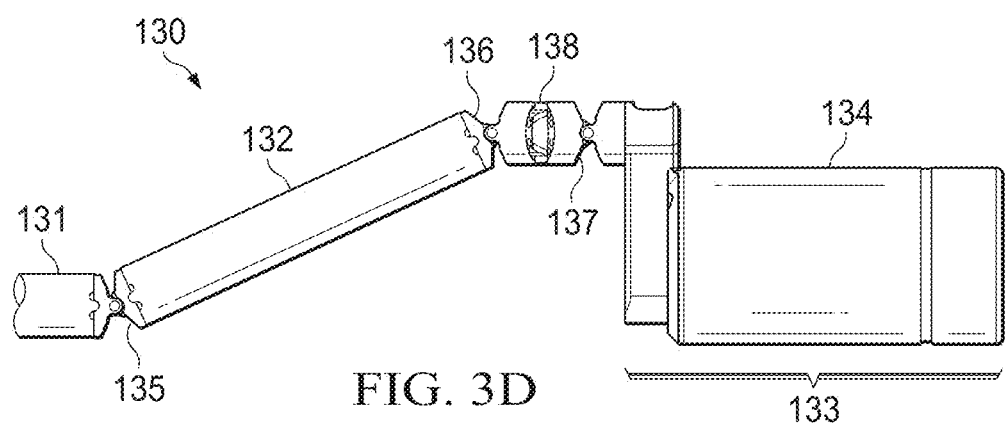
Figure 3E:
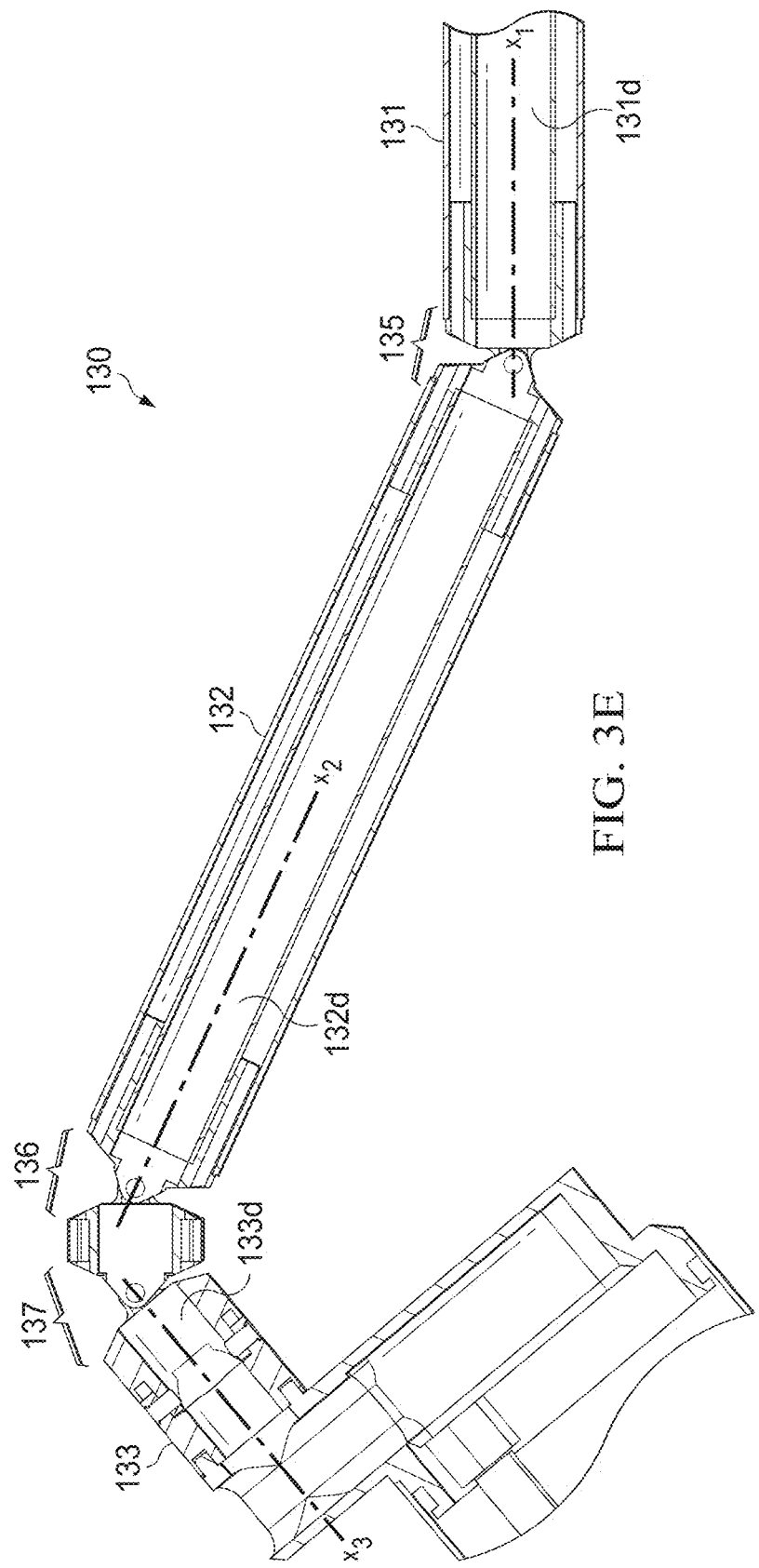
FIG. 3E is a cross-sectional side view of an example embodiment of a surgical system.
Figure 3F:
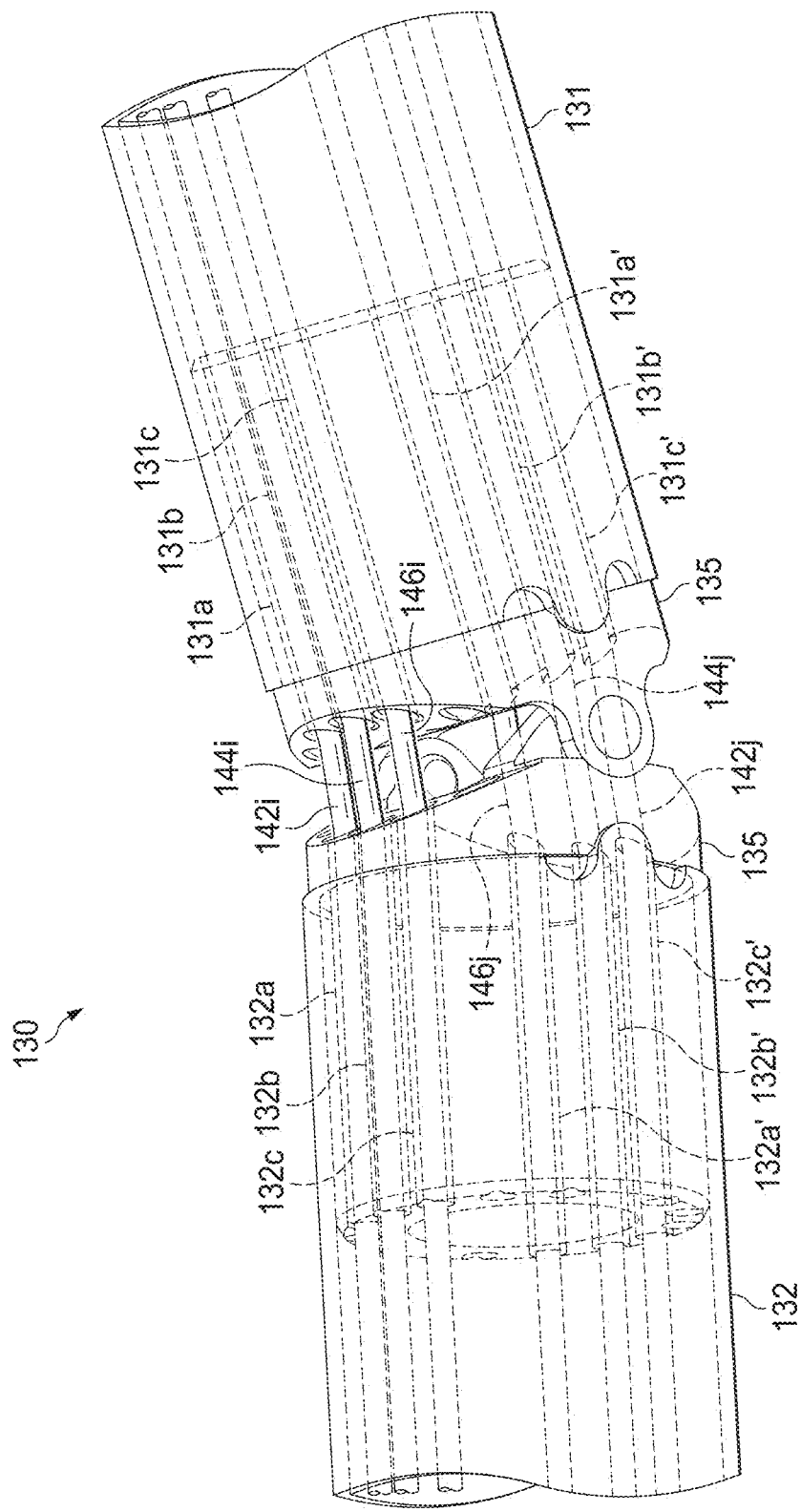
FIG. 3F is a perspective view of an example embodiment of a surgical system having a first segment, first joint assembly, and second segment.
Figure 3G:
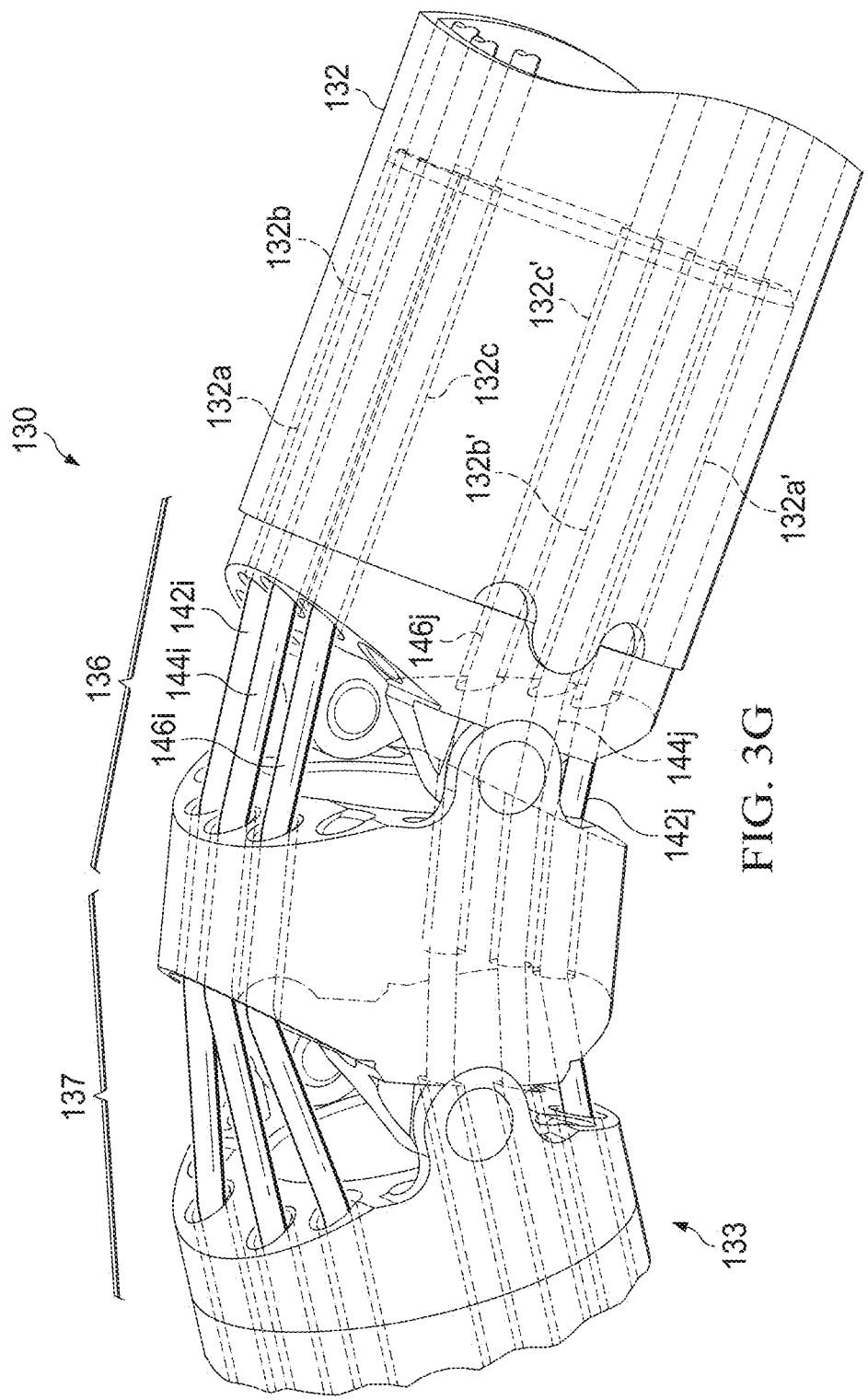
FIG. 3G is a perspective view of an example embodiment of a surgical system having a second segment, second joint assembly, and end effector joint assembly.
Figure 3H:
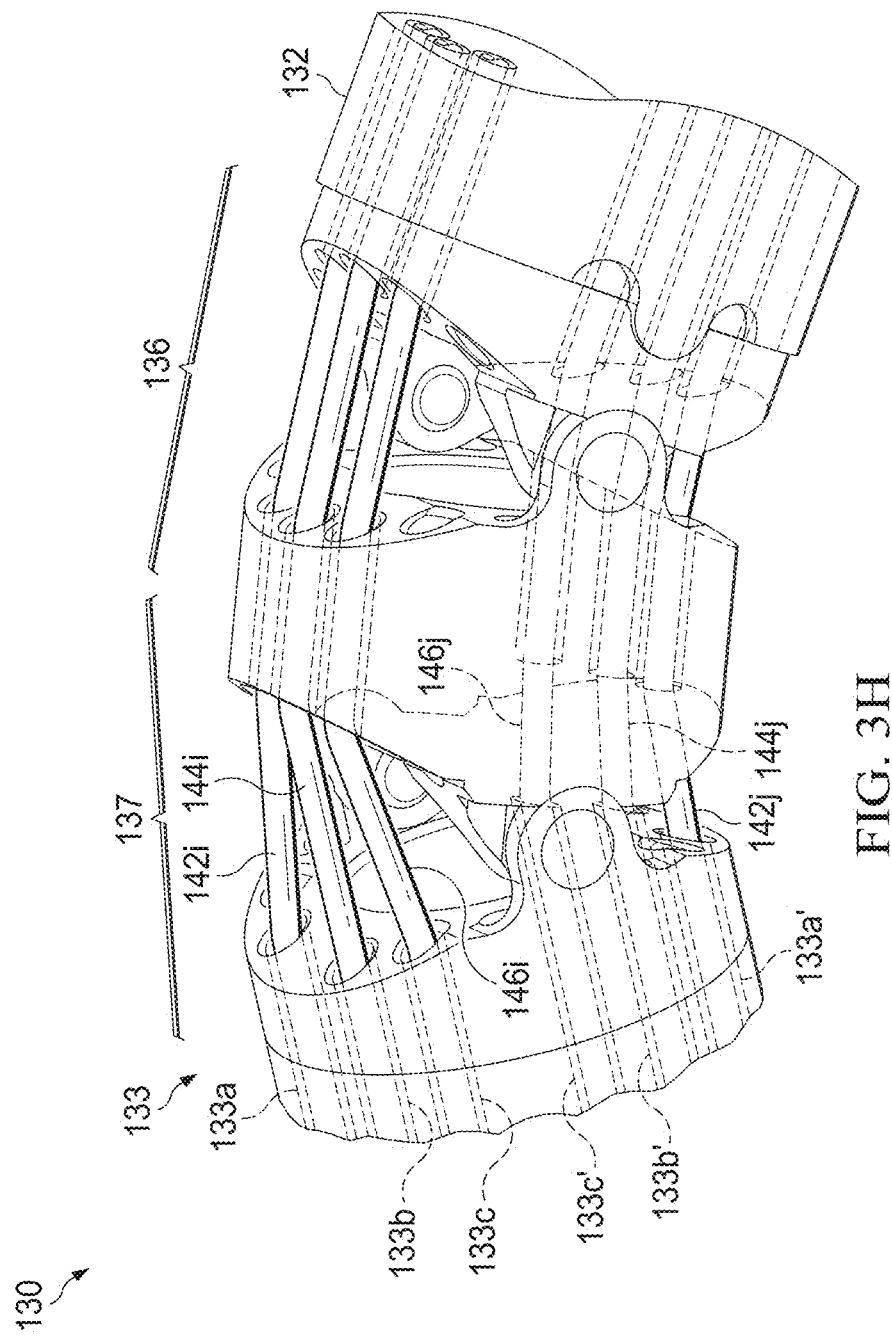
Figure 4A:
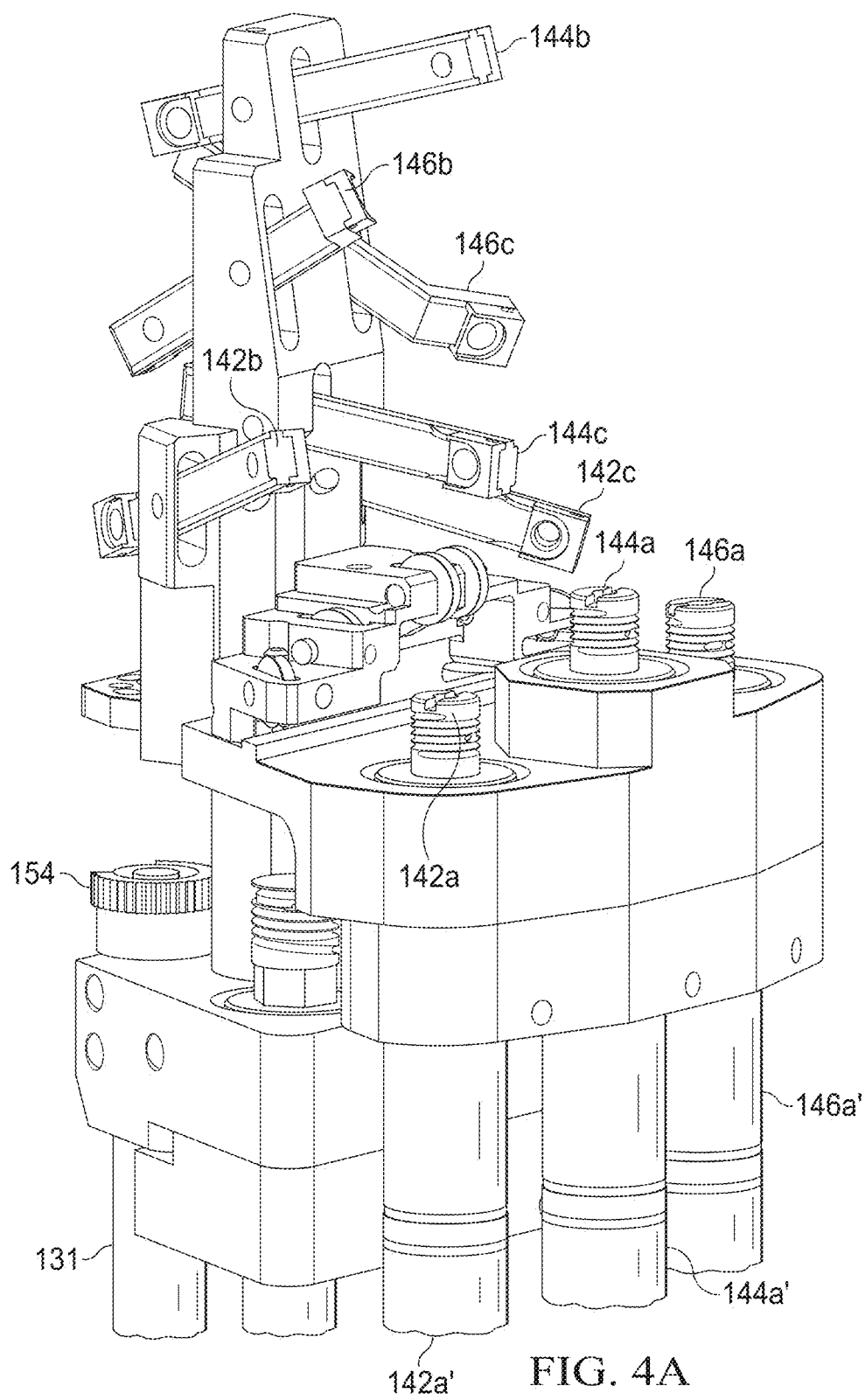
FIG. 4A is a perspective view of an example embodiment of a surgical system having a joint driving assembly.
Figure 4B:
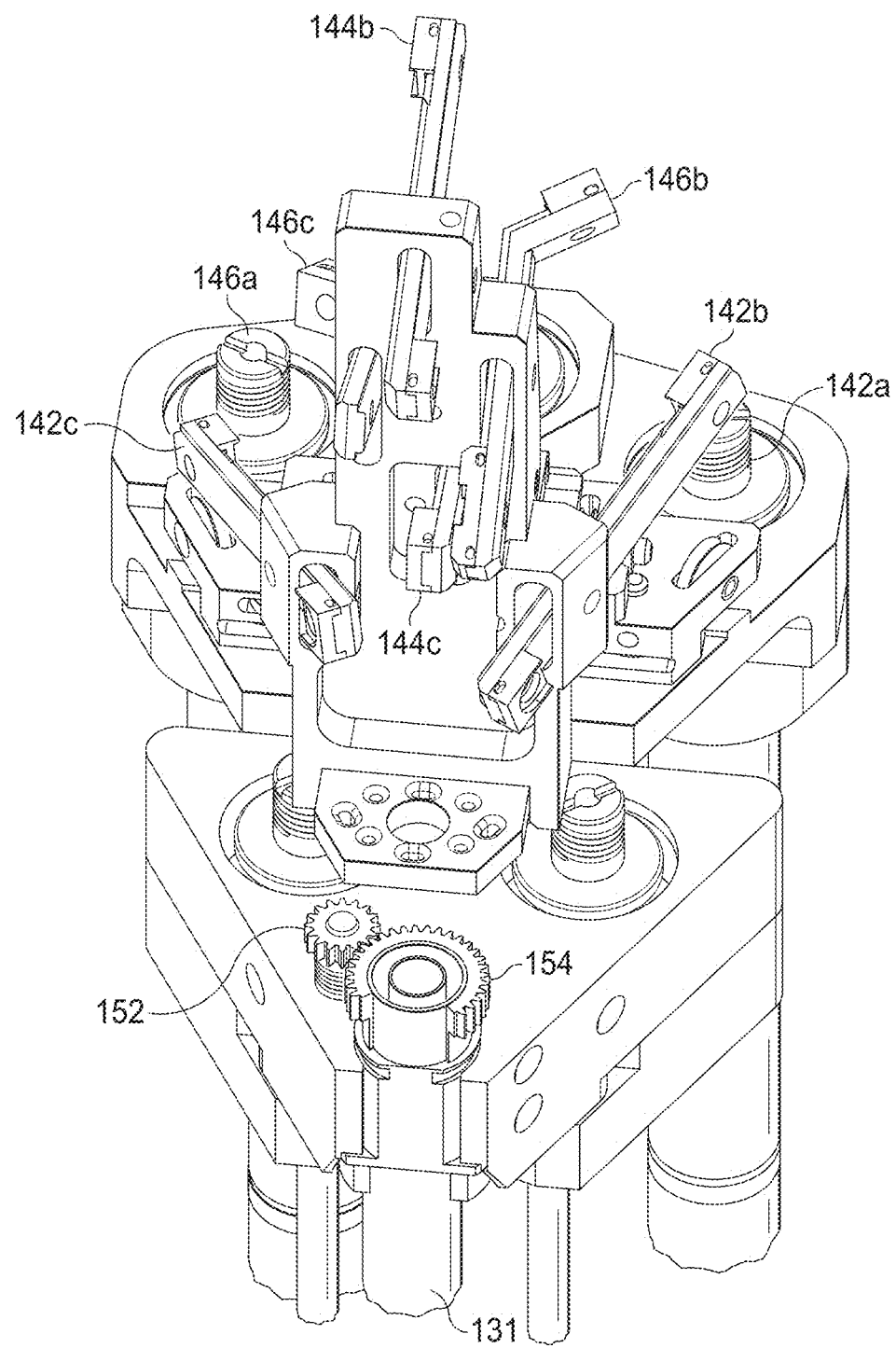
FIG. 4B is a perspective view of an example embodiment of a surgical system having a joint driving assembly.
Figure 4C:
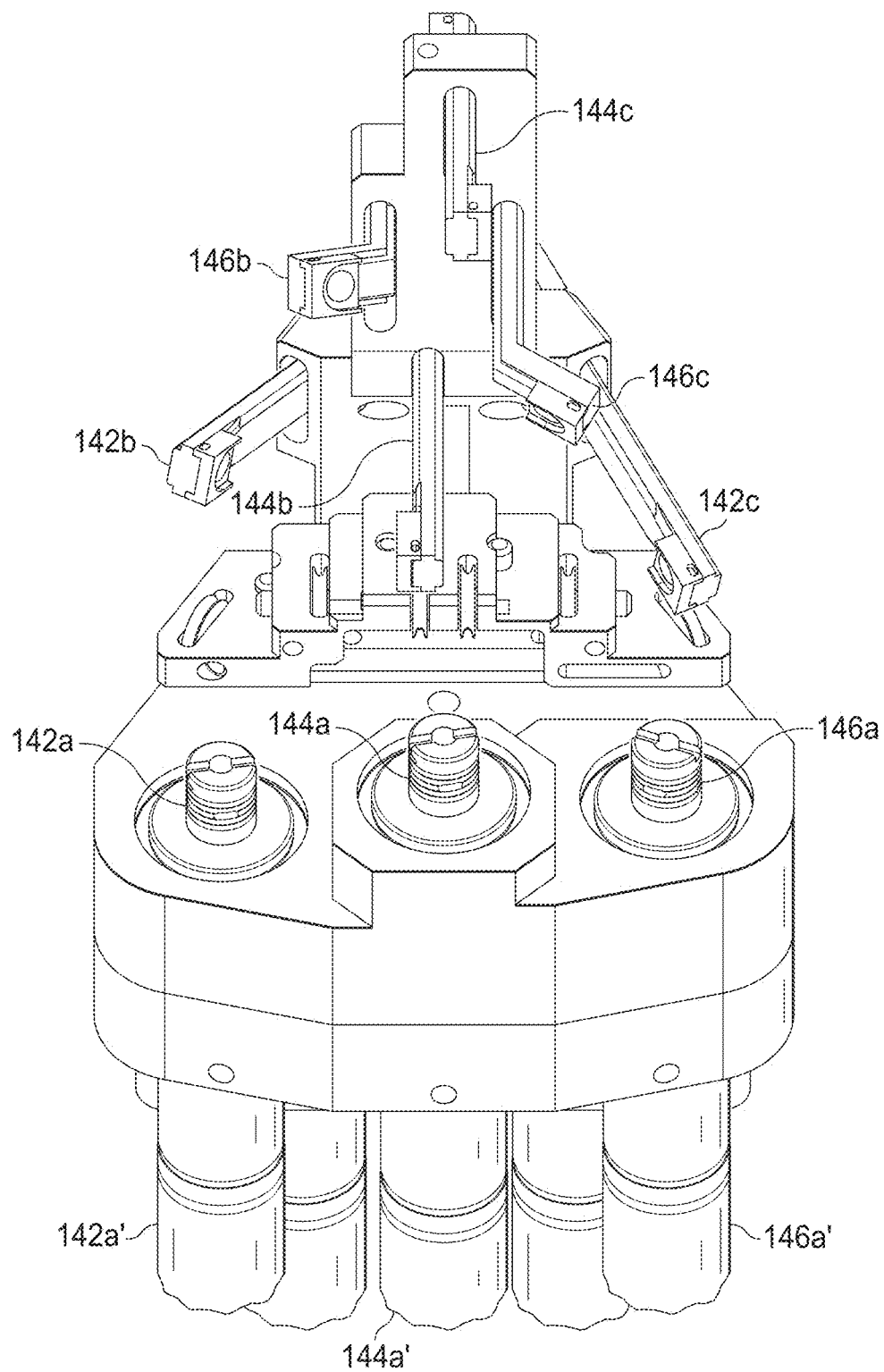
FIG. 4C is a perspective view of an example embodiment of a surgical system having a joint driving assembly.
Figure 4D:
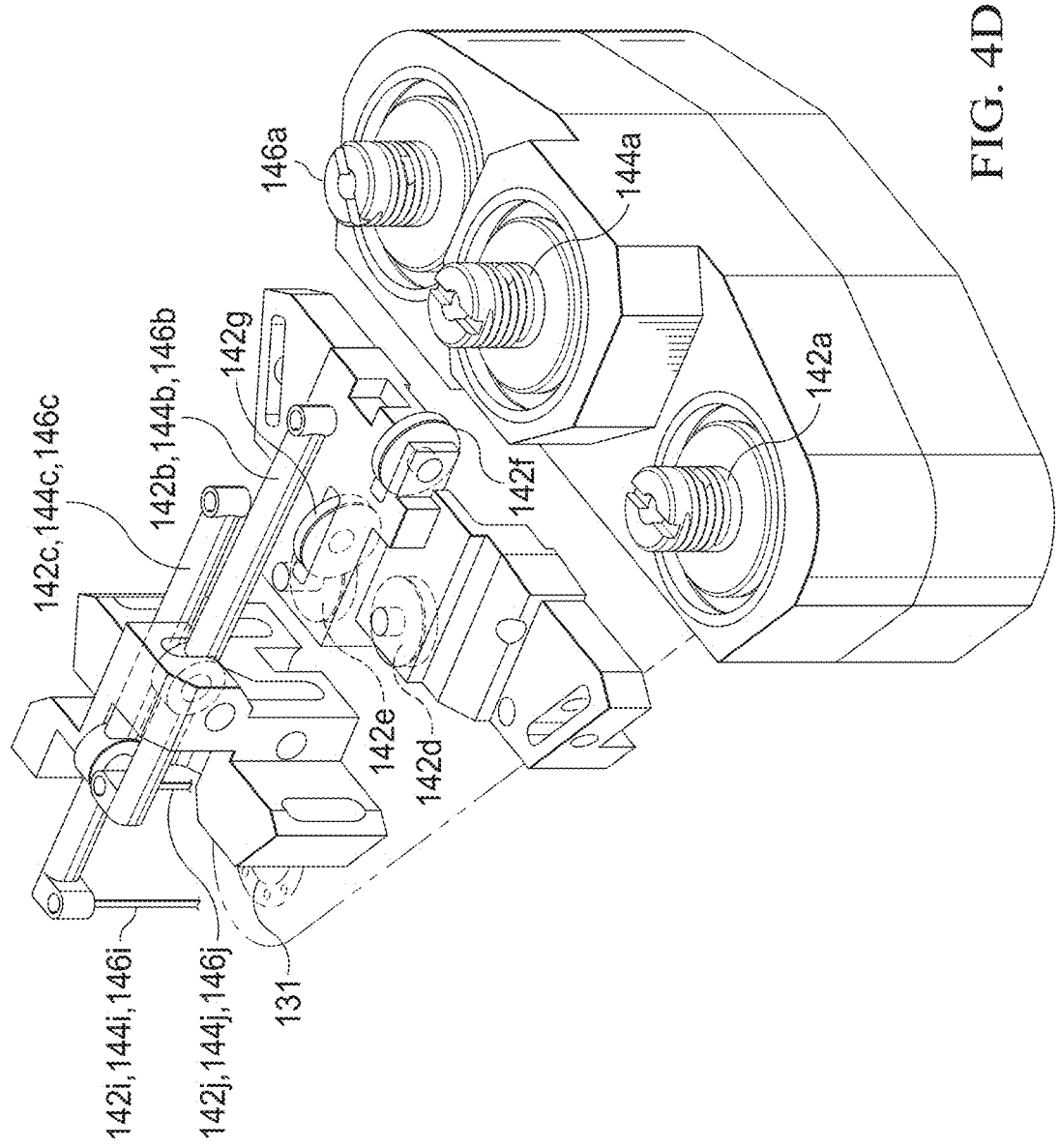
FIG. 4D is a perspective view of an example embodiment of elements of the joint driving assembly, including elements of the first joint driving assembly.
Figure 4E:
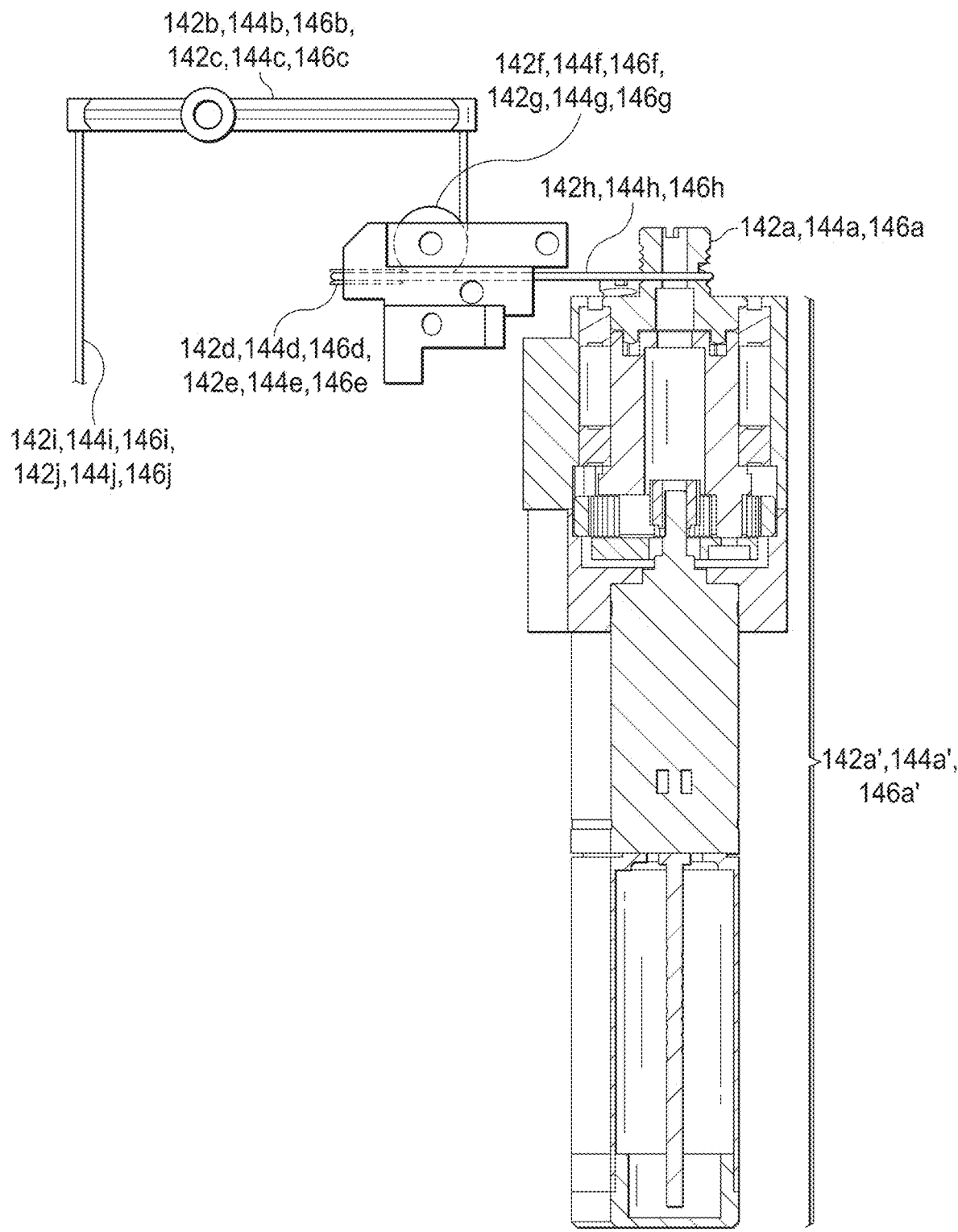
FIG. 4E is a cross-sectional view of an example embodiment of elements of the joint driving assembly, including elements of the first joint driving assembly.
Figure 4F:
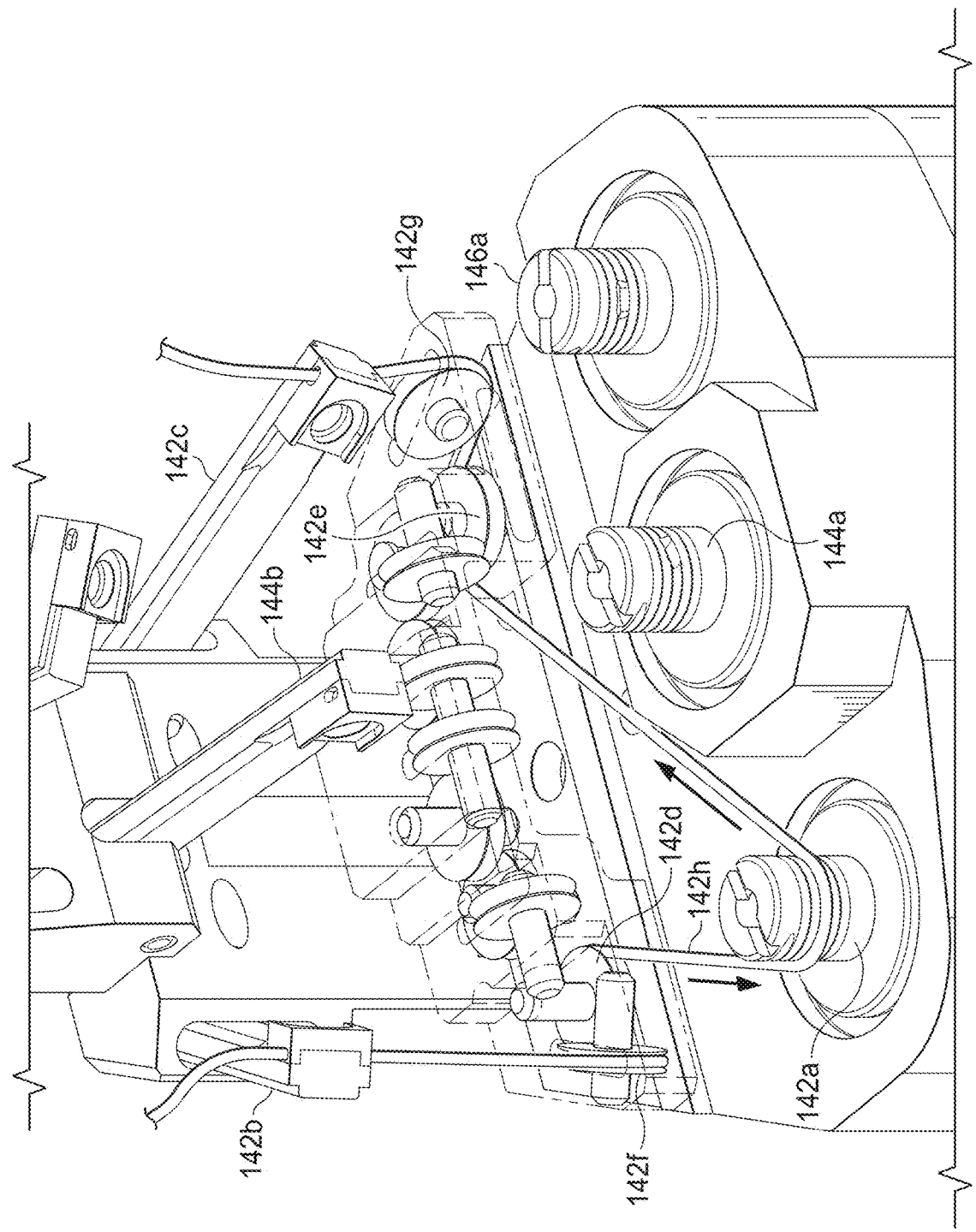
FIGS. 4F-G are other perspective views of an example embodiment of certain elements of the joint driving assembly.
Figure 4G:
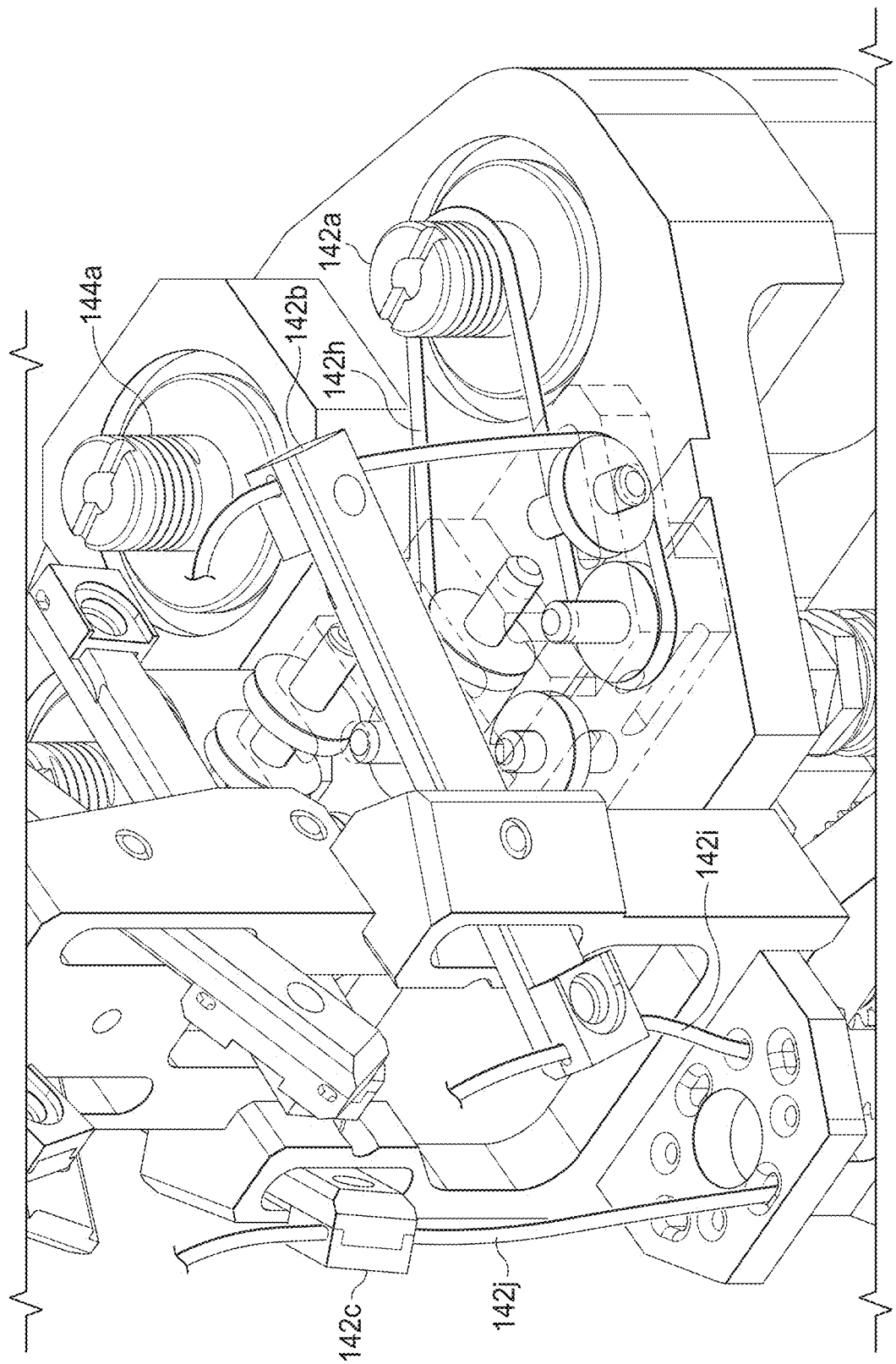
Figure 5C:
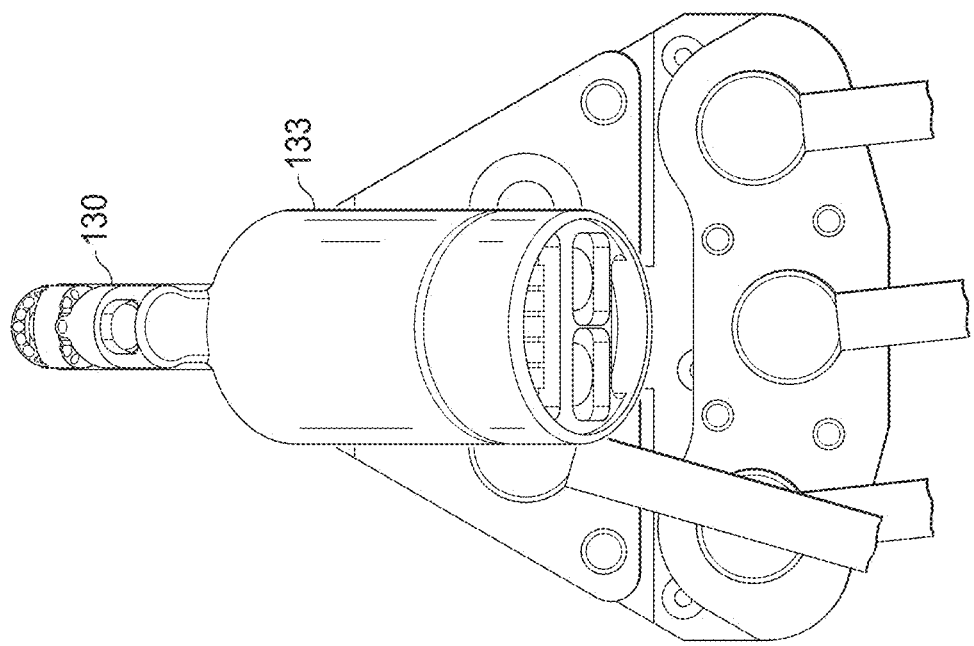
FIG. 5C is an illustration of an example embodiment of certain elements of the surgical arm illustrating a position of the surgical arm when the rotary driving assembly is in a first or starting position.
Figure 5B:
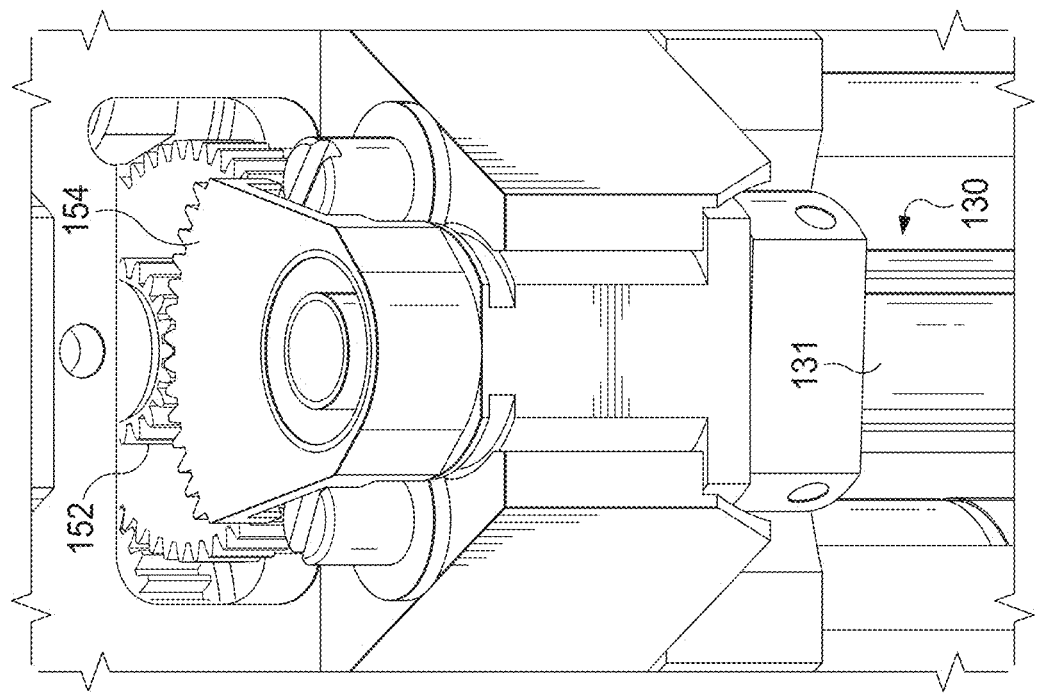
FIG. 5B is another perspective view of an example embodiment of certain elements of the rotary driving assembly in a first or starting position.
Figure 5E:
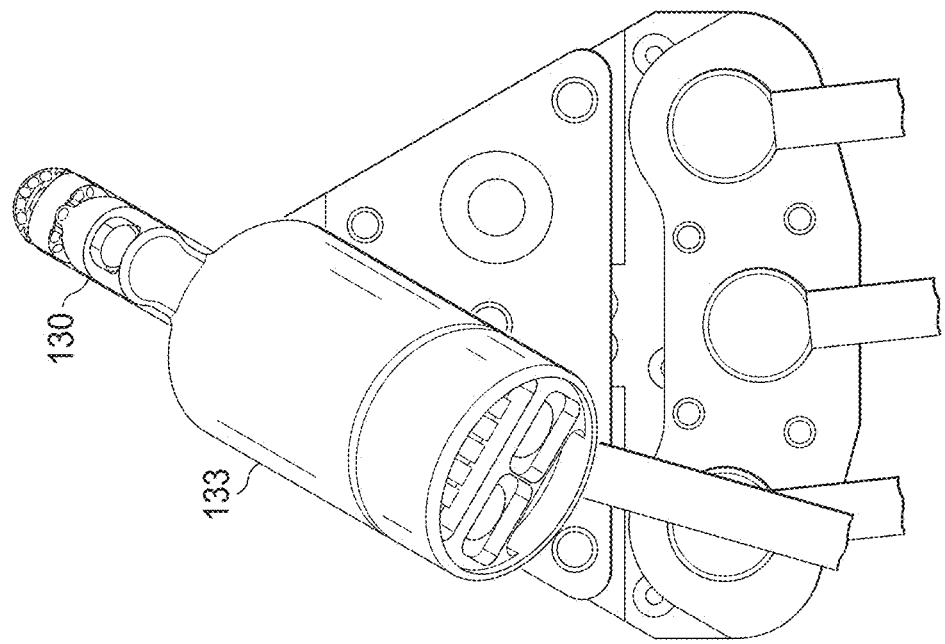
FIG. 5E is an illustration of an example embodiment of certain elements of the surgical arm illustrating a position of the surgical arm when the rotary driving assembly is in a rotated position.
Figure 5D:
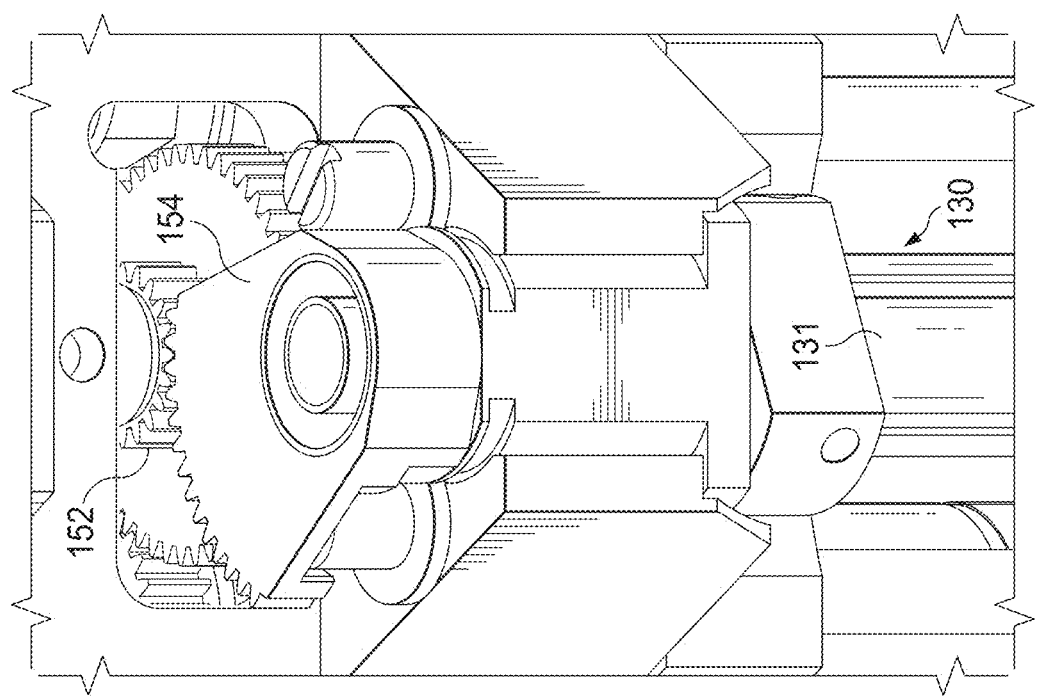
FIG. 5D is another perspective view of an example embodiment of certain elements of the rotary driving assembly in a rotated position.

As illustrated in at least FIGS. 3A-F, the distal-most end of the proximal end of the first joint assembly 135 and the proximal-most end of the distal end of the first joint assembly 135 may include one or more sloped sidewalls, or the like, on one or both sides of the joint of the first joint assembly 135 so as to limit the second segment 132 to pivotally move relative to the first segment 131 up to an angle θ1 (as illustrated in at least FIG. 3C). In example embodiments, angle θ1 may be between about 20-80 degrees, or preferably between about 30-60 degrees. Alternatively, the joint of the first joint assembly 135 may be extended or protrude outwardly from the proximal and distal ends of the first joint assembly 135 in such a way as to limit the second segment 132 to pivotally move relative to the first segment 131 up to the angle θ1. Other configurations and/or elements of the first joint assembly 135 for limiting the pivotal movement of the second segment 132 relative to the first segment 131 are also contemplated without departing from the teachings of the present disclosure.

(v) Second Joint Assembly (e.g., Second Joint Assembly 136).

In an example embodiment, the surgical arm 130 may include a second joint assembly 136. The second joint assembly 136 may be configurable to pivotally couple a distal end of the second segment 132 to a proximal end of the end effector joint assembly 137. For example, the second joint assembly 136 may include a proximal end securable or secured to a distal end of the second segment 132. The second joint assembly 136 may also include a distal end securable or secured to a proximal end of the end effector joint assembly 137. The second joint assembly 136 may also include a joint securing the proximal end and distal end of the second joint assembly 136. In some example embodiments, the joint of the second joint assembly 136 may include an elongated portion, such as a pin or rod, forming an axis that is substantially perpendicular to axis X2 irrespective of the position of the proximal end of the end effector joint assembly 137 relative to the second segment 132.

The second joint assembly 136 may also include a plurality of channels, holes, or the like. For example, the second joint assembly 136 may include one or more main channels (not shown) on each of the proximal end and distal end of the second joint assembly 136. The proximal end of the second joint assembly 136 may include a plurality of channels (or a single channel or opening), and such channels may be positioned in such a way as to positionally correspond to one or more of the channels 132a, 132b, 132c (if provided), 132a', 132b', and 132c' (if provided) of the second segment 132. The distal end of the second joint assembly 136 may include a plurality of channels (or a single channel or opening), and such channels may be positioned in such a way as to positionally correspond to one or more of the channel of the proximal end of the second joint assembly 136 when the proximal end and distal end of the second joint assembly 136 are aligned (e.g., aligned in a straight line or having their center axis lined in a straight line). Furthermore, the channel(s) of the distal end of the second joint assembly 136 may be positioned in such a way as to positionally correspond to one or more of the channel of the end effector joint assembly 137 (as described below and in the present disclosure). FIG. 9 illustrates an example embodiment of a proximal or distal end of the second joint assembly 136 having a plurality of channels for use in housing, guiding, directing, etc. one or more cables (e.g., second joint driving cables 144i or 144j, end effector joint driving cables 146i or 146j, etc., as will be further described in the present disclosure).

In an example embodiment, a cross-section of a portion of the proximal and distal ends of the second joint assembly 136 may be formed in a substantially circular shape. Put differently, the proximal and distal ends of the second joint assembly 136 may be substantially cylindrical in shape. However, it is to be understood that the cross-section of the proximal and distal ends of the second joint assembly 136 may be formed in one or more other shapes and forms without departing from the teachings of the present disclosure. For proximal and distal ends of the second joint assembly 136 having a substantially circular cross-section, a diameter of the proximal and distal ends of the second joint assembly 136 may be between about 5 to 8 mm. Furthermore, each main channel of the second joint assembly 136 may have a diameter of between about 0.5 to 1.2 mm. Furthermore, one or more of the other channels of the second joint assembly 136 may have a diameter of between about 0.5 to 1.2 mm. In an example embodiment, the second joint assembly 136 may have a length between about 3 to 10 mm when the proximal and distal ends of the second joint assembly 136 are aligned in a straight line. The second joint assembly 136 may be formed using one or more of a plurality of materials and compositions, such as surgical-grade metals, high-strength aluminum alloys, stainless steel (such as 304/304 L, 316/316 L, and 420), pure titanium, titanium alloys (such as Ti6Al4V, NiTi), and cobalt-chromium alloys. It is to be understood in the present disclosure that other materials may also be used without departing from the teachings of the present disclosure.

As illustrated in at least FIGS. 3A-F, the distal-most end of the proximal end of the second joint assembly 136 and the proximal-most end of the distal end of the second joint assembly 136 may include one or more sloped sidewalls, or the like, on one or both sides of the joint of the second joint assembly 136 so as to limit the end effector joint assembly 137 to pivotally move relative to the second segment 132 up to an angle $\theta2$ (as illustrated in at least FIG. 3C). In example embodiments, angle $\theta2$ may be between about 20 to 80 degrees, or preferably between about 30 to 60 degrees. Alternatively, the joint of the second joint assembly 136 may be extended or protrude outwardly from the proximal and distal ends of the second joint assembly 136 in such a way as to limit the end effector joint assembly 137 to pivotally move relative to the second segment 132 up to the angle $\theta2$. Other configurations and/or elements of the second joint assembly 136 for limiting the pivotal movement of the end effector joint assembly 137 relative to the second segment 132 are also contemplated without departing from the teachings of the present disclosure.

(v) End Effector Joint Assembly (e.g., End Effector Joint Assembly 137).

In an example embodiment, the surgical arm 130 may include an end effector joint assembly 137. The end effector joint assembly 137 may be configurable to pivotally couple a distal end of the second joint assembly 136 to a proximal end of the end effector assembly 133. For example, the end effector joint assembly 137 may include a proximal end securable or secured to a distal end of the second joint assembly 136. The end effector joint assembly 137 may also include a distal end securable or secured to a proximal end of the end effector assembly 133. The end effector joint assembly 137 may also include a joint securing the proximal end and distal end of the end effector joint assembly 137. In some example embodiments, the joint of the end effector joint assembly 137 may include an elongated portion, such as a pin or rod, forming an axis that is substantially perpendicular to axis X3 irrespective of the position of the proximal end of the end effector assembly 133 relative to the distal end of the second joint assembly 136.

The end effector joint assembly 137 may also include one or more channels, holes, or the like. For example, the end effector joint assembly 137 may include one or more main channels (not shown) on each of the proximal end and distal end of the end effector joint assembly 137. The proximal end of the end effector joint assembly 137 may include one or more channels, and such channels may be positioned in such a way as to positionally correspond to one or more of the channel of the distal end of the second joint assembly 136. The distal end of the end effector joint assembly 137 may include one or more channels, and such channels may be positioned in such a way as to positionally correspond to one or more of the channel of the end effector assembly 133 when the proximal end and distal end of the end effector joint assembly 137 are aligned (e.g., aligned in a straight line or having their center axis lined in a straight line). FIG. 9 illustrates an example embodiment of a proximal or distal end of the end effector joint assembly 137 having a plurality of channels for use in housing, guiding, directing, etc. one or more cables (e.g., end effector joint driving cables 146i or 146j, etc., as will be further described in the present disclosure).

In an example embodiment, a cross-section of a portion of the proximal and distal ends of the end effector joint assembly 137 may be formed in a substantially circular shape. Put differently, the proximal and distal ends of the end effector joint assembly 137 may be substantially cylindrical in shape. However, it is to be understood that the cross-section of the proximal and distal ends of the end effector joint assembly 137 may be formed in one or more other shapes and forms without departing from the teachings of the present disclosure. For proximal and distal ends of the end effector joint assembly 137 having a substantially circular cross-section, a diameter of the proximal and distal ends of the end effector joint assembly 137 may be between about 5 to 8 mm. Furthermore, each main channel of the end effector joint assembly 137 may have a diameter of between about 2 to 4 mm. Furthermore, one or more of the other channels of the end effector joint assembly 137 may have a diameter of between about 0.5 to 1.2 mm. In an example embodiment, the end effector joint assembly 137 may have a length between about 4 to 10 mm when the proximal and distal ends of the end effector joint assembly 137 are aligned in a straight line. The end effector joint assembly 137 may be formed using one or more of a plurality of materials and compositions, such as surgical-grade metals, high-strength aluminum alloys, stainless steel (such as 304/304 L, 316/316 L, and 420), pure titanium, titanium alloys (such as Ti6Al4V, NiTi), and cobalt-chromium alloys. It is to be understood in the present disclosure that other materials may also be used without departing from the teachings of the present disclosure.

As illustrated in at least FIGS. 3A-F, the distal-most end of the proximal end of the end effector joint assembly 137 and the proximal-most end of the distal end of the end effector joint assembly 137 may include one or more sloped sidewalls, or the like, on one or both sides of the joint of the end effector joint assembly 137 so as to limit the end effector assembly 133 to pivotally move relative to the second joint assembly 136 up to an angle $\theta3$ (as illustrated in at least FIG.

3B). In example embodiments, angle θ3 may be between about 20 to 80 degrees, or preferably between about 30 to 60 degrees. Alternatively, the joint of the end effector joint assembly 137 may be extended or protrude outwardly from the proximal and distal ends of the end effector joint assembly 137 in such a way as to limit the end effector assembly 133 to pivotally move relative to the second joint assembly 136 up to the angle θ3. Other configurations and/or elements of the end effector joint assembly 137 for limiting the pivotal movement of the end effector assembly 133 relative to the second joint assembly 136 are also contemplated without departing from the teachings of the present disclosure.

Joint Driving Assembly (e.g., Joint Driving Assembly 140).

As illustrated in at least FIGS. 4A-G and FIGS. 10A-B, an example embodiment of the surgical system 100 or 200 may include a joint driving assembly 140. The joint driving assembly 140 may include one or more mechanisms, devices, or the like, configurable to drive (e.g., cause a movement of, maintain a position of, restrict a movement of, counter a movement of, etc.) an element of the surgical arm 130, and may include driving of the element relative to another element of the surgical arm 130. For example, the joint driving assembly 140 may include a plurality of subassemblies, such as a first joint driving subassembly 142, second joint driving subassembly 144, and/or end effector joint driving subassembly 146. Other driving subassemblies for driving a joint assembly of the surgical arm 130 are also contemplated without departing from the teachings of the present disclosure.

As will be further described below and in the present disclosure, the first joint driving subassembly 142 may include a first joint driving subsystem 142a, first joint driving motor 142a', first joint driving cables 142i and 142j, and/or first joint control cable 142h. The second joint driving subassembly 144 may include a second joint driving subsystem 144a, second joint driving motor 144a', second joint driving cables 144i and 144j, and/or second joint control cable 144h. The end effector joint driving subassembly 146 may include an end effector joint driving subsystem 146a, end effector joint driving motor 146a', end effector joint driving cables 146i and 146j, and/or end effector joint control cable 146h. The joint driving assembly 140 may also include any one or more configurations or combinations of gears and/or gear assemblies, including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure. Although the figures illustrate the joint driving assembly 140 having three subassemblies 142, 144, and 146, it is to be understood in the present disclosure that the joint driving assembly 140 may have other quantities and/or configurations of subassemblies without departing from the teachings of the present disclosure.

These and other elements and example embodiments of the joint drive assembly 140 will now be further described with reference to the accompanying figures.

(i) First Joint Driving Subassembly (e.g., First Joint Driving Subassembly 142).

In an example embodiment, the joint drive assembly 140 may include a first joint driving subassembly 142. The first joint driving subassembly 142 may be configurable or configured to drive (e.g., cause a movement of, maintain a position of, restrict a movement of, counter a movement of, etc.) the first joint assembly 135. The first joint driving subassembly 142 may be configurable or configured to drive (e.g., cause a movement of, maintain a position of, restrict a movement of, counter a movement of, etc.) the proximal end of the second segment 132 to pivotally move or rotate around the first joint assembly 135 and/or relative to the distal end of the first segment 131. Such pivotal movement or rotating may be around or performed relative to the joint of the first joint assembly 135 securing the proximal end and distal end of the first joint assembly 135.

The first joint driving subassembly 142 may include a first joint driving subsystem 142a, first joint driving motor 142a', first joint driving cables 142i and 142j, and/or first joint control cable 142h. The first joint driving subassembly 142 may also include one or more levers, spools (or pulleys), or the like, for use in guiding or directing one or more cables of the first joint driving subassembly 142, such as a first pair of levers 142b and 142c and/or first pair of spool sets 142d/142f and 142e/142g.

In an example embodiment, the first joint driving cable 142i may be any cable, plurality of separate cables, or plurality of cables combined or configured as a unitary cable (e.g., plurality of twisted or intertwined cables). The first joint driving cable 142i may be provided, directed, guided, or run through one or more of the channels of the first segment 131, such as channel 131a, 131b, or 131c (as illustrated in at least FIG. 3F). In example embodiments, the first joint driving cable 142i may also be provided, directed, guided, or run through one or more of the channels of the proximal end and distal end of the first joint assembly 135, such as those aligned to, matching, and/or positioned so as to correspond to the positions of the channels 131a, 131b, or 131c of the first segment 131. In example embodiments, the first joint driving cable 142i may also be provided, directed, guided, or run through one or more of the channels of the second segment 132, such as channels 132a, 132b, and/or 132c, and/or at least one of the channels of the proximal end of the second joint assembly 136, such as those aligned to, matching, and/or positioned so as to correspond to the positions of the channels 132a, 132b, or 132c of the second segment 132. A proximal end of the first joint driving cable 142i may be connected to, attached to, guided or directed by, or terminated at an end of a first lever 142b of the first pair of levers 142b and 142c, and an end of the first joint control cable 142h may be connected to, attached to, guided or directed by, or terminated at another end of the first lever 142c. A distal end of the first joint driving cable 142i may be connected to, attached to, guided or directed by, or terminated to a first termination point for securing an end of one or more of the first joint driving cable 142i housed in the channels 131a, 131b, or 131c of the first segment 131. The first termination point may be positioned at a distal end of the first joint assembly 135 in such a way that, when the first joint driving subsystem 142a applies an increased tensile force or pull to the first joint driving cable 142i (in the direction that is secured to the first termination point) (which may also include a reduced tensile force or pull to the first joint driving cable 142j in the direction that is secured to a second termination point, as described in the present disclosure), the second segment 132 pivotally moves or rotates in a first direction, wherein the first termination point positioned at the distal end of the first joint assembly 135 faces the first direction. The first termination point may also be positioned within or on a portion of the second segment 132 in such a way that, when the first joint driving subsystem 142a applies an increased tensile force or pull to the first joint driving cable 142*i* (in the direction that is secured to the first termination point) (which may also include a reduced tensile force or pull to the first joint driving cable 142*j* in the direction that is secured to the second termination point, as described in the present disclosure), the second segment 132 pivotally moves or rotates in the first direction, wherein the first termination point positioned within or on the second segment 132 faces the first direction. The first termination point may also be positioned at a proximal end of the second joint assembly 136 in such a way that, when the first joint driving subsystem 142*a* applies an increased tensile force or pull to the first joint driving cable 142*i* (in the direction that is secured to the first termination point) (which may also include a reduced tensile force or pull to the first joint driving cable 142*j* in the direction that is secured to the second termination point, as described in the present disclosure), the second segment 132 pivotally moves or rotates in the first direction, wherein the first termination point positioned at the proximal end of the second joint assembly 136 faces the first direction.

In an example embodiment, the first joint driving cable 142*j* may be any cable, plurality of separate cables, or plurality of cables combined or configured as a unitary cable (e.g., plurality of twisted or intertwined cables). The first joint driving cable 142*j* may be provided, directed, guided, or run through at least one of the channels of the first segment opposite to the channel in which the first joint driving cable 142*i* is provided, directed, guided, or run, such as channels 131*a*', 131*b*', and 131*c*' that are opposite to channels 131*a*, 131*b*, and 131*c* (as illustrated in at least FIG. 3F). In example embodiments, the first joint driving cable 142*j* may also be provided, directed, guided, or run through one or more of the channels of the proximal end and distal end of the first joint assembly 135, which are aligned to, matching, and/or positioned so as to correspond to the positions of the channels 131*a*', 131*b*', and 131*c*' of the first segment 131. In example embodiments, the first joint driving cable 142*j* may also be provided, directed, guided, or run through one or more of the channels of the second segment 132, such as channels 132*a*, 132*b*, and/or 132*c*, and/or channels of the proximal end of the second joint assembly 136, which are aligned to, matching, and/or positioned so as to correspond to the positions of the channels 131*a*', 131*b*', and 131*c*' of the second segment 132. A proximal end of the first joint driving cable 142*j* may be connected to, attached to, guided or directed by, or terminated at an end of a second lever 142*c* of the first pair of levers 142*b* and 142*c*, and another end of the first joint control cable 142*h* may be connected to, attached to, guided or directed by, or terminated at another end of the second lever 142*c*. A distal end of the first joint driving cable 142*j* may be connected, attached, guided or directed by, or terminated to a second termination point for securing an end of one or more of the first joint driving cable 142*j* housed in the channels 131*a*', 131*b*', and 131*c*' of the first segment 131. The second termination point may be positioned at a distal end of the first joint assembly 135 in such a way that, when the first joint driving subsystem 142*a* applies an increased tensile force or pull to the first joint driving cable 142*j* (in the direction that is secured to the second termination point) (which may also include a reduced tensile force or pull to the first joint driving cable 142*i* in the direction that is secured to the first termination point, as described in the present disclosure), the second segment 132 pivotally moves or rotates in a second direction, wherein the second termination point positioned at the distal end of the first joint assembly 135 faces the second direction. The second termination point may also be positioned within or on a portion of the second segment 132 in such a way that, when the first joint driving subsystem 142*a* applies an increased tensile force or pull to the first joint driving cable 142*j* (in the direction that is secured to the second termination point) (which may also include a reduced tensile force or pull to the first joint driving cable 142*i* in the direction that is secured to the first termination point, as described in the present disclosure), the second segment 132 pivotally moves or rotates in the second direction, wherein the second termination point positioned within or on the second segment 132 faces the second direction. The second termination point may also be positioned at a proximal end of the second joint assembly 136 in such a way that, when the first joint driving subsystem 142*a* applies an increased tensile force or pull to the first joint driving cable 142*j* (in the direction that is secured to the second termination point) (which may also include a reduced tensile force or pull to the first joint driving cable 142*i* in the direction that is secured to the first termination point, as described in the present disclosure), the second segment 132 pivotally moves or rotates in the second direction, wherein the second termination point positioned at the proximal end of the second joint assembly 136 faces the second direction.

In operation, a first joint driving motor 142*a*' may be configurable to receive commands, such as from a controller, surgeon, etc. to drive the first joint driving subsystem 142*a*. For example, when it is desired to command the second segment 132 to pivotally move or rotate in the first direction (as described above and in the present disclosure), the first joint driving motor 142*a*' may be configurable to receive commands to drive the first joint driving subsystem 142*a* so as to apply, via first joint control cable 142*h* (e.g., also via the first lever 142*b*), the increased tensile force or pull to the first joint driving cable 142*i* (in the direction that is secured to the first termination point). One or more spools, cable guides, or the like may be provided so as to guide or run the first joint control cable 142*h* from the first joint driving subsystem 142*a* towards the first lever 142*b*, such as spools 142*d* and/or 142*f*. As another example, when it is desired to command the second segment 132 to pivotally move or rotate in the second direction (as described above and in the present disclosure), the first joint driving motor 142*a*' may be configurable to receive commands to drive the first joint driving subsystem 142*a* so as to apply, via first joint control cable 142*h* (e.g., also via the second lever 142*c*), the increased tensile force or pull to the first joint driving cable 142*j* (in the direction that is secured to the second termination point). One or more spools, cable guides, or the like may be provided so as to guide or run the first joint control cable 142*h* from the first joint driving subsystem 142*a* towards the second lever 142*c*, such as spools 142*e* and 142*g*.

The first joint driving cables 142*i* and/or 142*j* may be configured to have a tensile strength and/or withstand a tensile force of at least 200 N. The first joint driving cables 142*i* and/or 142*j* may have a diameter of between about 400 to 700 μm. The first joint driving cables 142*i* and/or 142*j* may be formed using one or more of a plurality of materials and compositions, such as surgical-grade metals, high-strength aluminum alloys, stainless steel (such as 304/304 L, 316/316 L, and 420), pure titanium, titanium alloys (such as Ti6Al4V, NiTi), and cobalt-chromium alloys. It is to be understood that other strengths, dimensions, and/or materials may also be used without departing from the teachings of the present disclosure.

(ii) Second Joint Driving Subassembly (e.g., Second Joint Driving Subassembly 144).

In an example embodiment, the joint drive assembly 140 may include a second joint driving subassembly 144. The second joint driving subassembly 144 may be configurable or configured to drive (e.g., cause a movement of, maintain a position of, restrict a movement of, counter a movement of, etc.) the second joint assembly 136. The second joint driving subassembly 144 may be configurable or configured to drive (e.g., cause a movement of, maintain a position of, restrict a movement of, counter a movement of, etc.) the proximal end of the end effector joint assembly 137 to pivotally move or rotate around the second joint assembly 136 and/or relative to the distal end of the second segment 132. Such pivotal movement or rotating may be around or performed relative to the joint of the second joint assembly 136 securing the proximal end and distal end of the second joint assembly 136.

The second joint driving subassembly 144 may include a second joint driving subsystem 144a, second joint driving motor 144a', second joint driving cables 144i and 144j, and/or second joint control cable 144h. The second joint driving subassembly 144 may also include one or more levers, spools (or pulleys), or the like, for use in guiding or directing one or more cables of the second joint driving subassembly 144, such as a second pair of levers 144b and 144c and/or second pair of spool sets 144d/144f and 144e/144g.

In an example embodiment, the second joint driving cable 144i may be any cable, plurality of separate cables, or plurality of cables combined or configured as a unitary cable (e.g., plurality of twisted or intertwined cables). The second joint driving cable 144i may be provided, directed, guided, or run through one or more of the channels of the first segment 131, such as channel 131a, 131b, or 131c (as illustrated in at least FIG. 3F). In example embodiments, the second joint driving cable 144i may also be provided, directed, guided, or run through one or more of the channels of the proximal end and distal end of the first joint assembly 135, such as those aligned to, matching, and/or positioned so as to correspond to the positions of the channels 131a, 131b, or 131c of the first segment 131. In example embodiments, the second joint driving cable 144i may also be provided, directed, guided, or run through one or more of the channels of the second segment 132, such as channels 132a, 132b, and/or 132c, and/or at least one of the channels of the proximal end of the second joint assembly 136, such as those aligned to, matching, and/or positioned so as to correspond to the positions of the channels 132a, 132b, or 132c of the second segment 132. In example embodiments, the second joint driving cable 144i may also be provided, directed, guided, or run through one or more of the channels of the proximal end and distal end of the second joint assembly 136, such as those aligned to, matching, and/or positioned so as to correspond to the positions of the channels 132a, 132b, and/or 132c, and/or at least one of the channels of the proximal end of the end effector joint assembly 137, such as those aligned to, matching, and/or positioned so as to correspond to the positions of the channels of the distal end of the second joint assembly 136. A proximal end of the second joint driving cable 144i may be connected to, attached to, guided or directed by, or terminated at an end of a first lever 144b of the second pair of levers 144b and 144c, and an end of the second joint control cable 144h may be connected to, attached to, guided or directed by, or terminated at another end of the first lever 144c. A distal end of the second joint driving cable 144i may be connected to, attached to, guided or directed by, or terminated to a first termination point for securing an end of one or more of the second joint driving cable 144i housed in the channels 131a, 131b, or 131c (and channels 132a, 132b, or 132c). The first termination point may be positioned at a distal end of the second joint assembly 136 in such a way that, when the second joint driving subsystem 144a applies an increased tensile force or pull to the second joint driving cable 144i (in the direction that is secured to the first termination point) (which may also include a reduced tensile force or pull to the second joint driving cable 144j in the direction that is secured to a second termination point, as described in the present disclosure), the end effector joint assembly 137 pivotally moves or rotates in a third direction, wherein the first termination point positioned at the distal end of the second joint assembly 136 faces the third direction. The first termination point may also be positioned within or on a portion of the end effector joint assembly 137 (or third joint assembly 138, if provided) in such a way that, when the second joint driving subsystem 144a applies an increased tensile force or pull to the second joint driving cable 144i (in the direction that is secured to the first termination point) (which may also include a reduced tensile force or pull to the second joint driving cable 144j in the direction that is secured to the second termination point, as described in the present disclosure), the end effector joint assembly 137 pivotally moves or rotates in a third direction, wherein the first termination point positioned within or on the end effector joint assembly 137 faces the third direction.

In an example embodiment, the second joint driving cable 144j may be any cable, plurality of separate cables, or plurality of cables combined or configured as a unitary cable (e.g., plurality of twisted or intertwined cables). The second joint driving cable 144j may be provided, directed, guided, or run through at least one of the channels of the first segment opposite to the channel in which the second joint driving cable 144i is provided, directed, guided, or run, such as channels 131a', 131b', and 131c' that are opposite to channels 131a, 131b, and 131c (as illustrated in at least FIG. 3F). In example embodiments, the second joint driving cable 144j may also be provided, directed, guided, or run through one or more of the channels of the proximal end and distal end of the first joint assembly 135, which are aligned to, matching, and/or positioned so as to correspond to the positions of the channels 131a', 131b', and 131c' of the first segment 131. In example embodiments, the second joint driving cable 144j may also be provided, directed, guided, or run through one or more of the channels of the second segment 132, such as channels 132a, 132b, and/or 132c, and/or channels of the proximal end of the second joint assembly 136, which are aligned to, matching, and/or positioned so as to correspond to the positions of the channels 131a', 131b', and 131c' of the second segment 132. In example embodiments, the second joint driving cable 144j may also be provided, directed, guided, or run through one or more of the channels of the proximal end and distal end of the second joint assembly 136, such as those aligned to, matching, and/or positioned so as to correspond to the positions of the channels 132a, 132b, and/or 132c, and/or at least one of the channels of the proximal end of the end effector joint assembly 137, such as those aligned to, matching, and/or positioned so as to correspond to the positions of the channels of the distal end of the second joint assembly 136. A proximal end of the second joint driving cable 144j may be connected to, attached to, guided or directed by, or terminated at an end of a second lever 144c of the second pair of levers 144b and 144c, and another end of the second joint control cable 144*h* may be connected to, attached to, guided or directed by, or terminated at another end of the second lever 144*c*. A distal end of the second joint driving cable 144*j* may be connected, attached, guided or directed by, or terminated to a second termination point for securing an end of one or more of the second joint driving cable 144*j* housed in the channels 131*a'*, 131*b'*, and 131*c'* of the first segment 131. The second termination point may be positioned at a distal end of the second joint assembly 136 in such a way that, when the second joint driving subsystem 144*a* applies an increased tensile force or pull to the second joint driving cable 144*j* (in the direction that is secured to the second termination point) (which may also include a reduced tensile force or pull to the second joint driving cable 144*i* in the direction that is secured to the first termination point, as described in the present disclosure), the end effector joint assembly 137 pivotally moves or rotates in a fourth direction, wherein the second termination point positioned at the distal end of the second joint assembly 136 faces the fourth direction. The second termination point may also be positioned within or on a portion of the end effector joint assembly 137 in such a way that, when the second joint driving subsystem 144*a* applies an increased tensile force or pull to the second joint driving cable 144*j* (in the direction that is secured to the second termination point) (which may also include a reduced tensile force or pull to the second joint driving cable 144*i* in the direction that is secured to the first termination point, as described in the present disclosure), the end effector joint assembly 137 pivotally moves or rotates in the fourth direction, wherein the second termination point positioned within or on the end effector joint assembly 137 faces the fourth direction.

In operation, a second joint driving motor 144*a'* may be configurable to receive commands, such as from a controller, surgeon, etc. to drive the second joint driving subsystem 144*a*. For example, when it is desired to command the end effector joint assembly 137 (that is, the section(s) of the surgical arm 130 distal to the distal end of the second joint assembly 136) to pivotally move or rotate in the third direction (as described above and in the present disclosure), the second joint driving motor 144*a'* may be configurable to receive commands to drive the second joint driving subsystem 144*a* so as to apply, via second joint control cable 144*h* (e.g., also via the first lever 144*b*), the increased tensile force or pull to the second joint driving cable 144*i* (in the direction that is secured to the first termination point). One or more spools, cable guides, or the like may be provided so as to guide or run the second joint control cable 144*h* from the second joint driving subsystem 144*a* towards the first lever 144*b*, such as spools 144*d* and/or 144*f*. As another example, when it is desired to command the end effector joint assembly 137 (that is, the section(s) of the surgical arm 130 distal to the distal end of the second joint assembly 136) to pivotally move or rotate in the fourth direction (as described above and in the present disclosure), the second joint driving motor 144*a'* may be configurable to receive commands to drive the second joint driving subsystem 144*a* so as to apply, via second joint control cable 144*h* (e.g., also via the second lever 144*c*), the increased tensile force or pull to the second joint driving cable 144*j* (in the direction that is secured to the second termination point). One or more spools, cable guides, or the like may be provided so as to guide or run the second joint control cable 144*h* from the second joint driving subsystem 144*a* towards the second lever 144*c*, such as spools 144*e* and 144*g*.

The second joint driving cables 144*i* and/or 144*j* may be configured to have a tensile strength and/or withstand a tensile force of at least 200 N. The second joint driving cables 144*i* and/or 144*j* may have a diameter of between about 400 to 700 μm. The second joint driving cables 144*i* and/or 144*j* may be formed using one or more of a plurality of materials and compositions, such as surgical-grade metals, high-strength aluminum alloys, stainless steel (such as 304/304 L, 316/316 L, and 420), pure titanium, titanium alloys (such as Ti6Al4V, NiTi), and cobalt-chromium alloys. It is to be understood that other strengths, dimensions, and/or materials may also be used without departing from the teachings of the present disclosure.

(iii) End Effector Joint Driving Subassembly (e.g., End Effector Joint Driving Subassembly 146).

In an example embodiment, the joint drive assembly 140 may include an end effector joint driving subassembly 146. The end effector joint driving subassembly 146 may be configurable or configured to drive (e.g., cause a movement of, maintain a position of, restrict a movement of, counter a movement of, etc.) the end effector joint assembly 137. The end effector joint driving subassembly 146 may be configurable or configured to drive (e.g., cause a movement of, maintain a position of, restrict a movement of, counter a movement of, etc.) the end effector assembly 133 to pivotally move or rotate around the end effector joint assembly 137 and/or relative to the distal end of the second joint assembly 136. Such pivotal movement or rotating may be around or performed relative to the joint of the end effector joint assembly 137 securing the proximal end and distal end of the end effector joint assembly 137.

The end effector joint driving subassembly 146 may include an end effector joint driving subsystem 146*a*, end effector joint driving motor 146*a'*, end effector joint driving cables 146*i* and 146*j*, and/or end effector joint control cable 146*h*. The end effector joint driving subassembly 146 may also include one or more levers, spools (or pulleys), or the like, for use in guiding or directing one or more cables of the end effector joint driving subassembly 146, such as a third pair of levers 146*b* and 146*c* and/or third pair of spool sets 146*d*/146*f* and 146*e*/146*g*.

In an example embodiment, the end effector joint driving cable 146*i* may be any cable, plurality of separate cables, or plurality of cables combined or configured as a unitary cable (e.g., plurality of twisted or intertwined cables). The end effector joint driving cable 146*i* may be provided, directed, guided, or run through one or more of the channels of the first segment 131, such as channel 131*a*, 131*b*, or 131*c* (as illustrated in at least FIG. 3F). In example embodiments, the end effector joint driving cable 146*i* may also be provided, directed, guided, or run through one or more of the channels of the proximal end and distal end of the first joint assembly 135, such as those aligned to, matching, and/or positioned so as to correspond to the positions of the channels 131*a*, 131*b*, or 131*c* of the first segment 131. In example embodiments, the end effector joint driving cable 146*i* may also be provided, directed, guided, or run through one or more of the channels of the second segment 132, such as channels 132*a*, 132*b*, and/or 132*c*, and/or at least one of the channels of the proximal end of the second joint assembly 136, such as those aligned to, matching, and/or positioned so as to correspond to the positions of the channels 132*a*, 132*b*, or 132*c* of the second segment 132. In example embodiments, the end effector joint driving cable 146*i* may also be provided, directed, guided, or run through one or more of the channels of the proximal end and distal end of the second joint assembly 136, such as those aligned to, matching, and/or positioned so as to correspond to the positions of the channels 132*a*, 132*b*, and/or 132*c*, and/or at least one of the channels of the proximal and/or distal ends of the end effector joint assembly 137, such as those aligned to, matching, and/or positioned so as to correspond to the positions of the channels of the distal end of the second joint assembly 136. The end effector joint driving cable 146*i* may also be provided, directed, guided, or run through one or more of the channels of the end effector assembly 133 (not shown), and such channels may be aligned to, matching, and/or positioned so as to correspond to the positions of the channels of the end effector joint assembly 137. A proximal end of the end effector joint driving cable 146*i* may be connected to, attached to, guided or directed by, or terminated at an end of a first lever 146*b* of the third pair of levers 146*b* and 146*c*, and an end of the end effector joint control cable 146*h* may be connected to, attached to, guided or directed by, or terminated at another end of the first lever 146*c*. A distal end of the end effector joint driving cable 146*i* may be connected to, attached to, guided or directed by, or terminated to a first termination point for securing an end of one or more of the end effector joint driving cable 146*i* housed in the channels 131*a*, 131*b*, or 131*c* (and channels 132*a*, 132*b*, or 132*c*). The first termination point may be positioned at a distal end of the end effector joint assembly 137 in such a way that, when the end effector joint driving subsystem 146*a* applies an increased tensile force or pull to the end effector joint driving cable 146*i* (in the direction that is secured to the first termination point) (which may also include a reduced tensile force or pull to the end effector joint driving cable 146*j* in the direction that is secured to a second termination point, as described in the present disclosure), the end effector assembly 133 pivotally moves or rotates in a fifth direction, wherein the first termination point positioned at the distal end of the end effector joint assembly 137 faces the fifth direction. The first termination point may also be positioned within or on a portion of the end effector assembly 133 in such a way that, when the end effector joint driving subsystem 146*a* applies an increased tensile force or pull to the end effector joint driving cable 146*i* (in the direction that is secured to the first termination point) (which may also include a reduced tensile force or pull to the end effector joint driving cable 146*j* in the direction that is secured to the second termination point, as described in the present disclosure), the end effector assembly 133 pivotally moves or rotates in the fifth direction, wherein the first termination point positioned within or on the end effector assembly 133 faces the fifth direction.

In an example embodiment, the end effector joint driving cable 146*j* may be any cable, plurality of separate cables, or plurality of cables combined or configured as a unitary cable (e.g., plurality of twisted or intertwined cables). The end effector joint driving cable 146*j* may be provided, directed, guided, or run through at least one of the channels of the first segment opposite to the channel in which the end effector joint driving cable 146*i* is provided, directed, guided, or run, such as channels 131*a'*, 131*b'*, and 131*c'* that are opposite to channels 131*a*, 131*b*, and 131*c* (as illustrated in at least FIG. 3F). In example embodiments, the end effector joint driving cable 146*j* may also be provided, directed, guided, or run through one or more of the channels of the proximal end and distal end of the first joint assembly 135, which are aligned to, matching, and/or positioned so as to correspond to the positions of the channels 131*a'*, 131*b'*, and 131*c'* of the first segment 131. In example embodiments, the end effector joint driving cable 146*j* may also be provided, directed, guided, or run through one or more of the channels of the second segment 132, such as channels 132*a*, 132*b*, and/or 132*c*, and/or channels of the proximal end of the second joint assembly 136, which are aligned to, matching, and/or positioned so as to correspond to the positions of the channels 131*a'*, 131*b'*, and 131*c'* of the second segment 132. In example embodiments, the end effector joint driving cable 146*j* may also be provided, directed, guided, or run through one or more of the channels of the proximal end and distal end of the second joint assembly 136, such as those aligned to, matching, and/or positioned so as to correspond to the positions of the channels 132*a*, 132*b*, and/or 132*c*, and/or at least one of the channels of the proximal end of the end effector joint assembly 137, such as those aligned to, matching, and/or positioned so as to correspond to the positions of the channels of the distal end of the second joint assembly 136. The end effector joint driving cable 146*j* may also be provided, directed, guided, or run through one or more of the channels of the end effector assembly 133 (not shown), and such channels may be aligned to, matching, and/or positioned so as to correspond to the positions of the channels of the end effector joint assembly 137. A proximal end of the end effector joint driving cable 146*j* may be connected to, attached to, guided or directed by, or terminated at an end of a second lever 146*c* of the third pair of levers 146*b* and 146*c*, and another end of the end effector joint control cable 146*h* may be connected to, attached to, guided or directed by, or terminated at another end of the second lever 146*c*. A distal end of the end effector joint driving cable 146*j* may be connected, attached, guided or directed by, or terminated to a second termination point for securing an end of one or more of the end effector joint driving cable 144*j* housed in the channels 131*a'*, 131*b'*, and 131*c'* of the first segment 131. The second termination point may be positioned at a distal end of the end effector joint assembly 137 in such a way that, when the end effector joint driving subsystem 146*a* applies an increased tensile force or pull to the end effector joint driving cable 146*j* (in the direction that is secured to the second termination point) (which may also include a reduced tensile force or pull to the end effector joint driving cable 146*i* in the direction that is secured to the first termination point, as described in the present disclosure), the end effector assembly 133 pivotally moves or rotates in a sixth direction, wherein the second termination point positioned at a distal end of the end effector joint assembly 137 faces the sixth direction. The second termination point may also be positioned within or on a portion of the end effector assembly 133 in such a way that, when the end effector joint driving subsystem 146*a* applies an increased tensile force or pull to the end effector joint driving cable 146*j* (in the direction that is secured to the second termination point) (which may also include a reduced tensile force or pull to the end effector joint driving cable 146*i* in the direction that is secured to the first termination point, as described in the present disclosure), the end effector assembly 133 pivotally moves or rotates in the sixth direction, wherein the second termination point positioned within or on the end effector assembly 133 faces the fourth direction.

It is to be understood in the present disclosure that the first direction, second direction, third direction, fourth direction, fifth direction, and/or sixth direction may or may not be the same direction and may be a movement or rotation relative to a same or different reference axis. For example, first direction, third direction, and/or fifth direction may be a movement or rotation in the same direction, and similarly, second direction, fourth direction, and/or sixth direction may be a movement or rotation in the same direction. As another example, the first direction and third direction may be a movement or rotation in the same direction, and the fifth direction may be a movement or rotation in a different direction than the first and third directions. Similarly, the second and fourth direction may be a movement or rotation in the same direction, and the sixth direction may be a movement or rotation in a different direction than the second and fourth directions. Other configurations and movements are also contemplated without departing from the teachings of the present disclosure.

In operation, an end effector joint driving motor 146a' may be configurable to receive commands, such as from a controller, surgeon, etc., to drive the end effector joint driving subsystem 146a. For example, when it is desired to command the end effector assembly 133 (that is, the section(s) of the surgical arm 130 distal to the distal end of the end effector joint assembly 137) to pivotally move or rotate in the fifth direction (as described above and in the present disclosure), the end effector joint driving motor 146a' may be configurable to receive commands to drive the end effector joint driving subsystem 146a so as to apply, via end effector joint control cable 146h (e.g., also via the first lever 146b), the increased tensile force or pull to the end effector joint driving cable 146i (in the direction that is secured to the first termination point). One or more spools, cable guides, or the like may be provided so as to guide or run the end effector joint control cable 146h from the end effector joint driving subsystem 146a towards the first lever 146b, such as spools 146d and/or 146f. As another example, when it is desired to command the end effector assembly 133 (that is, the section(s) of the surgical arm 130 distal to the distal end of the end effector joint assembly 137) to pivotally move or rotate in the sixth direction (as described above and in the present disclosure), the end effector joint driving motor 146a' may be configurable to receive commands to drive the end effector joint driving subsystem 146a so as to apply, via end effector joint control cable 146h (e.g., also via the second lever 146c), the increased tensile force or pull to the end effector joint driving cable 146j (in the direction that is secured to the second termination point). One or more spools, cable guides, or the like may be provided so as to guide or run the end effector joint control cable 146h from the end effector joint driving subsystem 146a towards the second lever 146c, such as spools 146e and 146g.

The end effector joint driving cables 146i and/or 146j may be configured to have a tensile strength and/or withstand a tensile force of at least 200 N. The end effector joint driving cables 146i and/or 146j may have a diameter of between about 400 to 700 µm. The end effector joint driving cables 146i and/or 146j may be formed using one or more of a plurality of materials and compositions, such as surgical-grade metals, high-strength aluminum alloys, stainless steel (such as 304/304 L, 316/316 L, and 420), pure titanium, titanium alloys (such as Ti6Al4V, NiTi), and cobalt-chromium alloys. It is to be understood that other strengths, dimensions, and/or materials may be used without departing from the teachings of the present disclosure.

Rotary Driving Assembly (e.g., Rotary Driving Assembly 150).

As illustrated in at least FIGS. 5A-E, an example embodiment of the surgical assembly 100 or 200 may include a rotary driving assembly 150. The rotary driving assembly 150 may include one or more mechanisms, devices, or the like, configurable to drive (e.g., cause or control a movement of, maintain or control a position of, restrict a movement of, counter a movement of, etc.) an element of the surgical assembly 100 or 200, and may include driving of an element relative to another element of the surgical assembly 100 or 200. For example, the rotary driving assembly 150 may include a plurality of subassemblies, such as a rotary driving subassembly 152, rotary driven subassembly 154, and/or rotary driving motor 156. Other driving subassemblies for driving one or more elements of the surgical system 100 or 200, including the surgical arm 130, are also contemplated without departing from the teachings of the present disclosure. For example, the rotary driving assembly 150 may include any one or more configurations or combinations of gears, gear assemblies, cables, springs, etc., including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure.

In an example embodiment, the rotary driving assembly 150 may be configurable or configured to cause a rotary movement of the surgical arm 130, such as in direction A and/or direction B (as illustrated in at least FIG. 5A). For example, the rotary driving assembly 150 may be configurable or configured to cause a rotation of the surgical arm 130 relative to an axis X1 formed by the first segment 131 (when the surgical arm is secured to the port assembly 110). As another example, the rotary driving assembly 150 may be configurable or configured to cause a rotation of the surgical arm 130 relative to an axis formed by the port assembly 110.

In operation, the rotary driving motor 156 may be configurable or configured to receive a command or control instruction from a controller and/or surgeon to drive a rotary movement of the surgical arm 130 by driving the rotary drive subassembly 152, which in turn drives the rotary driven subassembly 154. The rotary driven subassembly 154 may be configurable or configured to secure to at least a portion of the surgical arm 130, such as the first segment 131, and drive the first arm segment 131 to rotate when driven by the rotary drive subassembly 152. Other configurations and movements are also contemplated without departing from the teachings of the present disclosure.

Telescopic Driving Assembly (e.g., Telescopic Driving Assembly 160).

Figure 6A:
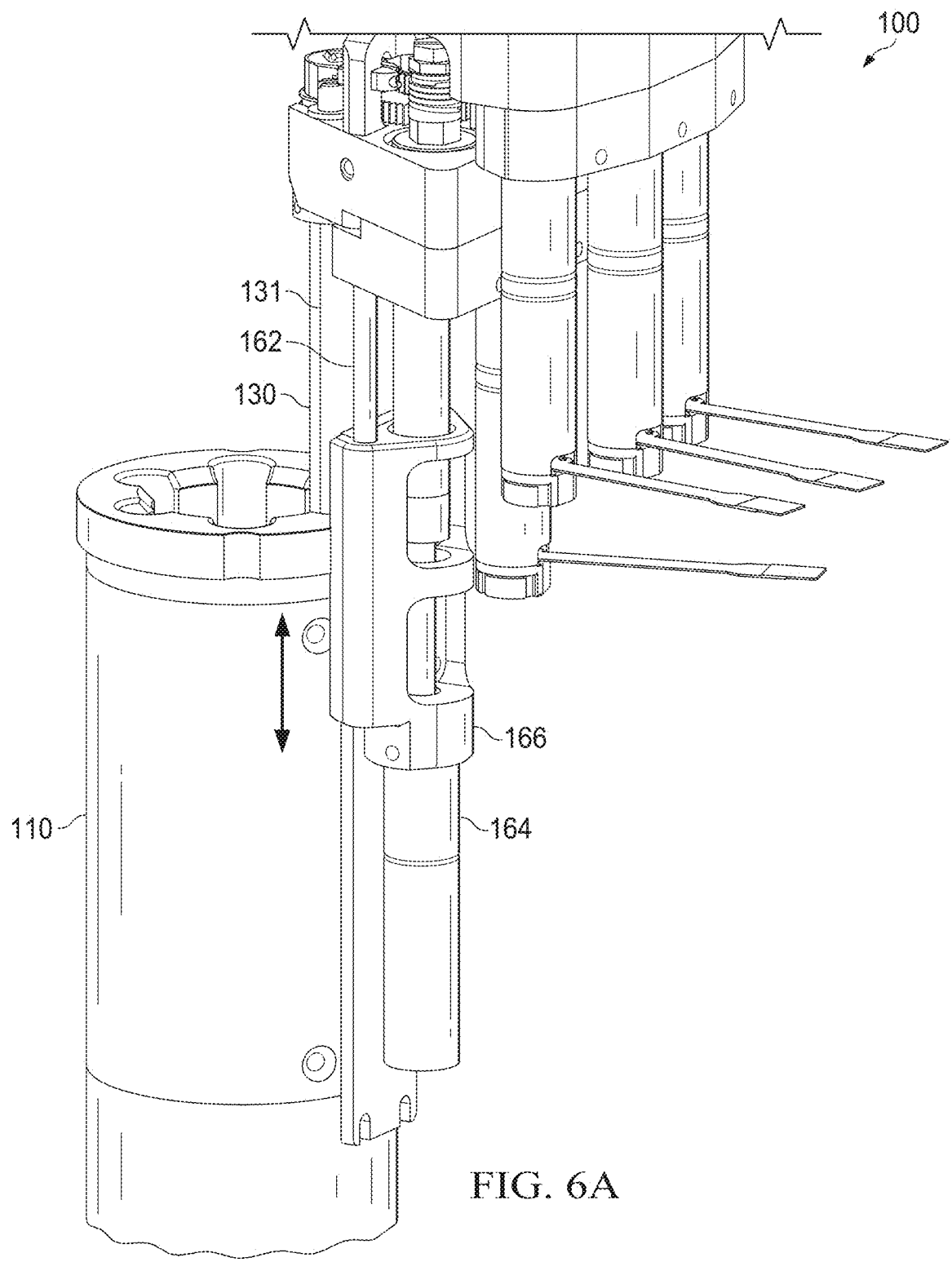
FIG. 6A is a perspective view of an example embodiment of a surgical system having a telescopic driving assembly.
Figure 6B:
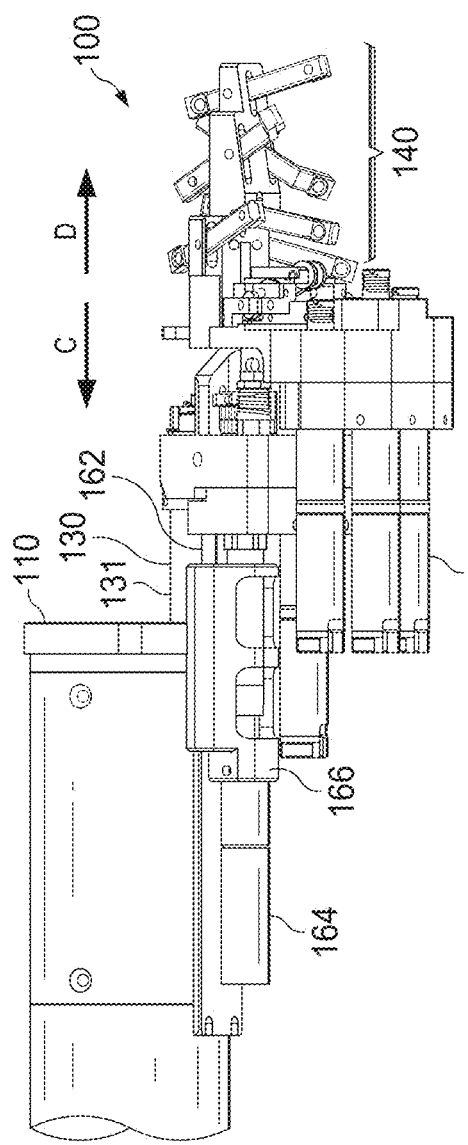
FIGS. 6B-C are side views of an example embodiment of different positions of the surgical system when the telescopic driving assembly provides for a linear displacement of the surgical arm.
Figure 6C:
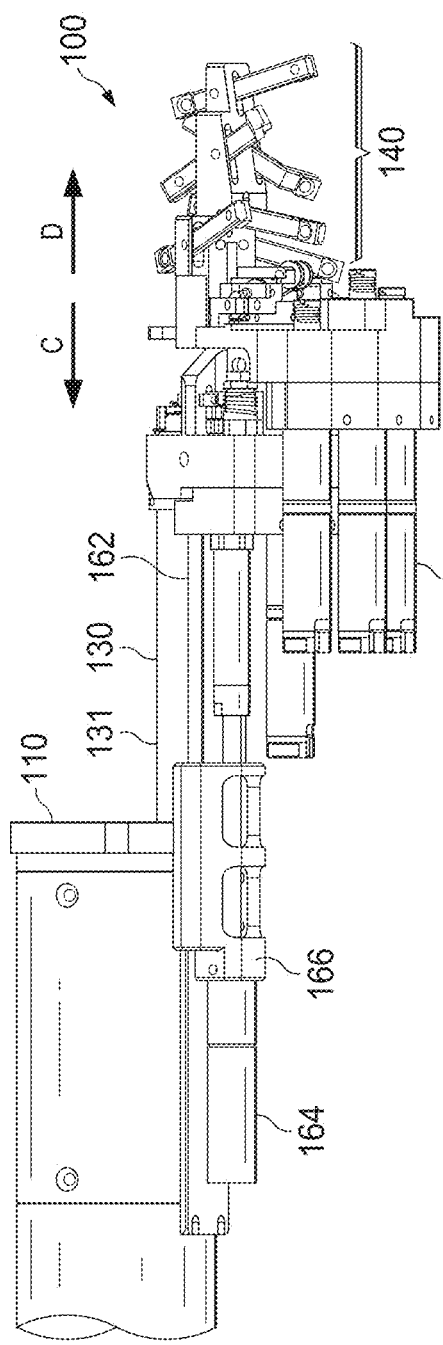
Figure 7A:
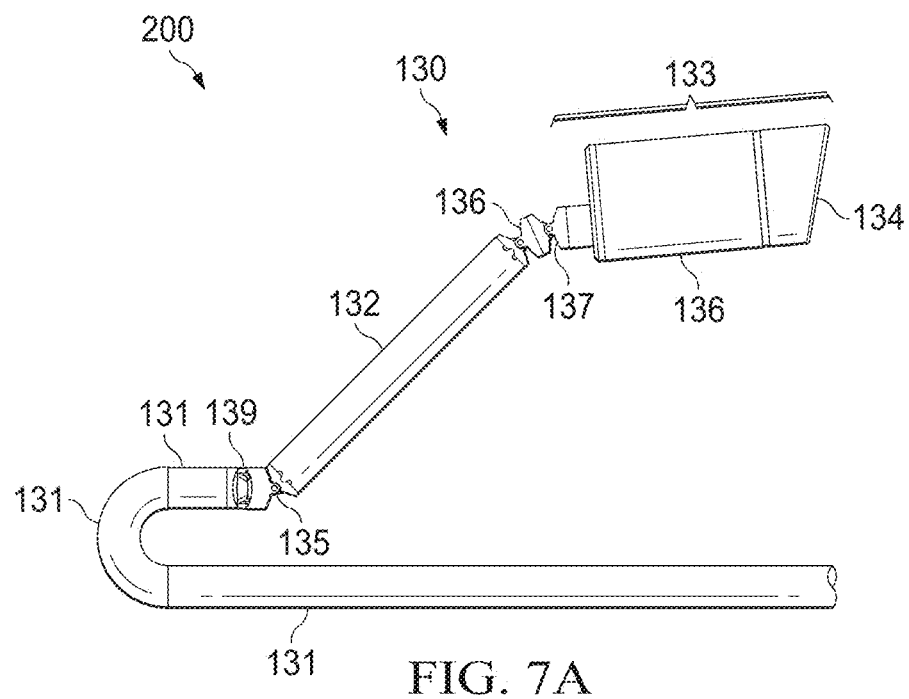
FIG. 7A is a side view of an example embodiment of a surgical arm in a reverse configuration.
Figure 7B:
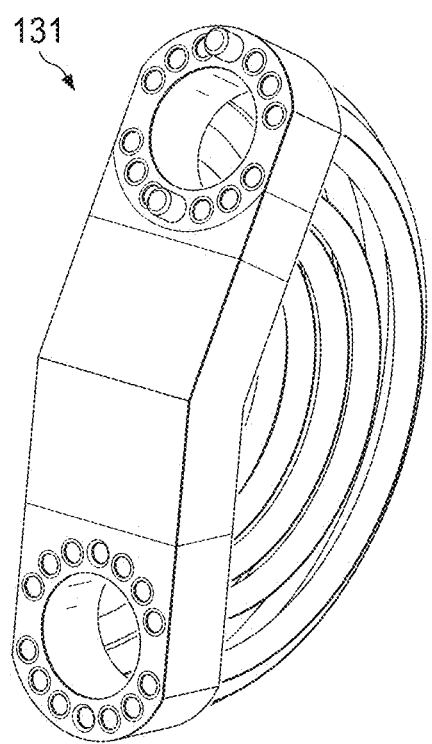
FIG. 7B is a perspective view of an example embodiment of a U-shaped portion of the first segment of the surgical arm.
Figure 8A:
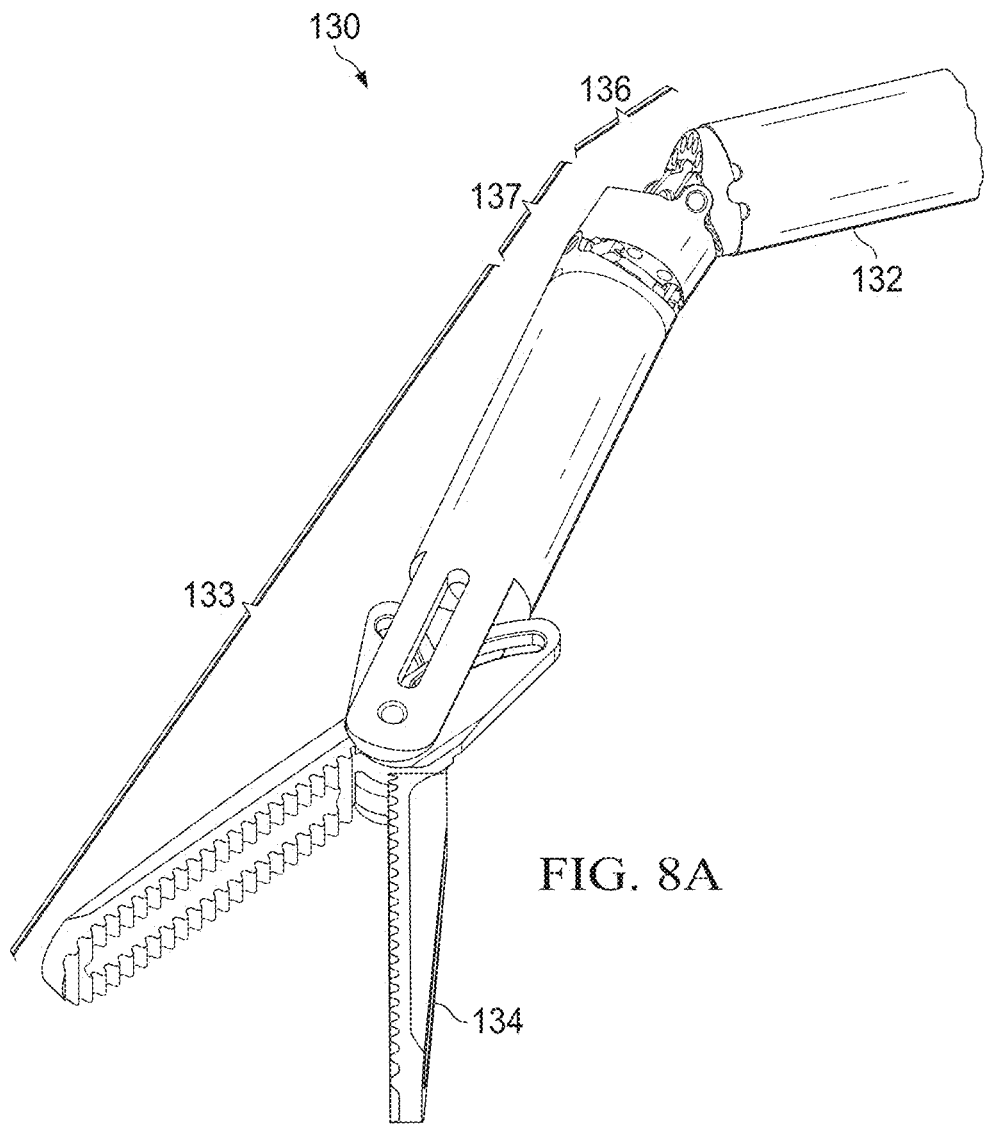
FIGS. 8A-C are perspective views of example embodiments of an end effector assembly having an instrument in the form of a retractor, image capturing device, and suction and/or irrigation device, respectively.
Figure 8B:
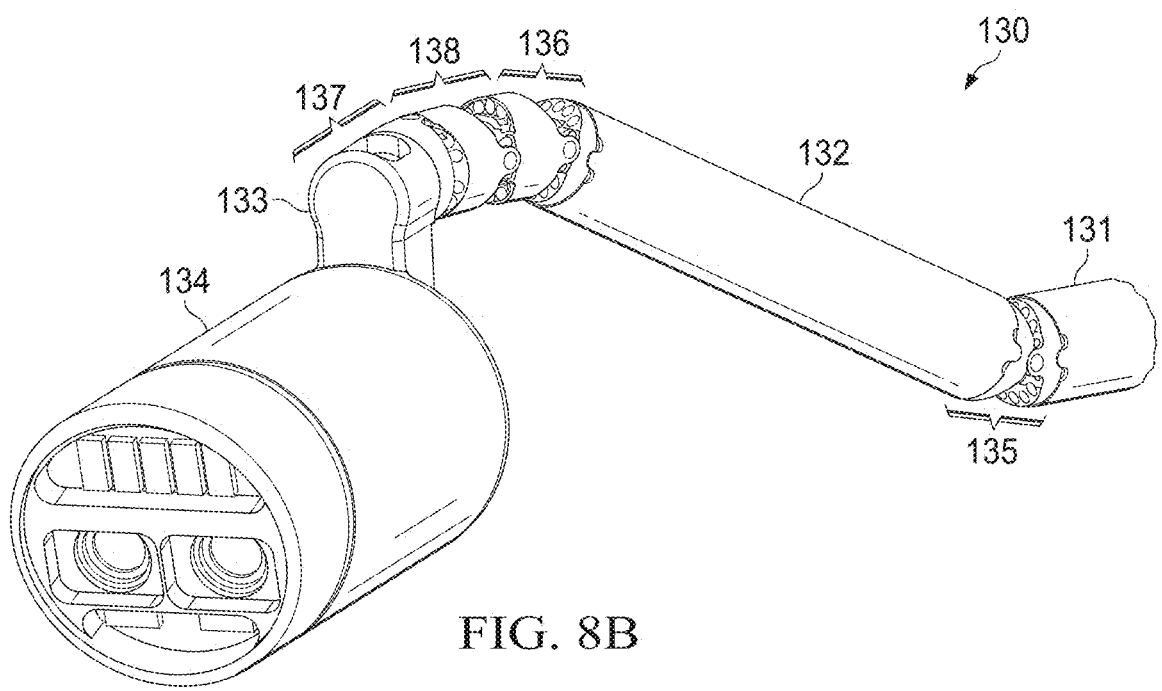
Figure 8C:
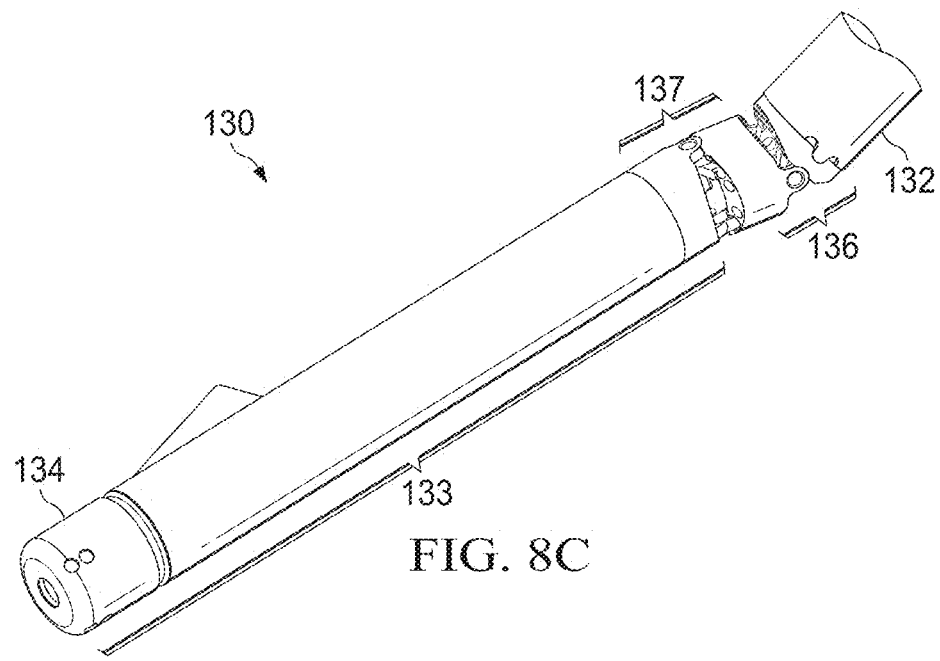

As illustrated in at least FIGS. 6A-C, an example embodiment of the surgical assembly 100 or 200 may include a telescopic driving assembly 160. The telescopic driving assembly 160 may include one or more mechanisms, devices, or the like, configurable to drive (e.g., cause or control a movement of, maintain or control a position of, restrict a movement of, counter a movement of, etc.) an element of the surgical assembly 100 or 200, and may include driving of an element relative to another element of the surgical assembly 100 or 200. For example, the telescopic driving assembly 160 may include a plurality of subassemblies, such as a guide rod subassembly 162, telescopic driving motor 164, and/or telescopic anchor 166. Other driving subassemblies for driving one or more elements of the surgical system 100 or 200, including the surgical arm 130, are also contemplated without departing from the teachings of the present disclosure. For example, the telescopic driving assembly 160 may include any one or more configurations or combinations of gears, gear assemblies, cables, springs, etc., including straight gear configurations, planetary gear configurations, beveled gear configurations, spiral beveled gear configurations, hypoid gear configurations, helical gear configurations, worm gear configurations, and/or any other gear and/or mechanical configurations (such as wire and pulley) without departing from the teachings of the present disclosure.

In an example embodiment, the telescopic driving assembly 160 may be configurable or configured to cause a linear movement of at least the surgical arm 130 relative to at least the port assembly 110, such as in direction C and/or direction D (as illustrated in at least FIGS. 6B and 6C). For example, the telescopic driving assembly 160 may be configurable or configured to cause a forward movement, backward movement, inward movement towards the patient cavity, and/or outward movement from the patient cavity of the surgical arm 130.

In operation, the telescopic driving motor 164 may be configurable or configured to receive a command or control instruction from a controller and/or surgeon to drive a linear movement of the surgical arm 130, and such linear movement may be maintained and/or controlled via the guide rod assembly 162. To enable such linear movement of the surgical arm 130 relative to the port assembly 110, the telescopic driving motor 164 may be securable or secured at one end to a portion of the port assembly 110 (e.g., via the telescopic anchor 166) and securable or secured at another end to a portion of the surgical arm 130 (e.g., first segment 131), a portion of the joint driving assembly 140, and/or a portion of the rotary driving assembly 150. Furthermore, the telescopic driving motor 164 may include a leadscrew (not shown), or the like, operable to control the linear movement of the surgical arm 130 by rotating of the leadscrew in a first direction (e.g., clockwise direction to cause a forward movement C) and a second direction (e.g., counter clockwise direction to cause a backward movement D).

In example embodiments, the telescopic driving assembly 160 may be configurable to cause a linear movement of only the surgical arm 130. In other example embodiments, the telescopic driving assembly 160 may be configurable to cause a linear movement of the surgical arm 130 and one or more of the joint driving assembly 140 and/or the rotary driving assembly 150. Other configurations and movements are also contemplated without departing from the teachings of the present disclosure.

Controller.

In example embodiments, the surgical system 100 or 200 may include a controller (or computing device, manipulator, and/or master input device). The controller may include one or more processors. The controller may be configurable to perform one or more of a plurality of actions, operations, and/or configurations, in, on, and/or to one or more elements of the surgical system 100 or 200, as described above and in the present disclosure. For example, the controller may be configurable to communicate with and/or control one or more elements of the surgical system 100 or 200, such as one or more elements of the surgical arm assembly 120, one or more elements of the surgical arm assembly 130, one or more elements of the joint driving assembly 140, one or more elements of the rotary driving assembly 150, and/or one or more elements of the telescopic driving assembly 160. The controller may be accessible and/or controllable by a surgeon or surgical team (e.g., via a user interface), and the surgeon or surgical team may be able to communicate with and/or control the configuring and/or operation of the one or more elements of the surgical system 100 or 200. For example, the controller may be configurable to control a movement and action of some or all parts of the surgical arm assembly 130, joint driving assembly 140, rotary driving assembly 150, and/or telescopic driving assembly 160. The controller may be configurable to receive, from the user interface (e.g. user interface 910), user interaction information (e.g., performed by the surgical team) representative of user interactions performed on the user interface. The controller may be further configurable to process the received user interaction information. The controller may be further configurable to transmit, based on the processing, one or more commands to the surgical arm assembly 130, joint driving assembly 140, rotary driving assembly 150, and/or telescopic driving assembly 160. The one or more commands transmitted may include commanding the first joint driving subassembly 142 of the joint driving assembly 140 to drive the first joint assembly 135 in such a way as to cause a movement (and/or maintain a position or non-movement) of the surgical arm 130 connected to the distal end of the first joint assembly 135 (e.g., the second segment 132) relative to the first segment 131. The one or more commands transmitted may also include commanding the second joint driving subassembly 144 of the joint driving assembly 140 to drive the second joint assembly 136 in such a way as to cause a movement (and/or maintain a position or non-movement) of the portion of the surgical arm 130 connected to the distal end of the second joint assembly 136 (e.g., the end effector joint assembly 137) relative to the second segment 132. The one or more commands transmitted may include commanding the end effector joint driving subassembly 146 of the joint driving assembly 140 to drive the end effector joint assembly 137 in such a way as to cause a movement (and/or maintain a position or non-movement) of the portion of the surgical arm 130 connected to the distal end of the end effector joint assembly 137 (e.g., the end effector assembly 133) relative to the second joint assembly 136.

In an example embodiment, the controller may be configurable to detect a resistance in a movement of at least a part of the surgical arm assembly 130 (e.g., the end effector assembly 133 and/or the instrument 134) caused by an external factor (e.g., an interior of a patient cavity, another element of the surgical system 100 such as the surgical arm assembly 120 or another surgical arm assembly 130) and communicate a haptic feedback response to the surgeon or surgical team via the user interface. When the controller detects a resistance in a movement of at least a part of the surgical system 100 or 200, the controller may be configurable to determine the part of the surgical system 100 or 200 (e.g., instrument 134) encountering the resistance. Furthermore, the controller may be configurable to provide a haptic feedback response to the user interface based on such determining.

The controller may also be configurable to receive one or more of a plurality of responses, feedback, actions, and/or measurements from one or more elements of the surgical system 100 or 200 including, but not limited to, movements of one or more elements of the surgical system 100 or 200, haptic feedback responses, and responses and/or measurements pertaining to position (including orientation), applied force, proximity, temperature, pressure, humidity, etc., of, by, and/or nearby to the surgical arm assembly 130.

In an example embodiment, the controller may be configurable to receive, from the user interface, user interactions (e.g., by the surgeon or surgical team) performed on the user interface representative of commanding an energy source (not shown) to apply an electric current (e.g., a first electric current) to the instrument 134. In doing so, such electric current (e.g., first electric current) enables the instrument 134 to perform the actions of an electrosurgical instrument. In example embodiments, when the controller receives, from the user interface, the user interactions performed on the user interface representative of commanding the energy source to apply (or not apply) the electric current (e.g., first electric current) to the instrument 134 to perform (or not perform) the actions of an electrosurgical instrument, the controller may be configurable to transmit a command to the energy source to apply (or not apply) the electric current to the instrument 134.

In example embodiments, the controller may be separate from the user interface. Alternatively, the controller may include a part or all of the user interface, or may communicate with a processor of the user interface.

User Interface.

In example embodiments, the surgical system 100 or 200 may include a user interface (not shown). The user interface may be configurable for use by one or more operators (e.g., one or more members of the surgical team). The user interface may be configurable to receive one or more of a plurality of user interactions from the one or more operators and command one or more elements of the surgical system 100, 200 to perform an action or prevent from performing an action. Such receiving may be via the controller and/or directly from the one or more elements of the surgical system 100 or 200. For example, the user interface may be configurable to control (e.g., via the controller) a movement of one or more parts of the surgical system 100 or 200, such as the instrument 134 and other parts of the surgical system 100 or 200.

The user interface may also be configurable to receive one or more of a plurality of responses, feedback, actions, and/or measurements from one or more elements of the surgical system 100 or 200 and/or the controller including, but not limited to, movements of one or more elements of the surgical system 100 or 200, haptic feedback responses, and responses and/or measurements pertaining to position (including orientation), applied force, proximity, temperature, pressure, humidity, etc., of, by, and/or nearby to the surgical arm 130.

In example embodiments, the user interface may be separate from the controller. Alternatively, the user interface may include a part or all of the controller, or may include a processor in communication with the controller. The surgical system 100 or 200 may include a memory (not shown) in communication with the controller and/or user interface. The memory may be for use in storing information received from, processed by, and/or communicated to/from the controller and/or user interface. The user interface may also include one or more graphical interfaces (such as a monitor, projection system, etc.) for use in displaying video and/or audio content captured by an element of the surgical system 100 or 200 (such as a camera 134). The one or more graphical interfaces may also be for use in displaying some or all responses, feedback, actions, and/or measurements received from one or more elements of the surgical system 100 or 200 and/or the controller including, but not limited to, movements of one or more elements of the surgical system 100 or 200, haptic feedback responses, and responses and/or measurements pertaining to position (including orientation), applied force, proximity, temperature, pressure, humidity, etc., of, by, and/or nearby to the surgical arm 130.

While various embodiments in accordance with the disclosed principles have been described above, it should be understood that they have been presented by way of example only, and are not limiting. Thus, the breadth and scope of the example embodiments described in the present disclosure should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

For example, "assembly," "device," "portion," "segment," "member," "body," or other similar terms should generally be construed broadly to include one part or more than one part attached or connected together.

Various terms used herein have special meanings within the present technical field. Whether a particular term should be construed as such a "term of art" depends on the context in which that term is used. "Connected," "connecting," "attached," "attaching," "anchored," "anchoring," "in communication with," "communicating with," "associated with," "associating with," or other similar terms should generally be construed broadly to include situations where attachments, connections, and anchoring are direct between referenced elements or through one or more intermediaries between the referenced elements. These and other terms are to be construed in light of the context in which they are used in the present disclosure and as one of ordinary skill in the art would understand those terms in the disclosed context. The above definitions are not exclusive of other meanings that might be imparted to those terms based on the disclosed context.

As referred to in the present disclosure, a computing device, controller, manipulator, master input device, a processor, and/or a system may be a virtual machine, computer, node, instance, host, and/or device in a networked or non-networked computing environment. A networked computing environment may be a collection of devices connected by communication channels that facilitate communications between devices and allow devices to share resources. Also as referred to in the present disclosure, a computing device may be a device deployed to execute a program operating as a socket listener and may include software instances.

Resources may encompass any type of resource for running instances including hardware (such as servers, clients, mainframe computers, networks, network storage, data sources, memory, central processing unit time, scientific instruments, and other computing devices), as well as software, software licenses, available network services, and other non-hardware resources, or a combination thereof.

A networked computing environment may include, but is not limited to, computing grid systems, distributed computing environments, cloud computing environment, etc. Such networked computing environments include hardware and software infrastructures configured to form a virtual organization comprised of multiple resources that may be in geographically disperse locations.

Furthermore, the coverage of the present application and any patents issuing from the present application may extend to one or more communications protocols, including TCP/IP.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. A surgical system for use in performing an in vivo surgical action, the surgical system comprising:
    a port assembly, the port assembly having an elongated tubular body with an internal channel, the internal channel of the port assembly forming a first axis, the port assembly having a proximal end and a distal end, the distal end configured to be inserted into a cavity of a patient;
    a surgical arm inserted through the internal channel of the port assembly from the proximal end of the port assembly to the distal end of the port assembly, the surgical arm having a plurality of segments and joint assemblies, including first and second segments, an end effector assembly, at least one joint assembly pivotally coupling a distal end of the first segment to a proximal end of the second segment, and at least one joint assembly pivotally coupling a distal end of the second segment to a proximal end of the end effector assembly;
    a rotary driving assembly, the rotary driving assembly having a rotary driving subassembly and a rotary driven subassembly, the rotary driven subassembly secured to a portion of a proximal end of the first segment of the surgical arm, the rotary driven subassembly configured to be driven by the rotary driving subassembly in such a way as to rotate the surgical arm relative to the port assembly, the rotation of the surgical arm by the rotary driving assembly being a rotation, around a second axis, of at least the first segment of the surgical arm that is secured to the rotary driven assembly, the second axis being an axis formed by a centerline drawn through an elongated portion of the first segment of the surgical arm, the second axis parallel to the first axis; and
    a telescopic driving assembly, the telescopic driving assembly having a telescopic driving motor assembly and a guide rod assembly, the telescopic driving motor assembly having a first end and a second end, the first end of the telescopic driving motor assembly secured to a portion of the proximal end of the port assembly, the second end of the telescopic driving motor assembly secured to a portion of the rotary driving assembly, the telescopic driving assembly configured to provide a linear displacement of both the first segment of the surgical arm and the rotary driving assembly relative to the port assembly without displacing the telescopic driving assembly relative to the port assembly, wherein the linear displacement provided by the telescopic driving assembly of both the first segment of the surgical arm and the rotary driving assembly relative to the port assembly is a movement of both the first segment of the surgical arm and the rotary driving assembly along the second axis, wherein the linear displacement provided by the telescopic driving assembly of both the first segment of the surgical arm and the rotary driving assembly relative to the port assembly is controlled by the guide rod assembly.

2. The surgical system of claim 1, wherein the rotary driving assembly further includes a rotary driving motor, the rotary driving motor in communication with the rotary driving subassembly and configurable to drive the rotary driving subassembly.

3. The surgical system of claim 1, wherein the movements of the surgical arm relative to the port assembly controllable by the rotary driving assembly and telescopic driving assembly are configurable to move independently from one another.

4. The surgical system of claim 1, wherein the surgical system includes at least 5 degrees of freedom, the 5 degrees of freedom including the pivotal movement of the second segment relative to the first segment, the pivotal movement of the proximal end of the end effector joint assembly relative to the second segment, the pivotal movement of the end effector assembly relative to the second joint assembly, the rotary movement of the first segment relative to the axis formed by the centerline drawn through the elongated portion of the first segment, and the linear displacement of the first segment along the axis formed by the centerline drawn through the elongated portion of the first segment.

5. The surgical system of claim 1, wherein
    the first segment includes at least an elongated linear portion and a substantially U-shaped portion connected to a distal end of the elongated linear portion; and
    the end effector assembly includes an instrument, the instrument being a retractor device, an image capturing device, or a suction and/or irrigation device.

6. The surgical system of claim 1, wherein one or more of the following apply:
    the surgical system further comprises a third joint assembly provided between the first joint assembly and the second segment, a proximal end of the third joint assembly pivotally coupling a distal end of the first joint assembly to a proximal end of the second segment, wherein the first joint assembly pivotally couples the distal end of the first segment to the proximal end of the second segment via the third joint assembly; and/or
    the surgical system further comprises a fourth joint assembly provided between the second joint assembly and the end effector joint assembly, a proximal end of the fourth joint assembly pivotally coupling a distal end of the second joint assembly to a proximal end of the end effector joint assembly, wherein the second joint assembly pivotally couples the distal end of the second segment to the proximal end of the end effector joint assembly via the fourth joint assembly.

7. A surgical system for use in performing an in vivo surgical action, the surgical system comprising:
    a port assembly, the port assembly configurable as an access point into a cavity of a patient, the port assembly having an elongated tubular body with an internal channel, the internal channel of the port assembly forming a first axis, the port assembly having a proximal end and a distal end, the distal end configured to be inserted into a cavity of a patient;
    a first surgical arm inserted through the internal channel of the port assembly and secured to the distal end of the port assembly, the first surgical arm having at least 7 degrees of freedom when secured to the port assembly, the first surgical arm having a plurality of internal gear and motor assemblies in the first surgical arm, each internal gear and motor assembly configured to drive each of the at least 7 degrees of freedom;
    a second surgical arm, the second surgical arm having at least 5 degrees of freedom when secured to the port assembly, the second surgical arm having a plurality of segments and joint assemblies drivable to move relative to one another via an application of a tensile force to one or more cables, the second surgical arm including first and second segments, an end effector assembly, at least one joint assembly pivotally coupling a distal end of the first segment to a proximal end of the second segment, and at least one joint assembly pivotally coupling a distal end of the second segment to a proximal end of the end effector assembly, the second surgical arm inserted through the internal channel of the port assembly from the proximal end of the port assembly to the distal end of the port assembly;

a rotary driving assembly, the rotary driving assembly having a rotary driving subassembly and a rotary driven subassembly, the rotary driven subassembly secured to a portion of a proximal end of the first segment of the second surgical arm, the rotary driven subassembly configured to be driven by the rotary driving subassembly in such a way as to rotate the second surgical arm relative to the port assembly, the rotation of the second surgical arm by the rotary driving assembly being a rotation, around a second axis, of at least the first segment of the second surgical arm that is secured to the rotary driven assembly, the second axis being an axis formed by a centerline drawn through an elongated portion of the first segment of the second surgical arm, the second axis parallel to the first axis; and a telescopic driving assembly, the telescopic driving assembly having a telescopic driving motor assembly and a guide rod assembly, the telescopic driving motor assembly having a first end and a second end, the first end of the telescopic driving motor assembly secured to a portion of the rotary driving assembly, the second end of the telescopic driving motor assembly secured to a portion of the proximal end of the port assembly, the telescopic driving assembly configured to provide a linear displacement of both the first segment of the second surgical arm and the rotary driving assembly relative to the port assembly without displacing the telescopic driving assembly relative to the port assembly, wherein the linear displacement provided by the telescopic driving assembly of both the first segment of the surgical arm and the rotary driving assembly relative to the port assembly is a movement of both the first segment of the surgical arm and the rotary driving assembly along the second axis, wherein the linear displacement provided by the telescopic driving assembly of both the first segment of the second surgical arm and the rotary driving assembly relative to the port assembly is controlled by the guide rod assembly.

8. The surgical system of claim 7, wherein the rotary driving assembly further includes a rotary driving motor, the rotary driving motor in communication with the rotary driving subassembly and configurable to drive the rotary driving subassembly.

9. The surgical system of claim 7, wherein the movements of the second surgical arm relative to the port assembly controllable by the rotary driving assembly and telescopic driving assembly are configurable to move independently from one another.

10. The surgical system of claim 7, wherein the at least 5 degrees of freedom of the second surgical arm includes a pivotal movement of the second segment relative to the first segment, a pivotal movement of the proximal end of the end effector joint assembly relative to the second segment, a pivotal movement of the end effector assembly relative to the second joint assembly, a rotary movement of the first segment relative to the axis formed by the centerline drawn through the elongated portion of the first segment, and a linear displacement of the first segment along the axis formed by the centerline drawn through the elongated portion of the first segment.

11. The surgical system of claim 7, wherein
the first segment includes at least an elongated linear portion and a substantially U-shaped portion connected to a distal end of the elongated linear portion; and
the end effector assembly includes an instrument, the instrument being a retractor device, an image capturing device, or a suction and/or irrigation device.

12. The surgical system of claim 7, wherein one or more of the following apply:
the surgical system further comprises a third joint assembly provided between the first joint assembly and the second segment, a proximal end of the third joint assembly pivotally coupling a distal end of the first joint assembly to a proximal end of the second segment, wherein the first joint assembly pivotally couples the distal end of the first segment to the proximal end of the second segment via the third joint assembly; and/or
the surgical system further comprises a fourth joint assembly provided between the second joint assembly and the end effector joint assembly, a proximal end of the fourth joint assembly pivotally coupling a distal end of the second joint assembly to a proximal end of the end effector joint assembly, wherein the second joint assembly pivotally couples the distal end of the second segment to the proximal end of the end effector joint assembly via the fourth joint assembly.

\* \* \* \* \*